US011101026B2

(12) United States Patent
Francois et al.

(10) Patent No.: US 11,101,026 B2
(45) Date of Patent: Aug. 24, 2021

(54) SCHEDULE-BASED ELECTRONIC MEDICAL RECORD MODULES, APPLICATIONS, AND USES THEREOF

(71) Applicant: Revon Systems, LLC, Crestwood, KY (US)

(72) Inventors: Cedric Francois, Prospect, KY (US); Gaurav Bazaz, Edgewater, NJ (US); Alec Machiels, New York, NY (US); Pascal Deschatelets, Prospect, KY (US); Monica Gerber, Somerville, MA (US)

(73) Assignee: Zyus Life Sciences US Ltd., Saskatoon (CA)

( * ) Notice: Subject to any disclaimer, the term of this patent is extended or adjusted under 35 U.S.C. 154(b) by 1351 days.

(21) Appl. No.: 14/945,991

(22) Filed: Nov. 19, 2015

(65) Prior Publication Data

US 2016/0147951 A1 May 26, 2016

Related U.S. Application Data

(63) Continuation of application No. PCT/US2014/040064, filed on May 29, 2014.
(Continued)

(51) Int. Cl.
*G16H 10/20* (2018.01)
*G16H 10/60* (2018.01)
(Continued)

(52) U.S. Cl.
CPC ............. *G16H 10/65* (2018.01); *G06Q 10/10* (2013.01); *G16H 10/20* (2018.01); *G16H 10/60* (2018.01);
(Continued)

(58) Field of Classification Search
None
See application file for complete search history.

(56) References Cited

U.S. PATENT DOCUMENTS 5,583,758 A * 12/1996 McIlroy ............... G16H 70/20
705/2
2003/0120516 A1 6/2003 Perednia et al.
(Continued)

FOREIGN PATENT DOCUMENTS

WO WO 2013/070895 A1 5/2013
WO WO 2014/105752 A1 7/2014
WO WO-2014178908 A1 * 11/2014 ............ G16H 80/00

OTHER PUBLICATIONS

Jones et al., The journey to electronic interdisciplinary care plans, Dec. 2012, Nursing Management, pp. 9-12, DOI-10.1097/01.NUMA. 0000422896.29829.03 (Year: 2012).*
(Continued)

*Primary Examiner* — Devin G Hein
(74) *Attorney, Agent, or Firm* — Frost Brown Todd LLC

(57) ABSTRACT

In some aspects, the present disclosure provides a computer program product for assembling a database comprising electronic data modules, which may be electronic medical records (EMRs). The present disclosure can also be used for purposes such as implementing a system in which physicians and patents can be provided with applications that they can use to confirm that various disease related events have taken place. This can be performed using active diagnosis modules (ADMs) comprising schedules of events. These ADMs and their events can also be used to populate a database which can be used for purposes such as identifying, recruiting and tracking participants in clinical trials.

20 Claims, 31 Drawing Sheets

Related U.S. Application Data

(60) Provisional application No. 61/828,614, filed on May 29, 2013.

(51) Int. Cl.
  *G16H 40/20* (2018.01)
  *G06Q 10/10* (2012.01)
  *G16H 20/30* (2018.01)
  *G16H 10/65* (2018.01)
  *G16H 70/60* (2018.01)

(52) U.S. Cl.
  CPC ............. *G16H 20/30* (2018.01); *G16H 40/20* (2018.01); *G16H 70/60* (2018.01)

(56) References Cited

U.S. PATENT DOCUMENTS

| | | |
|---|---|---|
| 2004/0088192 A1 | 5/2004 | Schmidt et al. |
| 2007/0156032 A1 | 7/2007 | Gordon et al. |
| 2007/0198296 A1* | 8/2007 | Pellinat .............. G06F 19/3418 |
| | | 705/2 |
| 2008/0021739 A1 | 1/2008 | Brock |
| 2008/0201174 A1 | 8/2008 | Ramasubramanian |
| 2009/0125335 A1* | 5/2009 | Manetta ................ G16H 10/60 |
| | | 705/3 |
| 2010/0004948 A1* | 1/2010 | Toomey ................ G06Q 50/22 |
| | | 705/3 |
| 2010/0250285 A1* | 9/2010 | Shelton ............... G06F 21/6254 |
| | | 705/3 |
| 2014/0244309 A1 | 8/2014 | Francois |

OTHER PUBLICATIONS

International Search Report and Written opinion dated Dec. 1, 2014 for Application No. PCT/US2014/040064.
U.S. Appl. No. 61/828,614, filed May 29, 2013.

* cited by examiner

My Physicians
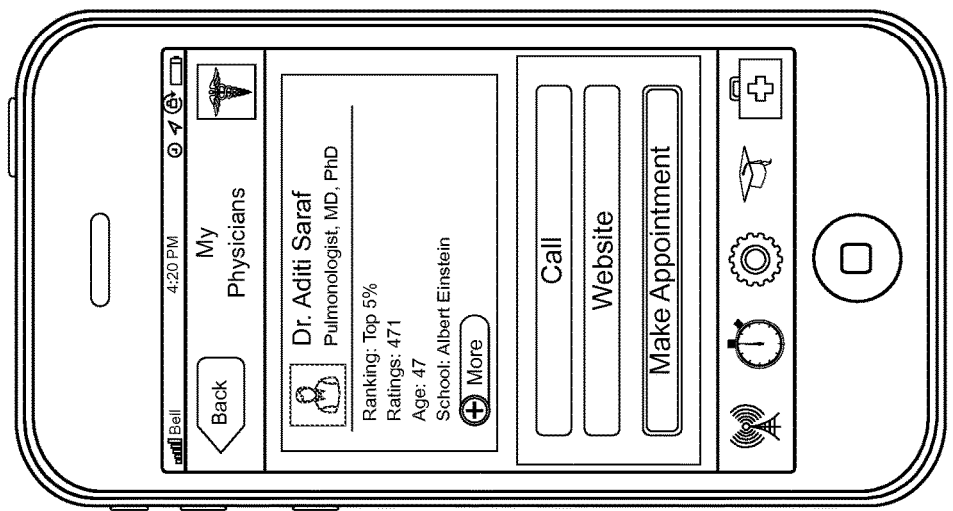
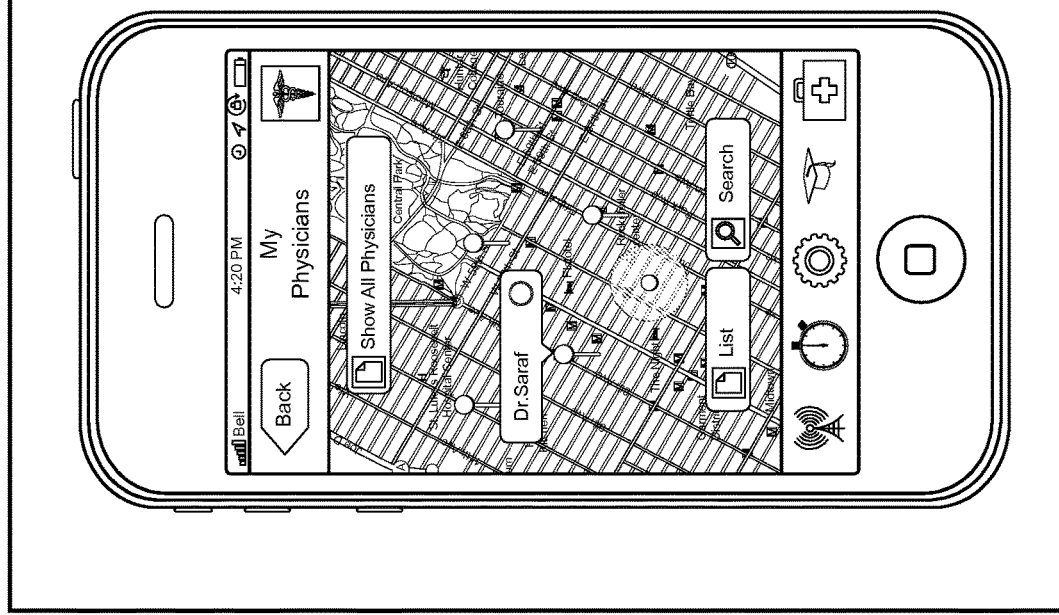
FIG. 3D

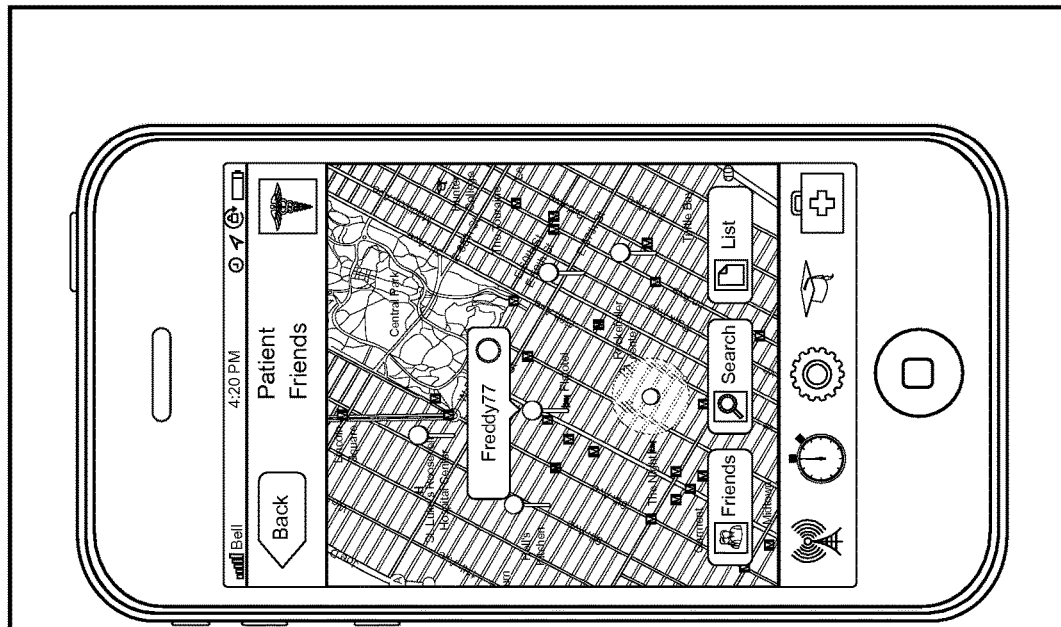
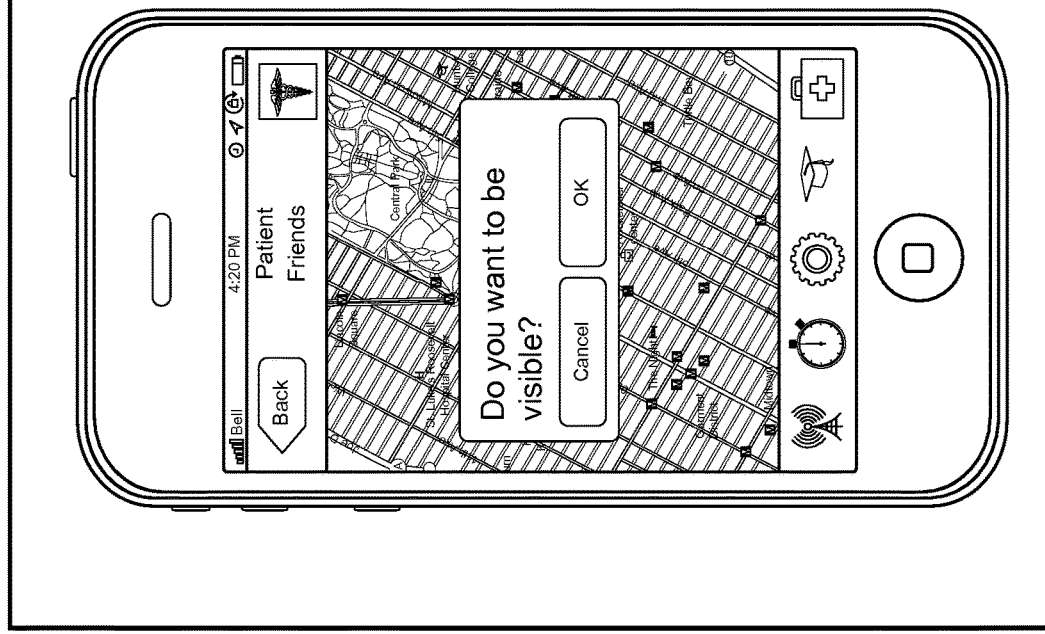
FIG. 3H

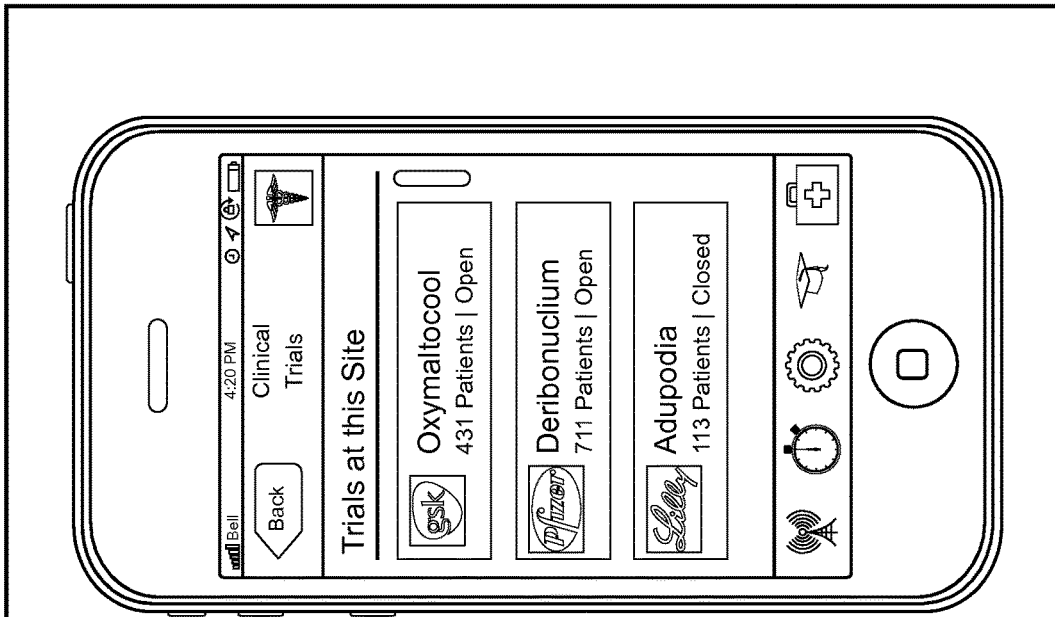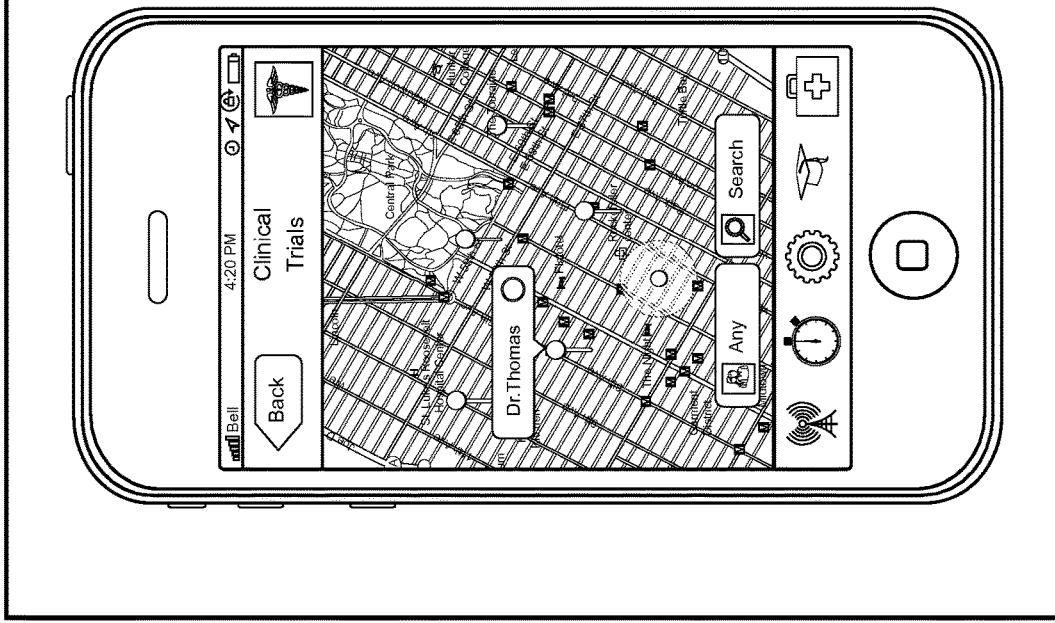
FIG. 3M

*Physicians Screens*

1

Revon
Systems LLC.

[Manage Templates] [Settings] [Logout]

Search [SSN, DOB or Name]   [Settings]

| ID | Patient Name | DOB | Age | Gender | Email | Phone |
|---|---|---|---|---|---|---|
| GT87 | John James | 10/1/10 | 62 | Male | xhs@hg.com | 282618181 |
| 67AG | John River | 10/2/10 | 83 | Male | xhsg@hg.com | 378276212 |
| 6S65 | John Hudson | 10/4/10 | 82 | Male | ats@hg.com | 283628291 |
| 7FR1 | John Thames | 10/20/90 | 90 | Female | kes@hg.com | 292867323 |

2

Revon
Systems LLC.

[Manage Templates] [Settings] [Logout]

Search [SSN, DOB or Name]   [Settings]

John James

Age          Email              [Add ADM]
Gender       Phone (cell)       [Send Email]
Race         Phone (landline)   [Call]
Ethnicity    Phone (emergency)

Next Visits                Active ADM's
                           Under you
                           [ Type II Diabetes ] [Edit]

Other ADM's
Prior Visits               [ Macular Degeneration ]

[ COPD ]

5 rºRevon
Systems LLC.

[Manage Templates] [Settings] [Logout]

Search  [SSN, DOB or Name]  [Settings]

Manage Templates

| ID | Template Name | Created Date | Disease Code | Last Updated | Created By | Patients Using |
|---|---|---|---|---|---|---|
| GT87 | Daibetes | 10/2/10 | 62 | 10/2/10 | XGHSGF | 625 |
| 67AG | Headache | 10/2/10 | 83 | 10/2/10 | SHAT SGS | 72 |
| 6S65 | Zonkuphobia | 10/4/10 | 82 | 10/2/10 | HSG AST | 27 |
| 7FR1 | Adutrilia | 10/20/90 | 90 | 10/2/10 | SHg GA | 187 |

---

6 rºRevon
Systems LLC.

[Manage Templates] [Settings] [Logout]

Search  [SSN, DOB or Name]  [Settings]

Settings

Appointments

How would you like to receive appointments?

Phone  [        ]
Email  [        ]
ZocDoc ID  [        ]

[Edit Profile]
[Change Password]
[Deactivate Account]

Notifications

Would you like to receive notifications?

New Literature  [Yes ▽]
New Therapies  [Yes ▽]

FIG. 6D

SCHEDULE-BASED ELECTRONIC MEDICAL RECORD MODULES, APPLICATIONS, AND USES THEREOF

CROSS-REFERENCE TO RELATED APPLICATIONS

This application claims priority from, and is a continuation of, international application PCT/US2014/040064, with an international filing date of May 29, 2014, which itself claims priority from U.S. Provisional Patent Application Ser. No. 61/828,614, filed on May 29, 2013. The entire contents of each of these applications are incorporated herein by reference.

BACKGROUND

Medical records have traditionally been written on paper and maintained in folders. These folders are often divided into multiple sections, with new information added to each section as relevant over time. Retrieving paper records when needed may be time-consuming, particularly if they have been archived off-site. Patients may have multiple medical records generated at different medical facilities at which they have received care. For example, a patient's primary care provider may not have ready access to a medical record generated at a hospital where a patient received surgery. Another problematic feature of traditional medical records is the use of handwriting by health care providers, which may at times be difficult to decipher. Standard electronic medical records (EMRs) may offer, among other things, the possibility of increased accessibility and legibility. While standard EMRs undoubtedly offer many potential benefits, the entry of accurate and comprehensive information regarding a patient into a standard EMR may be burdensome.

SUMMARY

In some aspects, the disclosure provides a computer program product for assembling a database comprising electronic medical records (EMRs). An "electronic medical record" may sometimes be referred to as an "electronic health record", "electronic health care record", "electronic patient record", or various similar terms. Such terms may be considered equivalent and interchangeable.

In some aspects a computer program product for creating, augmenting, or updating electronic medical records (EMRs) or electronic medical data modules is provided, the computer program product comprising a computer-readable medium encoded with computer-executable instructions for performing a method comprising: (a) receiving input comprising a disease identifier and a patient identifier; (b) generating a schedule of events for managing the disease; and (c) receiving input indicating that an event has occurred. In some embodiments, the events are selected by a treating physician for managing the disease for that patient. In some embodiments, the events comprise physician events and patient events. In some embodiments, the computer-executable instructions comprise instructions for providing an output comprising the schedule to a treating physician and a patient.

In some embodiments, the computer-executable instructions comprise instructions for modifying the schedule in response to an input. In some aspects, the computer-executable instructions comprise: (i) instructions for receiving an input indicating that an event occurred, wherein the input optionally comprises a date or approximate date that the event occurred, a result of the event, or both, and (ii) instructions for updating the schedule upon receipt of the input to indicate that the event occurred. In some aspects, the computer-executable instructions comprise (i) instructions for receiving a plurality of inputs over time indicating that a plurality of events occurred, wherein an input optionally comprises a date or approximate date that an event occurred, a result of the event, or both, and (ii) instructions for updating the schedule upon receipt of an input to indicate that an event occurred, so as to maintain an ongoing record of events relevant to management of the disease over a time period of at least 3 months. In some aspects, the computer-executable instructions comprise instructions for: updating a patient application as dates scheduled for events approach, issuing a notification to a patient application, enrolling a patient in a patient network, ranking a patient based on their adherence to their schedule.

In some aspects, a computer program product is provided comprising computer-executable instructions for: (i) generating a schedule for performing physician events and patient events relevant to managing a disease, (ii) storing the schedule in association with an identifier of a patient who has the disease and the treating physician of the patient, (iii) causing the schedule to be displayed on a device controlled by the physician or a device controlled by the patient upon receiving a request from the physician device or patient device, respectively; (iv) updating the schedule based on one or more inputs indicating that a physician event or a patient event has occurred. In some aspects, physician events include diagnostic procedures and therapeutic procedures and patient events include taking medications, performing body monitoring, diet, and exercise.

In some aspects, a computer program product is provided comprising computer-executable instructions for displaying information relevant to one or more of a plurality of diseases that a patient has, wherein the information is viewable on a display consolidated across all diseases on a single screen or as disease-specific information on disease-specific screens. In some aspects, navigation between disease-specific screens or between the consolidated screens and a disease-specific screen is accomplished by moving horizontally across the screen or vertically along the screen. In some aspects, navigation between disease-specific screens or between the consolidated screens and a disease-specific screen is accomplished on a device with a touch-sensitive screen by swiping horizontally across the screen or vertically along the screen.

In some aspects, the information comprises information relevant to management of the diseases. In some aspects, the information comprises a schedule of physician events for managing each of the plurality of diseases, wherein the physician events for each disease are selected by a patient's treating physician for that disease. In some aspects, the information is of at least two different categories, wherein information in each category is viewable consolidated across all diseases on a single screen or as disease-specific information on disease-specific screens, wherein selection of a category may be made from a home screen or from a main screen for each disease. In some aspects, the information categories comprise at least two of the following: (1) information identifying at least some of patient's physicians; (2) information identifying at least some of a patient's friends who have at least one disease that the patient has; (3) information identifying physician events; (4) information identifying patient events; and (5) information identifying clinical trials for treatment of a disease that the patient has.

In some aspects, the computer program product comprises an application that runs on a portable electronic device.

In some aspects, a method of managing a patient having a disease is provided, the method of managing a patient having a disease comprising steps of: (a) receiving, in a system, input comprising a patient identifier and a disease diagnosis; (b) generating a schedule of treating physician-selected events for managing the disease; (c) providing the patient with an application that allows for display of the schedule, generates reminders of events, and enables a patient to communicate with other patients who have the same disease; (d) receiving input confirming the occurrence of a plurality of events in the schedule; (e) updating the schedule based on the input. In some aspects, the application runs on a portable electronic device. In some aspects, the method of managing a patient having a disease further comprises ranking the patient's adherence to the schedule as compared with other patients with the same disease or informing the patient, optionally further comprising providing feedback to the user based at least in part on the ranking.

In some aspects, a method of managing a patient having a disease is provided, the method of managing a patient having a disease comprising steps of: (a) receiving in, a system, an input comprising a patient identifier and a disease diagnosis; (b) generating a schedule of treating physician-selected events for managing the disease; (c) providing the treating physician with access to the schedule; (d) providing the patient with an application that allows for display of the schedule, generates reminders of events, and enables a patient to communicate with other patients who have the same disease; (e) receiving input confirming the occurrence of a plurality of events in the schedule; (e) updating the schedule for both the treating physician and the patient based on the input. In some aspects, the application runs on a portable electronic device.

BRIEF DESCRIPTION OF THE DRAWINGS

FIGS. 6A-6D show physician screen flow (6A) and screens (6B-D) of an ADM application according to certain embodiments.

DETAILED DESCRIPTION

Overview

Figure 1:
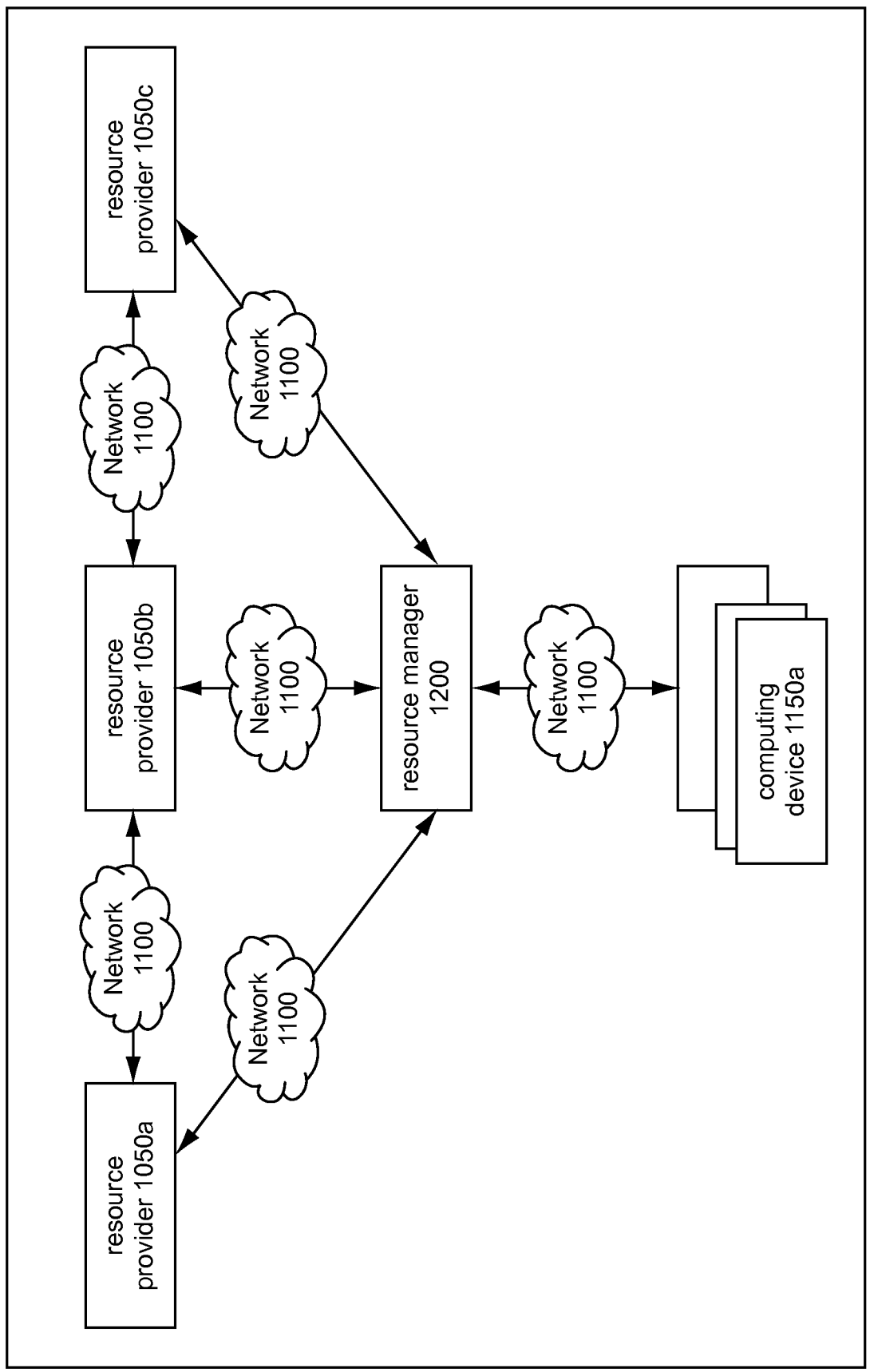
FIG. 1 is a diagram showing an implementation of a cloud computing system in accordance with some embodiments.

In accordance with some aspects, health information (data) regarding an individual may be electronically received from a contributor. A contributor may be a health care provider (HCP) of the individual. For purposes hereof, a collection (set) of health information regarding an individual may be referred to as a "health information dataset". A health information data set can include information, such as information indicating whether disease related events on a schedule of events from an active diagnosis module (ADM) have taken place. These ADMs and their events can also be used to populate a database which can be used for purposes such as identifying, as well as other health information received from a variety of sources (e.g., third party EMR databases, applications provided to patients or physicians, etc) can be used to populate a database which can in turn be used for purposes such as medical research and/or the identification, recruitment and tracking of individuals in clinical trials.

Revon System

In some aspects, a system, application, database, or network described herein may be referred to as a Revon system, Revon application, Revon database, or Revon network, respectively. It should be understood that systems, applications, databases, or networks, referred to by terms that comprise name "Revon" (such as "Revon system"), and the various modules and components thereof, encompass any of a variety of embodiments and may be implemented in any of a variety of ways. The use of the name "Revon", whether by itself or in combination with one or more additional terms, is not to be considered limiting. Any embodiment or variation of a system, application, database, network, etc., described herein may be referred to as the (or a) Revon system, Revon application, Revon database, Revon network, etc., respectively. A Revon system, Revon application, Revon database, Revon network, etc., may comprise any of the capabilities, features, and/or functions of a system, application, database, network, etc., respectively, described anywhere in this document in various embodiments. Any of the capabilities, features, and/or functions described in regard to a Revon system, Revon application, Revon database, Revon network, etc., may be utilized in combination with capabilities, features, and/or functions described anywhere in this document in various embodiments.

In some embodiments a Revon system comprises functionality for creating, accessing, and updating electronic data modules that aggregate a patient's medical data (health information) relevant to a particular disease. Such a data module may be referred to as an active diagnosis module (ADM). In certain embodiments an ADM comprises a disease diagnosis and one or more schedules (sometimes referred to as "ADM schedule", or simply "schedule") that serve as a central interface between the patient, the physician, and, in some embodiments, one or more EMRs or EMR systems that contain data relevant to the disease. In some embodiments such EMRs or EMR systems may contribute to a schedule or serve as a source of information that is included in a schedule. A "schedule" comprises one or more disease-relevant events and associated times at which the events are to be performed (for future events) or have been performed (for past events). In general, a "disease-relevant event" may be any event that is relevant to a disease, e.g., an event that may be considered by a physician to be important in the management (e.g., treating, monitoring, etc.) of a disease. In this context, a "disease-relevant event" does not refer to an event or occurrence that is part of a disease (e.g., a symptom or other manifestation of a disease) but rather to an event that is associated with or comprises an action or activity that is or may be taken or performed by a physician or patient that is relevant to the disease. An event or occurrence that is part of a disease, e.g., a patient experiencing a symptom or other manifestation of a disease, may be referred to as a "disease event". In accordance with some embodiments, a patient has a treating physician for each disease, who specifies the disease-relevant events for that disease for that patient, which events may be included in an ADM schedule. A treating physician for one or more of a patient's ADMs may be a primary care physician. The particular events to be included in an ADM schedule may be selected by the treating physician, by the Revon system, or by a combination thereof, e.g., by the physician with input or advice from the system. In general, the treating physician specifies the events to be included on a schedule for a patient but may use a default schedule supplied by the Revon system. An ADM schedule constitutes in essence a physician's treatment plan for a patient, including events to be performed by a physician or other HCP or otherwise in a health care setting ("physician events", discussed further below) and actions or behaviors that the physician recommends to the patient as part of patient self-management ("patient events", discussed further herein). The schedule thus captures the recommendations and/or preferences of the physician primarily responsible for treating a particular patient with the disease in question. In some embodiments, disease-relevant data for a particular disease with which a patient has been diagnosed is electronically logged on one or more schedules for that disease. Such data may include, for example, the occurrence of and/or result(s) of particular events as confirmed by a physician or by the patient. In some aspects, the Revon system thus provides for disease-relevant event integration. A data module, e.g., an ADM, that comprises medical data of a patient relevant to a disease may be de-identified. The de-identified medical data may be used for any of a variety of purposes described herein. An ADM schedule is no different in this regard. The events and patient data included in an ADM schedule may be stored in any manner and converted to or from a schedule format as desired.

It should be understood that "time" in the context of a schedule, e.g., time for future events, often does not refer to a specific time as determined by a clock (e.g., a particular timepoint within a 24 hour day) on a specific date but rather when or approximately when an event is to take place within the continued progress of existence and events that individuals (e.g., physicians, patients) experience. Times for future events that are to occur on a recurring basis may often be expressed as frequencies (e.g., every 3 months) or time intervals (e.g., 3 months apart). A schedule may not include specific dates for at least some future events. In certain embodiments at least some times may be approximate. A schedule for future events may be adjusted to take into consideration the fact that certain days may be weekends, holidays, or other days on which it would not ordinarily be expected that the event would be scheduled to take place. For example, if a frequency of "every 3 months" would result in an event becoming due on a weekend date, the event may be considered due on the closest earlier or later weekday. A schedule may include physician events that are to take place in the future but for which a specific date and time of day have not yet been arranged. In such instances, a physician event as presented on a patient schedule may comprise a reminder to arrange a specific time and day for the associated actual physician event to take place, e.g., a reminder to make an appointment for a procedure. If a specific date and time have been arranged, a schedule may reflect that fact. In the case of an event that has occurred, a schedule may include a date or approximate date of occurrence. A schedule may have any of a variety of formats in which events are associated with times. It may comprise or consist of words, diagrams, or combinations thereof. For example, a schedule may comprise a timeline in which the passage of time is shown from left to right and events that are to occur or that have occurred are indicated at various positions along the timeline, e.g., below it. The schedule may be in the form of a two-dimensional grid with time along the x-axis, and events of different types distributed along the y-axis (or vice versa). A symbol such as an X may indicate the time or approximate time at which an event is to occur or occurred (different symbols or colors may be used to distinguish events that occurred or are to occur or did not occur as scheduled). A schedule may be displayed as a calendar with events indicated in different boxes representing different days. Various display formats may be used, and the examples herein (e.g., in the Figures) are not to be considered limiting. A schedule may have one or more capabilities, data, and/or functions associated with it. For example, events may have associated data, which may be accessed from the schedule (e.g., by clicking on the event). The data used to populate a schedule may be stored in one or more databases and used for any of a variety of purposes, e.g., as described herein, e.g., any of the various purposes for which an EMR database or ADM database may be used.

In some embodiments disease-relevant events may be classified into six categories, though greater or larger numbers of categories of disease-related events could also be used when implementing the technology described herein. In implementations with six categories, two of those six categories can pertain to physician events, i.e., (1) Diagnostic Procedures, and (2) Therapeutic Procedures. Other physician events such as Hospital Admissions or others can be added as well. In addition to these two categories, there may be up to four additional categories (sometimes referred to herein as "patient events" or "My Events") that generally involve patient-performed actions or behaviors typically performed outside a health care setting (e.g., at home): (3) Medications; (4) Body Monitoring; (5) Diet; and (6) Exercise. (5) Diet and (6) Exercise can in certain embodiments be merged into a Lifestyle category. As noted above, in some embodiments physician events and patient events are specified by the treating physician, are entered on the ADM schedule for the patient, and, upon confirmation of their occurrence, are or can be logged in the ADM schedule for that patient. In some embodiments there may be at least two types of physician events. A first type of physician event (Type I) comprises physician events that a treating physician performs or orders as part of his or her plan for management of a disease for a particular patient. A second type of physician event (Type II) comprises physician events that are considered relevant to a particular disease or its management by the treating physician but are not necessarily part of the physician's treatment plan for the disease for that particular patient, although they may be. For example, a physician treating a patient for COPD may consider an imaging study of the lungs (e.g., a chest X-ray) to be relevant to the disease or its management, regardless of why the imaging study was performed. Such a physician event may be a Type II physician event for COPD for that patient. A Type II physician event may be performed, for example, as part of a treatment plan for a different disease for which the patient also has an ADM, as part of diagnosis or treatment of a different disease for which the patient does not have an ADM, on an unscheduled basis (e.g., if the patient visits a physician (either the treating physician for the disease or a different physician) for an acute condition (e.g., a respiratory tract infection) or an exacerbation of an existing disease, visits an emergency room, is hospitalized, etc. It will be understood that a physician event may be a Type I event for one or more ADMs and a Type II event for one or more different ADMs. It will be understood that Type I and II events do not necessarily need to be present on the Schedule as separate categories, but can be identified as Type I or Type II when they are logged as being performed on the Schedule.

Physician events encompass any procedures, tests, or services (collectively "procedures") performed by a HCP in the context of a direct or indirect treatment relationship with a patient. Typically a procedure is performed in a health care setting such as a physician's office or clinic, hospital, etc. but may be performed anywhere that a HCP provides health care. Physician events may be procedures that are performed as part of a direct treatment relationship between a patient and a health care provider and procedures that are performed as part of an indirect treatment relationship, e.g., a relationship in which (1) A health care provider delivers care to a patient based on the orders of another health care provider; and (2) The health care provider reports the diagnosis or results associated with the care to another health care provider (e.g., the ordering health care provider), who provides the diagnosis or results to the patient or utilizes the diagnosis or results in diagnosing or managing (e.g., treating) the patient. Certain physician events, e.g., certain procedures, may not necessarily be performed by a physician or, if performed by a physician, the physician who actually performs the procedure may not be the physician responsible for ordering it. For example, the term "physician event" encompasses events that may be performed by non-physician health care providers and/or performed upon order of a physician by a non-physician or by a different physician. It is important to note that there is typically one Treating Physician in charge of one ADM Schedule in at least some embodiments. When an existing ADM Schedule is modified by a new physician (for example because the patient decided to change physicians) then that physician typically becomes the Treating Physician in at least some embodiments. Physician events may include, for example, procedures and tests performed at least in part by a clinical laboratory, imaging center, or other entity that provides medical or health services, etc. Physician events may include any physician service, physical or occupational therapy service, radiologic procedure, clinical laboratory tests, other medical diagnostic procedures (e.g., pathology, molecular diagnostic tests), etc. A physician event may be classified as a diagnostic procedure or a therapeutic procedure but the term encompasses procedures performed for disease prevention, diagnosis and/or management (e.g., treatment, monitoring). It will be appreciated that many procedures that may be performed to determine whether a patient has a disease or which disease a patient has may be performed after diagnosis for purposes of monitoring the patient (e.g., assessing the condition of the patient, response to treatment, progression or resolution of the disease, etc.). A physician event may have (i) a code in the ICD-10-PCS, (ii) a code in the Healthcare Common Procedural Coding System (HCPCS), e.g., a Common Procedural Terminology (CPT)® code set, or (iii) both. In certain embodiments, a procedure has an ICD-10-PCS code if performed on a hospital inpatient and a HCPCS code, e.g., a CPT code, if performed on a patient who is not a hospital inpatient. In certain embodiments physician events that occur while a patient is hospitalized may be differentiated from outpatient physician events on an ADM schedule (e.g., by use of a different color, different symbols, or an indicator such as an asterisk). In some embodiments a physician event may correspond precisely to a particular procedure code or group of codes. In some embodiments a physician event may not correspond precisely to a particular procedure code or group of procedure codes.

Patient events encompass taking medications recommended, e.g., prescribed, by a HCP; body monitoring; diet; and exercise. These types of patient activities are discussed elsewhere herein. It should be understood that certain types of procedures may be a physician event or a patient event depending on the context in which they are performed, and by whom. For example, a blood glucose test may be a physician event (a diagnostic procedure) if performed by a nurse when a patient visits his or her physician and a patient event (body monitoring) if performed by the patient at home. Similarly, an insulin injection may be a physician event (a treatment procedure) if performed by a nurse when a patient visits his or her physician and a patient event (medication) if performed by the patient at home.

In some embodiments an ADM for a particular patient comprises a first schedule for use by one or more of the patient's physician(s) and/or other HCPs of the patient ("physician ADM schedule") and a second schedule ("patient ADM schedule") for use by a patient. In general, the same events appear on both the physician schedule and patient schedule for a particular patient, but the schedules and/or one or more associated capabilities and/or functions may differ in one or more respects and/or may be used for different purposes. A physician ADM schedule may in some embodiments be used by a physician's (or other HCPs) designees (e.g., administrative assistants, office managers, nurses etc.), who may or may not be HCPs. In some embodiments such individuals may have their own accounts and/or may be authorized to select, modify or update an ADM. The system may permit a HCP to designate such users of his or her physician ADMs. A patient ADM schedule may in some embodiments be used by a patient's designees (e.g., family, home caregivers) and/or legal guardians. The system may permit a patient to designate such users.

A physician ADM schedule may be made available to its users via an application or website. A patient ADM schedule may be made available to its users via, e.g., an application (e.g., which may run on a portable electronic device such as a smartphone) or website. For purposes of description it is sometimes assumed herein that a patient schedule is made available via an application, which may be termed a "patient application" and the physician schedule is made available via an application, which may be termed a "physician application". The Revon system may comprise a website, which may provide web portals for physicians and patients. A web portal may be a page or section of a website that is dedicated to a particular constituency, such as physicians or patients, and may serve as an entry point to portions of the website that serve that constituency, e.g., by providing access to particular web pages, e.g., web pages through which users interact with the Revon system. Web portals may be provided for sponsors, payers, regulators, or other constituencies.

A portable electronic device such as could be used with the technology disclosed herein may comprise any suitable type of electronic device. For example, the electronic device may comprise a portable electronic device that a user may hold in his or her hand, such as a portable digital assistant (PDA), also referred to as a portable data assistant, a smartphone, a tablet computer, etc. The electronic device may be a larger portable electronic device, such as a laptop computer. As known in the art, PDAs are small, e.g., hand-held, computers, that are frequently used for tasks such as maintaining a calendar, list of contacts (e.g., email addresses), and other information. PDAs may contain application programs such as word processing programs, web browsers, PDF viewers, etc. As used herein, a "smartphone" may be an electronic device that combines the functions of a wireless phone and a PDA within a single unit. A tablet computer may be a computer that is may be somewhat larger than a mobile phone or personal digital assistant, comprises a flat touch screen, and is primarily operated by touching the screen. It may use an onscreen virtual keyboard.

Often a portable electronic device may weigh under about 1-2 pounds, e.g., between about 3 ounces and about 1.5 pounds. For example, a smartphone or PDA may weigh between about 3 ounces and about 6 ounces and height and width dimensions in the range of less than about 7×5 inches and depth less than about 0.5-1.0 inch, though smaller or larger weight and/or dimensioned devices may be used. Exemplary portable electronic devices include, e.g., a PDA such as an iTouch (Apple, Inc.), a smartphone such as an iPhone (Apple, Inc.) or Galaxy phone (Samsung), or a tablet computer such as the iPad or iPad mini (Apple, Inc.). In some embodiments a portable electronic device may be wearable, e.g., as a wristwatch, armband, etc.

A portable electronic device may include components that may be found in such devices, e.g., control circuitry, storage/memory, input/output circuitry, communications circuitry, processing circuitry, etc. In some embodiments, one or more of such components of the device may be combined or omitted. In some embodiments, the portable electronic device may include other components such as, for example, a proximity sensor, a power supply such as a battery, a display, a positioning system, a camera, an accelerometer, an ambient light sensor, other sensors, an input mechanism, etc.) or multiple instances of one or more such components. In many embodiments, the portable electronic device may possess wireless connectivity. For example, the device may have Bluetooth, Wi-Fi wireless network connectivity, and/or the ability to connect to wireless Wide Area Networks, such as those provided by cellular telecommunications companies.

Figure 7:
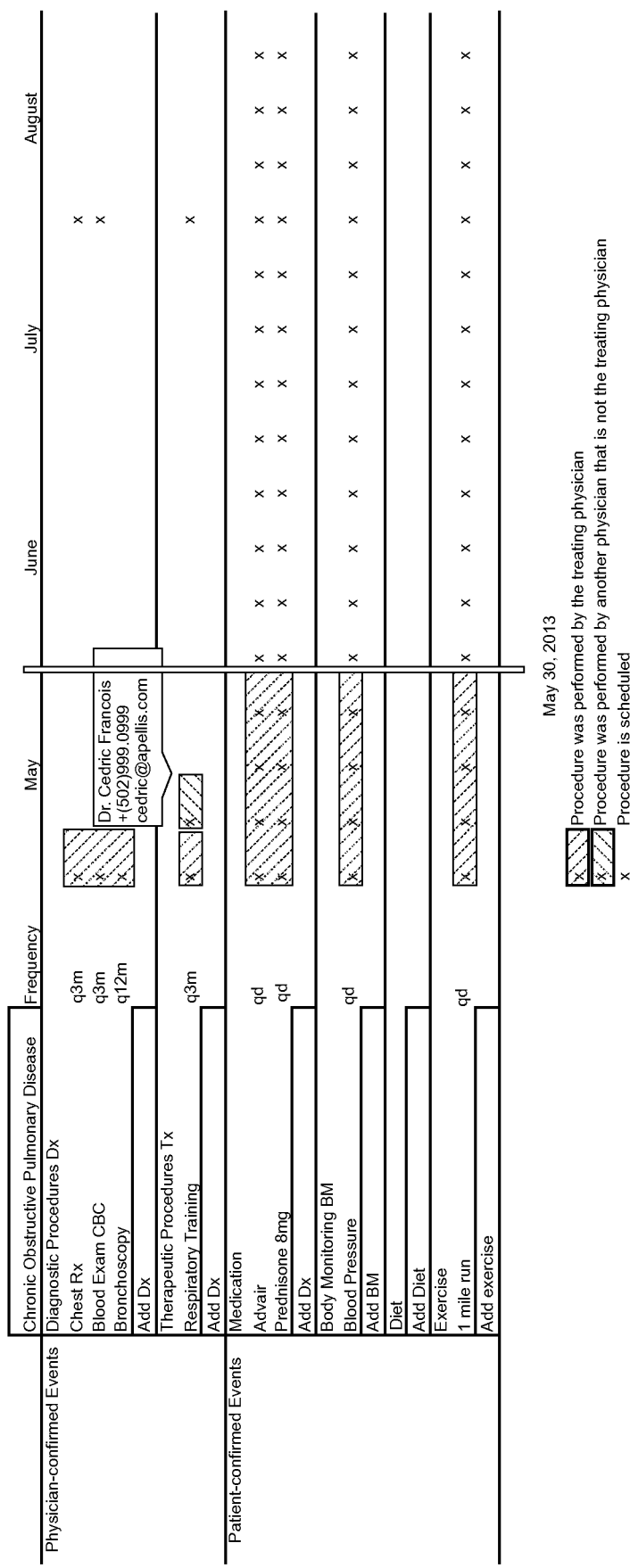
FIG. 7 shows an example of an ADM schedule for use by physicians according to certain embodiments.

In certain embodiments, an ADM schedule on the patient application comprises a schedule of the events that comprise his or her treating physician's treatment plan for that disease. FIG. 7 shows an example of an ADM schedule for use by physicians according to certain embodiments. On the physician application, an ADM schedule for that same patient comprises the same events, i.e., the treating physician's treatment plan and, in addition, those physician events that the treating physician has determined are disease-relevant events for that particular disease (possibly customized by the physician for the particular patient). In certain embodiments the ADM schedule on both the patient and physician applications is updated as confirmation of physician events and patient events is received. The updating need not take place immediately, and the time interval between receipt of confirmation and updating may vary for different events and schedules. Appropriate update response times may be selected to reasonably meet reasonable user expectations. The updating may be different or may have different effects or be displayed or evident in different ways on the patient and physician applications and/or schedules. Through the ADM schedule a physician may thus be informed of (i) the occurrence of disease-relevant events outside the context of his or her treatment of the patient; (ii) the patient's self-reported (or, in some embodiments, device-reported) adherence to the physician's recommendations pertaining to medications, diet, exercise, and/or body monitoring. In some embodiments, in addition to providing information indicating that an event has occurred, the result or data pertaining to the event is added to or available from the ADM schedule. For example, results of patient body monitoring may be entered by the patient or obtained directly from monitoring devices that may interface with the patient device running the application.

In some embodiments patients are notified on an ongoing basis of upcoming scheduled events in any of the aforementioned six categories via a smartphone application or other electronic modes of communication. Patients may thus be assisted in adhering as closely as they choose to their physicians' recommendations. In some embodiments a smart phone application and/or a website is provided through which this physician-patient communication occurs, at least in part. In some embodiments, when a disease-relevant event takes place, it is logged into (stored in) a central ADM for that disease and patient. A central ADM may be accessible over the Internet. It may be at least in part cloud-based and/or may be at least in part accessed through or stored on proprietary servers or data storage media. The central ADM synchronizes with the patient's application and/or patient web pages as well as the physician's application and/or physician web pages.

In certain embodiments a disease-relevant event, e.g., a physician event or a patient event, may be confirmed (verified as having occurred). Confirmation may be utilized in the context of an ADM or portion thereof of any form or structure, e.g., an ADM schedule. In general, confirmation of the occurrence of a physician event is provided directly or indirectly by a physician, e.g., a physician who performs or orders a procedure. Confirmation of physician events may occur in a variety of ways. In some embodiments confirmation that a physician event has taken place is automatic or semi-automatic. In some embodiments physician events are reported to the Revon system and logged into the appropriate ADM automatically when they are performed and billed for (or are otherwise referred to in a financial or administrative transaction, which may be an electronic transaction), e.g., by the treating physician or by other physicians, HCOs, or other entities that provide the relevant health-related service (e.g., clinical laboratories). After a procedure has been performed, a provider (e.g., an HCP or HCO or other individual or entity that provides medical or health services) may submit a bill to a payer or the patient, indicating the procedure(s) performed, for which the payer or patient is requested to pay the provider (sometimes referred to as reimbursing the provider). A submission by a provider to a payer to obtain reimbursement may be referred to as a "claim". A procedure for which payment is sought is typically identified by one or more codes (e.g., procedure codes). In some embodiments when a provider, e.g., a physician, bills a payer or patient electronically or engages in another transaction in which the procedure is referenced (e.g., by procedure code) the Revon system is notified (e.g., Revon system receives at least sufficient information to determine the procedure and patient on whom the procedure was performed). The Revon system may be notified directly by the provider, by an intermediary between the provider and the payer, or by the actual payer. Notification may be facilitated by use of a payer code assigned to the Revon system or to an entity that at least in part owns, controls, or manages the Revon system. An intermediary between the provider and the payer may be, e.g., a claims clearinghouse or other entity that engages in generating, processing, transmitting, and/or analyzing bills or claims. Information sufficient to identify a patient may comprise, e.g., a patient's name, social security number, patient ID, policy number, etc. In general, such information will have been provided to the Revon system, e.g., by the patient, during registration, as described herein. In some embodiments software means are provided that permit a provider or a bill or claim submitter to enter two payer codes for a bill or claim or to supply an electronic copy of a bill or claim to the Revon system. In some embodiments billing/claims information may be entered and/or submitted electronically to a payer and/or to a system of the present invention. In some embodiments bills and/or claims may be prepared at least in part through use of practice management system software, hospital management software, or billing software. In some embodiments billing/claims information may be provided in hard copy form. In some embodiments billing/claims information may be provided to the Revon system by a payer. For example, following receipt of billing/claims information from a provider, a payer may provide at least some such information to the Revon system. Typically the information is provided electronically. In some embodiments practice management software, hospital management software, or claims processing software may be modified or provided with a plug-in that electronically contacts Revon system or searches a database comprising a list of patients enrolled in the Revon system to determine whether a particular bill, claim, or transaction pertains to a patient who is enrolled. If so, the software submits to the Revon system at least sufficient information to identify the patient, the procedure, and the provider who is presenting the bill or claim pertaining to the procedure. In some embodiments a patient may request their physician to notify the Revon system and/or a payer may request or require that the Revon system is notified as a condition for claim eligibility for patients that are registered with the Revon system. In some embodiments payers may provide patients with cards that list a patient ID and/or policy number and, if applicable, indicate that the patient is registered with the Revon system. In some embodiments such software may automatically verify the patient's eligibility for receiving benefits with a payer (e.g., an insurance company) using a standard electronic data interchange connection when a patient makes an appointment or checks in or registers at a physician practice, hospital, or other HCO and may, in parallel or in a similar manner, verify that the patient is registered with the Revon system or check whether the patient is a Revon network member. If so, the software may tag the patient's record so that the Revon system is automatically notified with the physician event-relevant information when the software is used to generate or process a bill or claim pertaining to that patient. In some embodiments the amount of reimbursement or payment requested or paid or other information not necessary to identify the patient, procedure, and provider may be omitted from the information provided to the Revon system. In some embodiments physician confirmation that an event has occurred is achieved by the physician entering confirmation of the event into the Revon system. For example, an HCP who is the treating physician for a particular disease and who performs a procedure in order to treat the patient for that disease may confirm that the procedure has been performed by updating the ADM for that disease and patient. In some embodiments occurrence of an event may be documented in an EMR, e.g., in the normal course of use of the EMR. In some embodiments physician confirmation that an event has occurred is obtained by an ADM accessing or receiving information from an EMR, wherein the information is sufficient to indicate that the event has occurred. In some embodiments a paper copy of a paper-based medical record or paper bill or claim may be obtained and the procedures recorded or billed therein may be entered into the Revon system. In some embodiments the confirmation will be received from the payors, thus allowing population of events on the ADM in a retrospective fashion (e.g. if a Chest X-Ray is an event in a COPD ADM, then past X-rays could be retrieved from the payor's records and used to populate events that have already passed at the time the patient enrolls in the Revon system). ADMs may in some embodiments additionally or alternately be populated retrospectively by extracting data from EMRs.

In general, confirmation of a patient event is provided by the patient, e.g., by interacting with an electronic device. It will be understood that in at least some embodiments a patient event may be performed and/or confirmed with assistance of a patient's family or other caregivers outside a health care setting. Patient confirmation of a patient event may be provided via a patient ADM application, as described herein. For example, events to be performed may be displayed together with a button that the patient can tap to indicate that event has been completed. In some embodiments patient confirmation of an event may be provided to the Revon system directly by a monitoring device or by a different application on the patient's smartphone with which a patient ADM application may interface. In some embodiments, when the Revon system is notified that a procedure was done on a patient it automatically populates the ADM schedule(s) of that patient that contain the procedure in question as a physician event. In some embodiments it is envisioned that the events will populate as having taken place (occurred), where, when and by whom, at least to the extent such information is ascertainable from the information provided to the Revon system. For example, patients may have a pill dispenser that synchronizes with the ADM and provides color-coded notifications when certain pills need to be taken (e.g. a dispenser would be "green" when a pill can be taken; "yellow" when time is elapsing, and "red" when the pill cannot be taken). When the pill is taken the events is confirmed and logged in the ADM. In some embodiments physicians with access to the ADM will be able to view at least some patient events, e.g., those patient events specified by that physician, and may be able to follow patient adherence to the physician's recommendations, at least to the extent that the patient accurately reports patient events. In some aspects, an ADM schedule is populated via inputs from diverse sources, which may include one or more physicians that performed a procedure on the patient, one or more payers, and the patient.

In some embodiments, by, e.g., clicking on the events, physicians will be able to see results of the procedures as well. The ability to see results may vary depending on the particular procedure and/or the systems being used by the performing physician or HCO. The system may evolve over time to provide physicians with increased access to results. In some embodiments patients may control which of their physicians are permitted to view their ADMs and/or gain access to results of procedures or other data. For example, patients may make such a selection using a patient application. In some embodiments patients are able, through a smartphone application (or other device application) to record (log) their compliance with their physicians' recommendations in the management of their disease as it relates to any one or more of the following: medication, body monitoring, diet, and/or exercise. Patient-confirmed events will also populate the relevant sections of an ADM schedule. In some embodiments results may be included as well, at least for certain patient events. ADM screens may include functionality that allows a user to zoom in/out and/or magnify or expand or shrink the view.

As discussed above, in some embodiments, an ADM comprises a disease-specific schedule, which is specified by the treating physician of the disease. In some embodiments physicians are able to create or select an ADM template (the physician's preferred ADM or "schedule" for a disease) that may apply generically to all the patients under their care with that particular disease, but which can be modified for each patient individually. Only the treating physician can modify the set of events and timing of an ADM schedule of a disease for his or her patients. However, physician events on the ADM schedule are recorded regardless of which physician performs them (the treating physician or other physicians). In some embodiments, color codes or other indicators on the ADM schedule indicate whether such events took place, and, in some embodiments, information indicating which physician performed the procedures in question is accessible. New physician events and/or patient events can be added from libraries of events and the frequency of occurrence of these events can be set/changed by the treating physician (schedule template creation is discussed further below). In certain embodiments there are two main categories of events: physician events and patient events (patient events may sometimes be referred to as My Events, e.g., in the context of a patient application, discussed elsewhere herein).

In some embodiments physician events are associated with at least two functionalities, i.e., (1) Patient notification of upcoming physician events and (2) Confirmation of physician events. In regard to patient notification of upcoming physician event(s), patients will be able to be in constant communication with their ADM schedule via a smart phone application and/or patient web portal. At least the physician event that is due to take place next on a patient's schedule will appear prominently on the home screen of the smart phone application/patient web page. If this event is due to take place further than a predetermined time in the future (e.g., three months in the future), the event will appear in green color. When the event is due within the next three months (90 days) the upcoming event will appear in a yellow/orange color. When the event is overdue and has passed the 90 day time window, it will appear in red. By clicking on the event or an appropriate button, the patient is able to schedule appointments that are coming due and/or confirm dates for appointments that have actually been scheduled (in the latter case, for example, a schedule entry that indicates that an appointment is due may be changed to indicate an actual appointment, e.g., on a specific date with a specific time). Physician events may only disappear from the patient schedule when they are confirmed by a physician as having been done but in some embodiments may disappear from the home screen after a specified time period, which may be predetermined by the system or set by a user, or may be deleted from the home screen by the user. In some embodiment physician events that are not confirmed may remain visible on the home screen at least to the extent space is available. In certain embodiments patient events consist of Medication, Body Monitoring, Diet and Exercise. In some embodiments patient events are associated with at least two functionalities, (1) Patient notification of upcoming event and (2) Confirmation of patient event. In regard to patient notification of upcoming event, the patient event that is due to take place next on a patient's schedule may appear prominently on the home screen of the smart phone application/web page. If this event is scheduled to take place further than three hours in the future, the event may appear in green. When the event is due within the next three hours the upcoming event will appear in yellow/orange. When the event is overdue and has passed the three hour time window, it will appear in red for an additional 3 hours. Unlike physician events, three hours after having passed into "red" patient events will disappear from the patient's schedule (at least under My Events) and no longer be able to be confirmed. Unconfirmed patient events that have passed the "red" time window may in some embodiments remain viewable on the patient's schedule, e.g., when scrolled to view past events but can no longer be confirmed. A patient event may be confirmed by the patient accessing the patient smart phone application/web portal and clicking on the event. Under certain circumstances the confirmation might be more elaborate and might involve data input. It should be understood that the system is not intended to generate a perfect record of patient events, but rather a reasonable reflection of the patient's compliance with their physicians' recommendations. Virtual awards/accolades may be created to incentivize patient compliance. It will be understood that details such as colors, time intervals, etc., are merely exemplary and non-limiting. A time interval may be predetermined by, e.g., the Revon system, the treating physician, and the time interval may differ for different patient events.

Schedules may be used and updated on an ongoing basis for any time period or indefinitely. In some embodiments a schedule may continue to be updated as long as the patient has at least one treating physician who is a Revon network member. In some embodiments a schedule is used or updated over a period of at least 3, 6, 12, 18, 24 months, or more, e.g., between 3, 6, 12, 18, or 24 months and 20 years.

In some aspects, a physician or patient who completes a registration process is considered a member of a Revon network. A physician may be a member of a Revon physician network. A patient may be a member of a Revon patient network. Members of a Revon network are able to use the Revon system and its various device applications and website for physicians and patients as described herein. In certain embodiments membership in a Revon network includes various social media functions (e.g., as described elsewhere herein, that allow patients to communicate with other patients, allow physicians to communicate with other physicians, and/or allow patients and physicians to communicate with each other). In some embodiments patients who have a disease may become members of a disease network relating to that disease, which network may comprise patients who have the disease and physicians who treat the disease. Membership in a particular disease network may mean that a patient's identifying information is stored by the system in association with information identifying the particular disease, and in some embodiments, an ADM for that disease has been created for the patient. Patients may become members of a disease network in a variety of ways. In some embodiments patients with a particular disease are offered an opportunity (invited) by their physician to become members of the disease network for the particular disease. Membership may happen automatically when a patient registered in the Revon system has a physician-confirmed diagnosis entered into the Revon system. In some embodiments, only patients confirmed by their physician as having a disease are permitted to become members of the disease network for that disease. In some embodiments, a physician who invites the patient to join the disease network and confirms that the patient has the disease is the treating physician for that disease. In some embodiments creation of an ADM for a patient by a physician or a physician's designee upon the direction of the physician serves as confirmation that the patient has the disease. In some embodiments patients who are members of a disease network are provided with means to communicate with other patients who are physician-confirmed as having that disease. In some embodiments patients who are members of a disease network are provided with means to identify and, in some embodiments, contact, network member physicians that treat the particular disease. In some embodiments patients who are members of a disease network receive real-time guidance from their schedule, which reflects the recommendations by their treating physician. This guidance may comprise, for example, office visit reminders, medication reminders, diet recommendations, exercise recommendations, body monitoring recommendation. In some embodiments the Revon system monitors patient compliance with physician recommendations and reminds patients of the recommended follow-up with their physician. These functionalities may translate into an improved relationship between physician and patient and an improvement in disease management and general outcome.

An ADM schedule may serve as a communication tool between physician and patient and/or between different physicians who treat the patient. In some embodiments the schedule and/or an application that comprises an ADM schedule engages the patient, e.g., by informing the patient of his or her physician's recommendations including, in some embodiments, recommendations for treatment and diagnostic procedures to be performed by physicians and recommendations for patient self-management activities, e.g., as described further below. In some embodiments a system, e.g., through an ADM schedule, allows a physician to follow, in a disease-specific fashion, the occurrence of selected disease-relevant events that are associated with the patient (e.g., procedures performed on the patient), regardless of who performs the events and/or who contributes events to the schedule (e.g., the treating physician, other physicians, or the patients themselves). In some embodiments a system allows a physician, through an ADM schedule, to be informed of the occurrence of disease-relevant events by accessing an ADM schedule and/or by receiving notifications via means such as email or text message. Such information may permit the physician to, e.g., assess patient adherence to recommendations and become aware of disease-relevant events that occurred between visits without needing to question the patient. Physicians may use the schedule, e.g., to review disease-relevant events in advance of a patient visit, which may permit more effective use of time spent with the patient. In some embodiments the system allows a physician, through an ADM schedule, to access data associated with a disease-relevant event (e.g., results of a diagnostic procedure, results of patient self-monitoring). In some embodiments a physician is able to access data pertaining to procedures performed on the patient by different physicians and/or at different HCOs. In some aspects, an ADM system may provide means to reduce unnecessary procedures and/or improve patient adherence to physician recommendations. Physicians will be able to rapidly know whether procedures relevant to the disease they are treating were performed on a patient, when (or approximately when), and will be provided with sufficient information to permit determining which HCP performed or ordered the procedure and/or where the procedure was performed or where results were reported. It is expected that this information will allow physicians to reduce duplication by requesting (e.g., by email, phone, fax, or other means) a copy of results or reports and/or relevant portions of the patient's medical record at the HCO where the procedure was performed or ordered. In some embodiments data resulting from such procedures will be accessible via the system. Avoiding unnecessary repetition of procedures reduces patient risk that may be associated with such procedures as well as reducing expense. Obtaining results of a procedure that has already been performed may provide a physician with the information he or she needs to make a treatment decision more rapidly than would be the case if the physician needed to wait until the procedure could be scheduled and performed. The system may assist patients to be actively engaged in the management of their disease on a variety of levels, such as timely follow-up with their physicians, proper adherence to medication, and monitoring patient-monitorable physiological parameters.

In some embodiments patients may be compared to their fellow patients (e.g., all patients in the network or patients in the network who have the same disease) and ranked for compliance with their physicians' recommendations, e.g., using a percentile system. In some embodiments patients may be stratified, e.g., according to the severity of their disease and/or the complexity of their physician's recommendations so that, for example, patients who have a complicated medication regimen are not compared with patients who have a much simpler medication regimen. Patients may be informed of their ranking on an overall or disease-specific basis. Awards may be provided to incentivize patients to comply with their physicians' recommendations (e.g. award for an achievement such as taking all medications on time for seven straight days). An award may be virtual or actual. Virtual awards are described further below in context of "My Achievements" function of a patient application. An actual award may, for example, be offered by a payer or health care plan, or employer that at least in part pays for or provides a patient's insurance coverage or health care. In some embodiments patients are able, through a patient application or patient website, to learn of clinical trials that are offered in their geographic location, and may be invited by sponsors to participate in trials that match their disease profiles. In certain embodiments at least some of these features do not require disclosure of patient identifying information. In some embodiments an ADM schedule provides a mechanism to evaluate a patient in terms of their compliance with their schedule. In some embodiments patients may be assigned a score based at least in part on such compliance. Such a score may be useful, e.g., to sponsors of clinical trials, which may prefer to enroll patients who are deemed likely to comply with the requirements of the trial and/or for payers, as it allows them to reward good patient behavior and reduce costs associated with poor compliance.

Figure 5A:
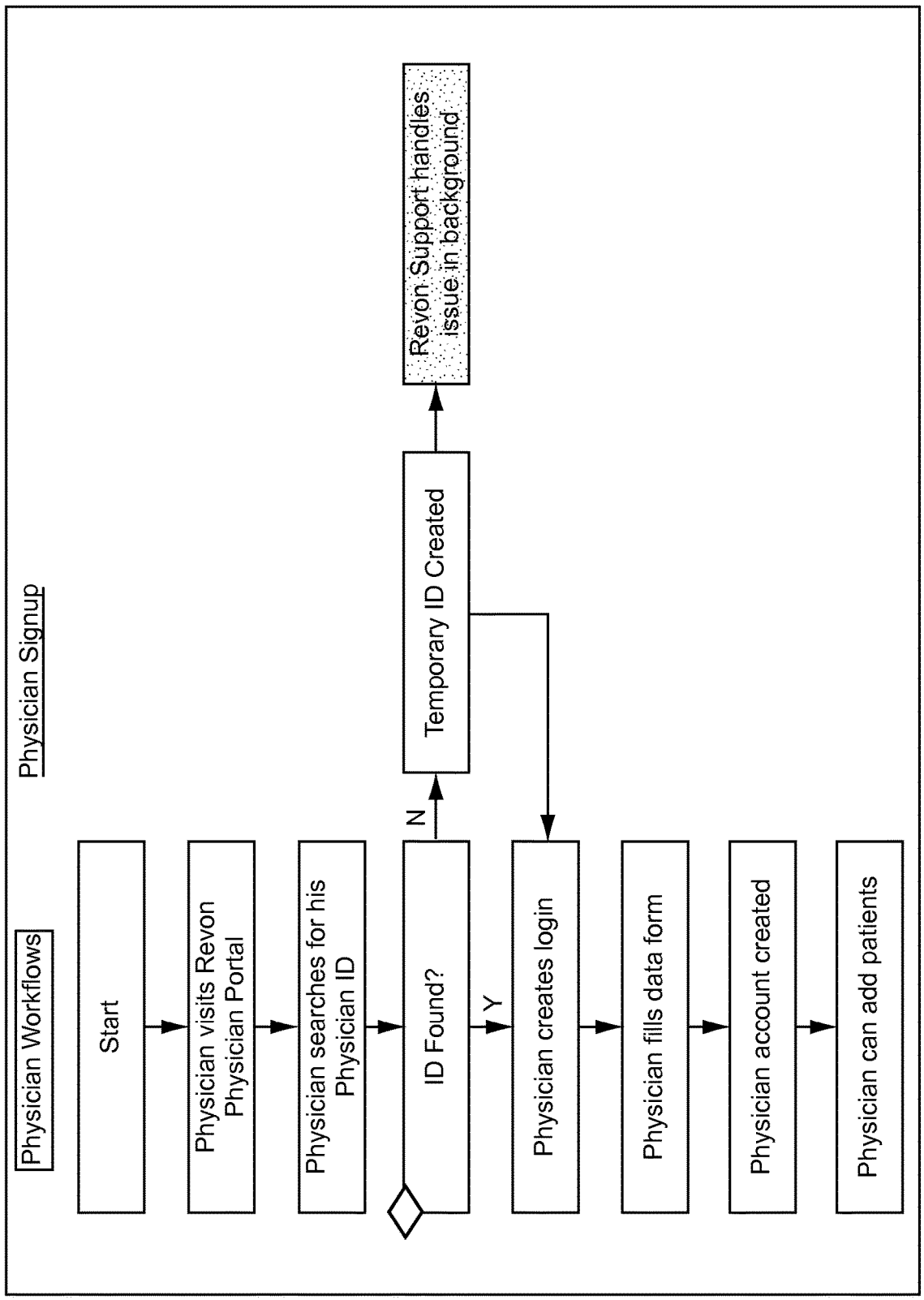
FIGS. 5A and 5B show various physician workflows according to certain embodiments.
Figure 5B:
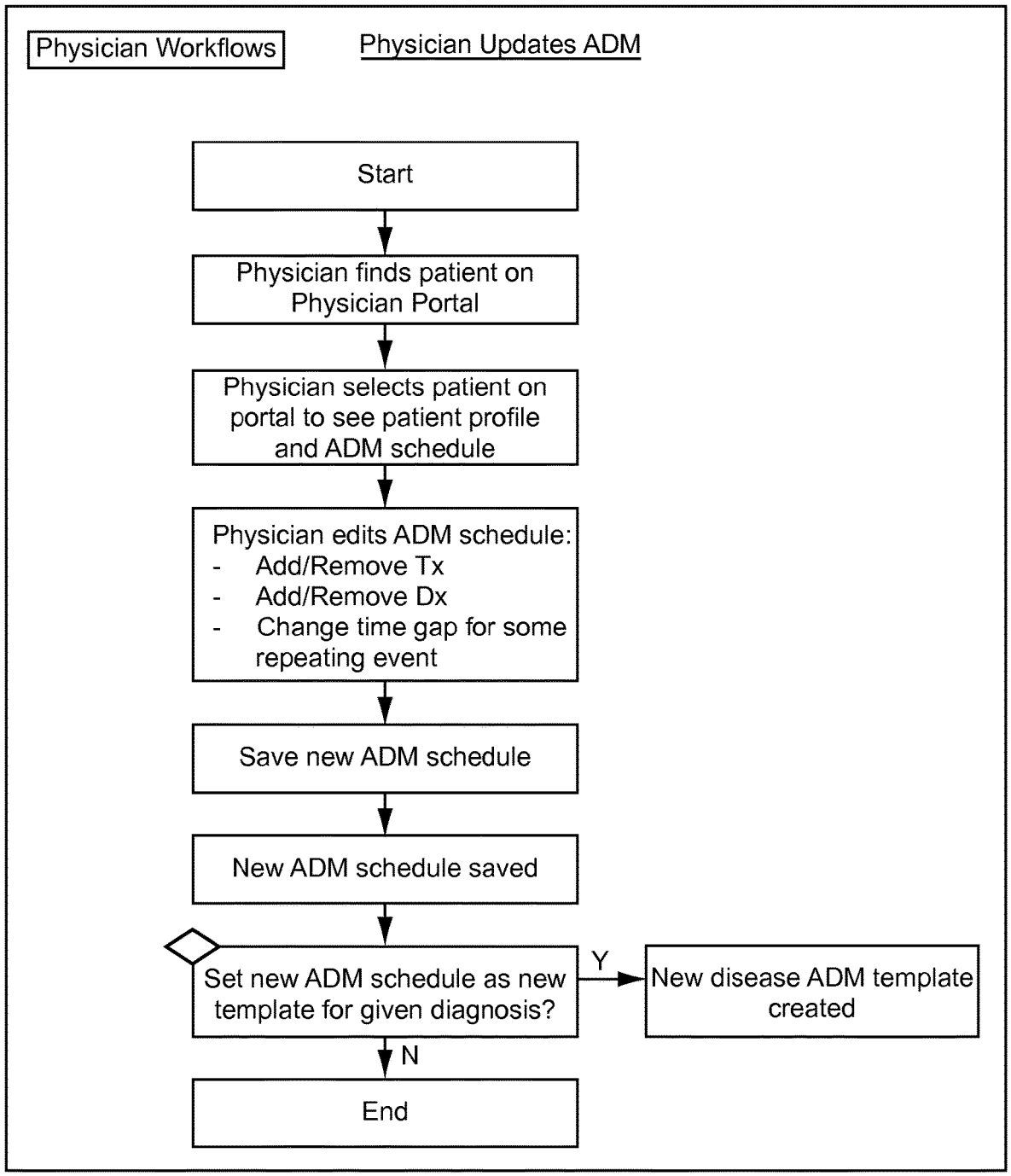

A physician may enroll (register) with the Revon system at any time by visiting the Revon physician web portal. In some embodiments a patient will be able to enroll in the Revon system under any of at least four different circumstances. Examples of typical enrollment (registration) processes are described below. Certain workflows associated with physician and patient enrollment are shown in FIGS. 5A and 5B. It will be understood that these processes and implementations may vary.

(1) New Patient visits New Physician (neither is registered with Revon system): In this situation, the patient or the physician (or both) is aware of the Revon system/network and would like to participate (or at least are willing to participate). First, the physician would establish his/her initial Revon system web page through the Revon system. This process may be as simple as accessing the Revon system website (e.g., Revon physician portal) and registering as a physician. In some embodiments a physician may enter his name and the system may search for the physician's ID. If not found, physician may be asked to register. This will result (e.g., assuming that the physician is appropriately verified) in a web page for the physician, on which patients can be enrolled by the physician. Enrolling a new patient may be as simple as logging his/her social security number (SSN). The Revon system should not recognize the SSN since the patient is not already enrolled and will request the basic information on the patient as well as an email address and the confirmed diagnosis of the patient, which may be selected from a menu (e.g., a scroll-down menu), but might alternately or additionally be entered as text by the physician, e.g., if the diagnosis is not listed in the menu. As a consequence of this action the patient receives an email notification with a download for the smart phone application or link to the patient web portal that will make him/her a member of the disease network for that disease. The first time the patient logs on, he/she will be asked for basic information (log-in, password, basic settings), as well as certain health information. The latter may be virtually identical to the health information physicians typically ask patients to fill out prior to or at an initial visit. On the Revon system this information needs to be filled out only once. In some embodiments, instead of asking the patient to enter the health information, the Revon system may acquire the information by other means. For example, if the patient completed a paper form when visiting the physician, the physician or administrator may enter the data into the system, or an appropriately authorized individual, e.g., an administrator of the Revon system may enter the data. If the patient has an EMR with the physician, the Revon system may obtain the information from the EMR or it may be entered by the administrator from the EMR. In some embodiments, patient registration requests information about a patient's medical insurer, e.g., the name or his or her insurer, his or her policy number, and/or any patient ID assigned by an insurer. In some embodiments such information may be used by the Revon system, e.g., in order to capture HCP confirmation that physician events have occurred, as described herein. Once the patient is registered he/she will be able to access the functions of the Revon system (e.g., finding physicians and/or patient friends) and may be provided with a default patient ADM schedule for his or her disease. The physician receives a corresponding default physician ADM schedule and is able to customize the ADM schedule to become his or her standard ADM template for that disease or adapt it to the patient in question (after which the patient's ADM schedule is modified accordingly). In some embodiments the physician is provided with the default schedule first (i.e., before a schedule is provided to the patient) to afford the physician an opportunity to review and/or modify it.

(2) New Patient (i.e., patient not registered with Revon system) visits a Revon Physician (i.e., physician already registered with Revon system): In this case the physician is typically accustomed to using the Revon system. The patient may meet with an administrator after receiving a confirmed diagnosis (the physician may convey the diagnosis to the administrator). The administrator enrolls the patient in the Revon system, and the patient will automatically receive the physician's ADM template for the relevant disease and is a member of the Revon patient network. The administrator may explain features of the patient registration process and/or patient application to the patient or may assist the patient with registration and/or initial access to the patient application. The physician can customize the ADM further for the particular patient, e.g., to meet the patient's individual needs.

(3) Revon Patient (i.e., patient who is registered with Revon system) visits New Physician (i.e., physician not registered with Revon system): In this case it is assumed that the patient has an existing ADM for a disease and is either seeking to change their treating physician for that disease (referred to below for convenience as scenario 3A) or the patient has a new disease that will require adding a new ADM for this condition (referred to below for convenience as scenario 3B). In the case of (3A) (Change Treating Physician): at the request of the patient a new physician could register with the Revon system and access the ADM of a patient. In some embodiments the patient may need to authorize a change in treating physician, e.g., via the patient application or from the Revon system patient web portal, in order for the change to be effective and for the new physician to be able to modify the ADM. When the physician modifies the schedule of the ADM he/she automatically becomes the treating physician of the disease. The previous physician will continue to be associated with the events that he/she performed, as will any physicians that have performed events associated with the ADM. In the case of (3B) (Add New ADM): When a Revon patient with an ADM (for this purpose "ADM1") is afflicted by a new condition and sees a physician that is not registered with the Revon system, then (i) That physician may choose not to register with the Revon system. In that case ADM1 would still populate with physician events performed or ordered by the physician in connection with the patient visit, but only if they happen to coincide with diagnostic or therapeutic procedures in ADM1 (i.e., they are disease-relevant events for ADM1), or (ii) The physician registers with the Revon system and creates a new ADM (ADM2) for the patient's new disease and creates a schedule for the patient, thus becoming the treating physician for ADM2 (in this case ADM1 will also populate with disease-relevant events, if any, for ADM1). As noted above, in some embodiments the patient may need to authorize a change in treating physician.

(4) Revon Patient with new disease visits Revon Physician: In this case both patient and physician will have registered with the Revon system, and registration information for both will be in the database. The physician determines that a patient has a particular disease and adds an ADM for that disease. The patient will receive the ADM schedule that the physician likes to use to manage that disease. The physician may customize the schedule based on the individual patient.

Figure 6A:
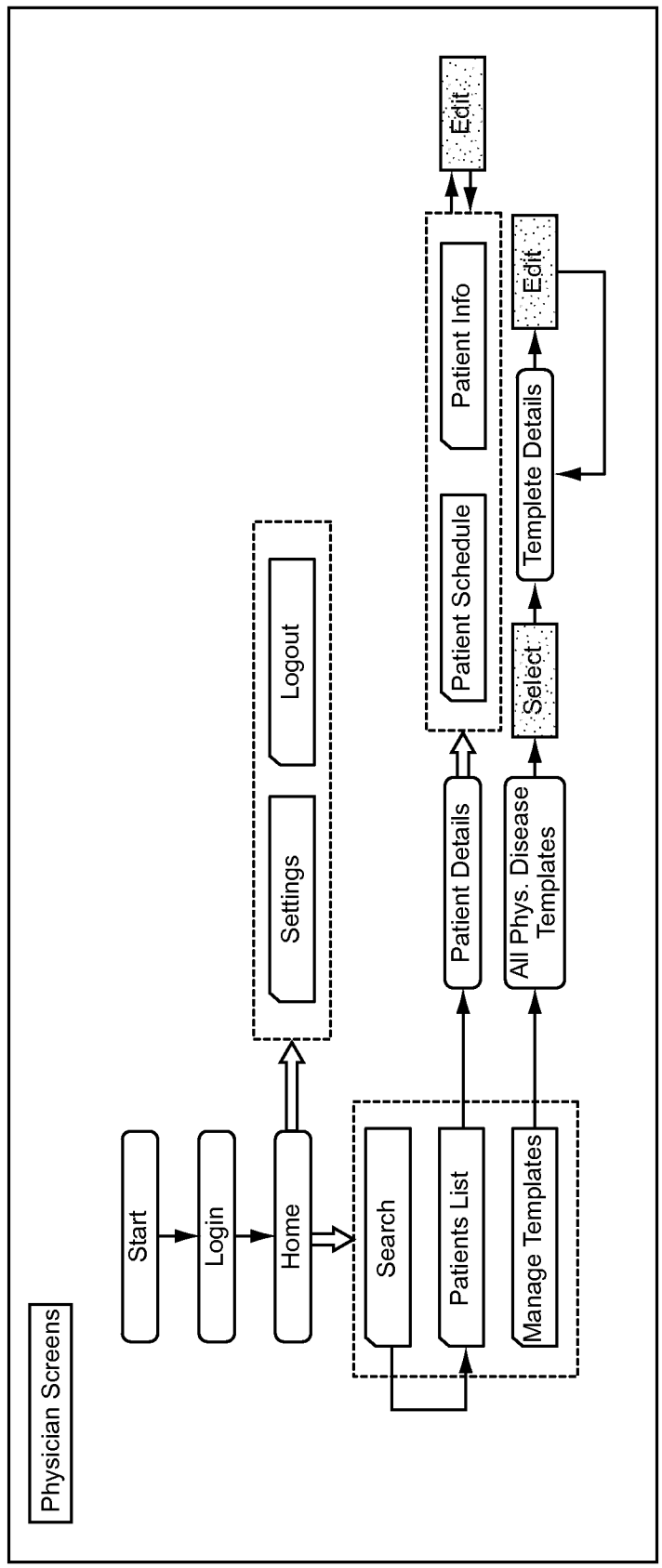
Figure 6C:
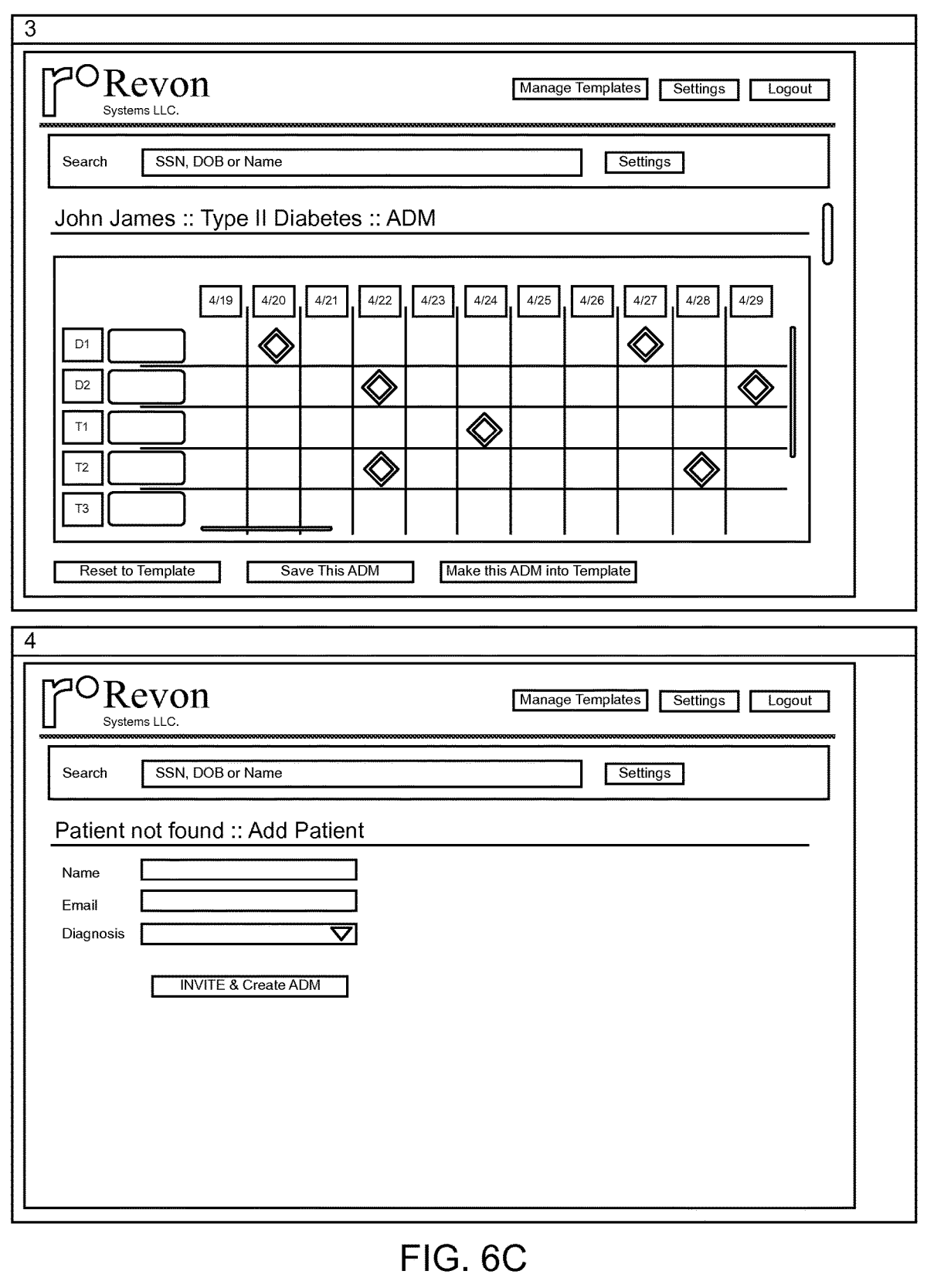

FIG. 6A shows a physician screen flow, and FIGS. 6B-6D show screens for HCPs, e.g., physicians, and HCP-associated individuals (e.g., admininstrators in a physician's office) who use the Revon system in certain embodiments. For purposes of description such individuals here will be referred to as "user". It is assumed in these figures that these screens are on a desktop, notebook, or laptop computer, or tablet device and displayed within a browser, although they could be provided as an application and/or viewed on a smartphone via a browser or application. When the user logs in, he or she sees the Home screen shown here in screen 1. The screen contains three buttons at top right, a search panel below and a table below that. The first button at top right—Manage Templates, allows the user to see and edit all his or her ADM Templates. The second button—Settings, allows the user to edit his or her settings. The third button—Logout, logs him out of the website. The search panel allows the user to search for any patient by his Social Security Number, by his Date of Birth and by his Name. The table shows all the patients of the physician who are on the system with their high level details. The user can click on any of the rows to get more details about the patient. When the user clicks a row in the table of screen 1, he reaches screen 2. Here more details about any single patient are displayed. The user can see the patient's profile data, prior visits, upcoming visits (as per the ADM), the ADMs under this physician's management for this patient, and the patient's other ADMs that the patient has made visible. Also, the user can add a New ADM, send an email, or make a call to the patient from within this screen. If the user clicks an ADM on screen 2, the user can see on screen 3 the scheduled physician events for the patient under that ADM. On screen 3, D and T stand for diagnostic and therapeutic procedures respectively. In an actual ADM, the names of the procedures may be indicated. In addition to the elements shown on screen 3, a frequency is typically listed beside each D and T (unless it is a 1-time or irregular event), which the user can change. The user can then edit this ADM and save it. The user can make this ADM into an ADM schedule template for this disease (e.g., for the physician event portion of an ADM) or reset the ADM to the ADM schedule template for this disease. The user may be asked whether he or she wishes to use the modified ADM as his or her default template for future patients, apply it to current patients, or both, and the system may take the requested action depending on the response. Additional screens (not shown) would provide a schedule for patient events, which the user can also edit, save, and/or make part of an ADM template for this disease. If the user searches for a patient on screen 1 and cannot find him, the user can add him in screen 4. This screen will create a new ADM for the patient and also invite him to join Revon. The user enters the patient name, his email, and the diagnosis from the physician visit. Once the green button is clicked, an account is created for the patient in the Revon system. The patient will also receive an email link to activate his account, following which the patient will go to the Revon system website and complete a registration form and will then get an active account and then download the patient application (e.g., on his or her smartphone). Alternately, the patient may directly download the application and complete the registration form within the app to obtain his active account. When the user clicks the Manage Templates button at top right of screen 4, the display goes to screen 5. Here the user can see all his or her current templates with details about them. The user can click any row to open the ADM template and edit it if desired. On screen 5 when the user clicks the Settings button at the top right, he goes to screen 6. Here the user can update his settings as shown in the screen.

In some embodiments a patient may access an ADM schedule via a patient application. In some embodiments a patient application (e.g., a smartphone application) allows a patient to access one or more categories of health-related content, e.g., health-related information, wherein the health-related content in each category is consolidated (aggregated, combined) across one or more diseases for which a patient is under or has been under medical care. In some embodiments the application also allows the patient to access at least some of the same content, organized in the same categories, but on a disease-specific basis, for one or more diseases for which the patient is or has been under medical care. For example, there may be between 2 and 10 different categories. A first screen may display the various categories and, in some embodiments, one or more items of information in at least some of the categories. If a patient who is under medical care for three different diseases selects a particular category from the first screen, the patient is presented with content, e.g., information, in that category, consolidated across all three diseases. If the patient swipes across the screen (horizontally) disease-specific screens are presented for each disease. If a disease-specific screen is accessed from the first screen, the same categories are displayed for each disease as on the first screen, but only information pertaining to the particular disease is accessible from the disease-specific screens. If a disease-specific screen is accessed from a category-specific screen, only content in that category and information pertaining to the particular disease is displayed or accessible. In some embodiments at least some categories correspond to functions available in a patient application. For example, in some embodiments a patient application comprises a screen that provides a consolidated view of, and access to, at least some of the main functions of the application. This screen is typically the first screen that the patient sees upon accessing the application during ordinary use (assuming that the patient is already registered with the system) and may be referred to as a "home screen", "main screen", or "start screen". In some embodiments the format of the disease-specific screens and categories of content available therefrom are generally uniform across diseases. For example, the appearance and order of function names or icons, and the overall layout of the screens may be the same regardless of the particular disease. In some embodiments a disease-specific screen for a disease provides access to at least some of the same functions as are available from the home screen, wherein at least some of the functions provide access to content pertaining to that particular disease. For example, in some embodiments a schedule function for a disease provides a schedule consisting of events relevant to that disease; a My Physicians function for a disease provides a list of the patient's physicians who are at least in part responsible for managing that disease; a My Friends function for a disease provides a list of the patient's patient friends who have the disease; a My Achievements function provides a list of the patient's Achievements in terms of patient events relevant to that disease, etc.

Figure 2A:
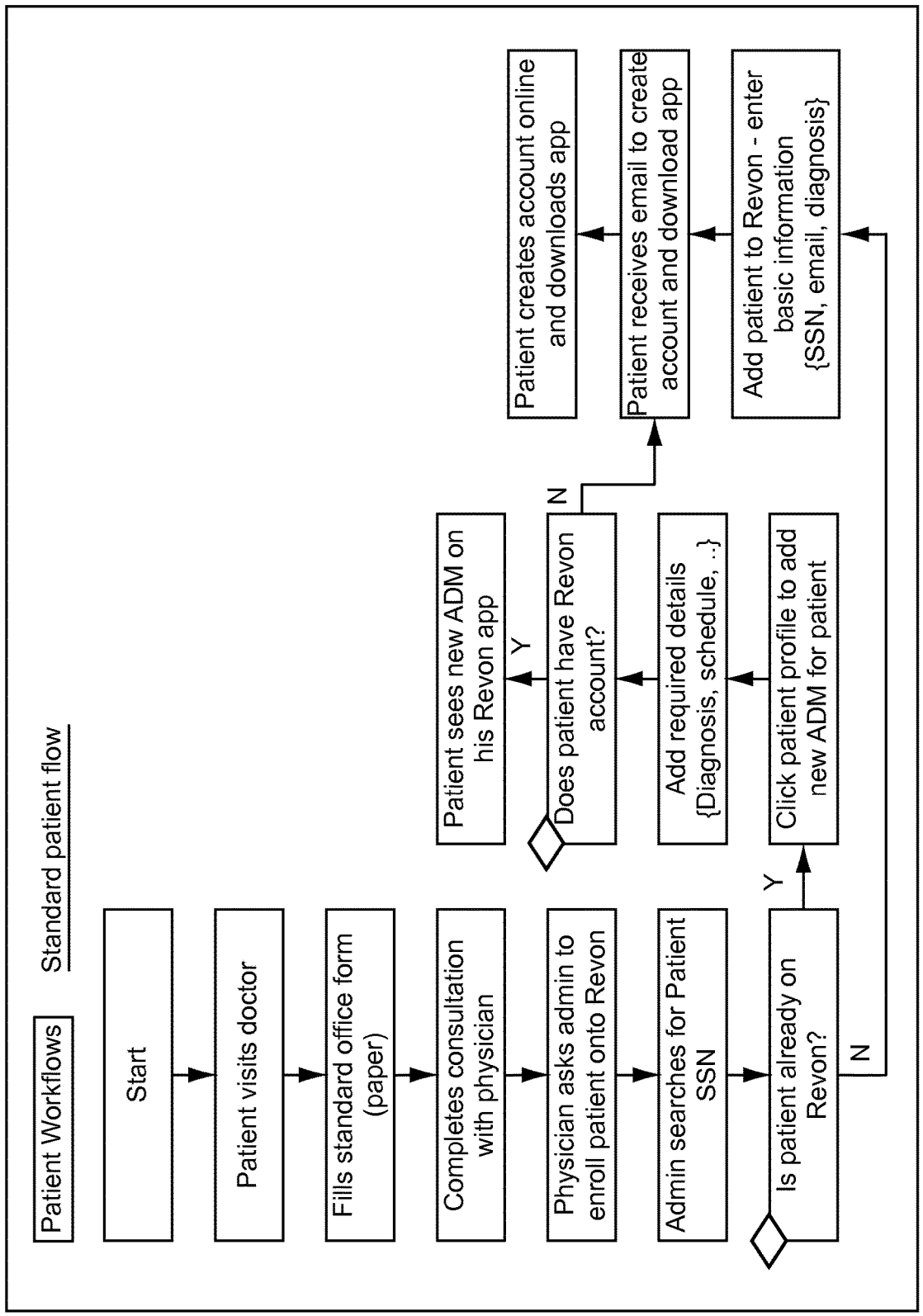
FIGS. 2A-2D show various patient-related workflows in accordance with certain embodiments.
Figure 2B:
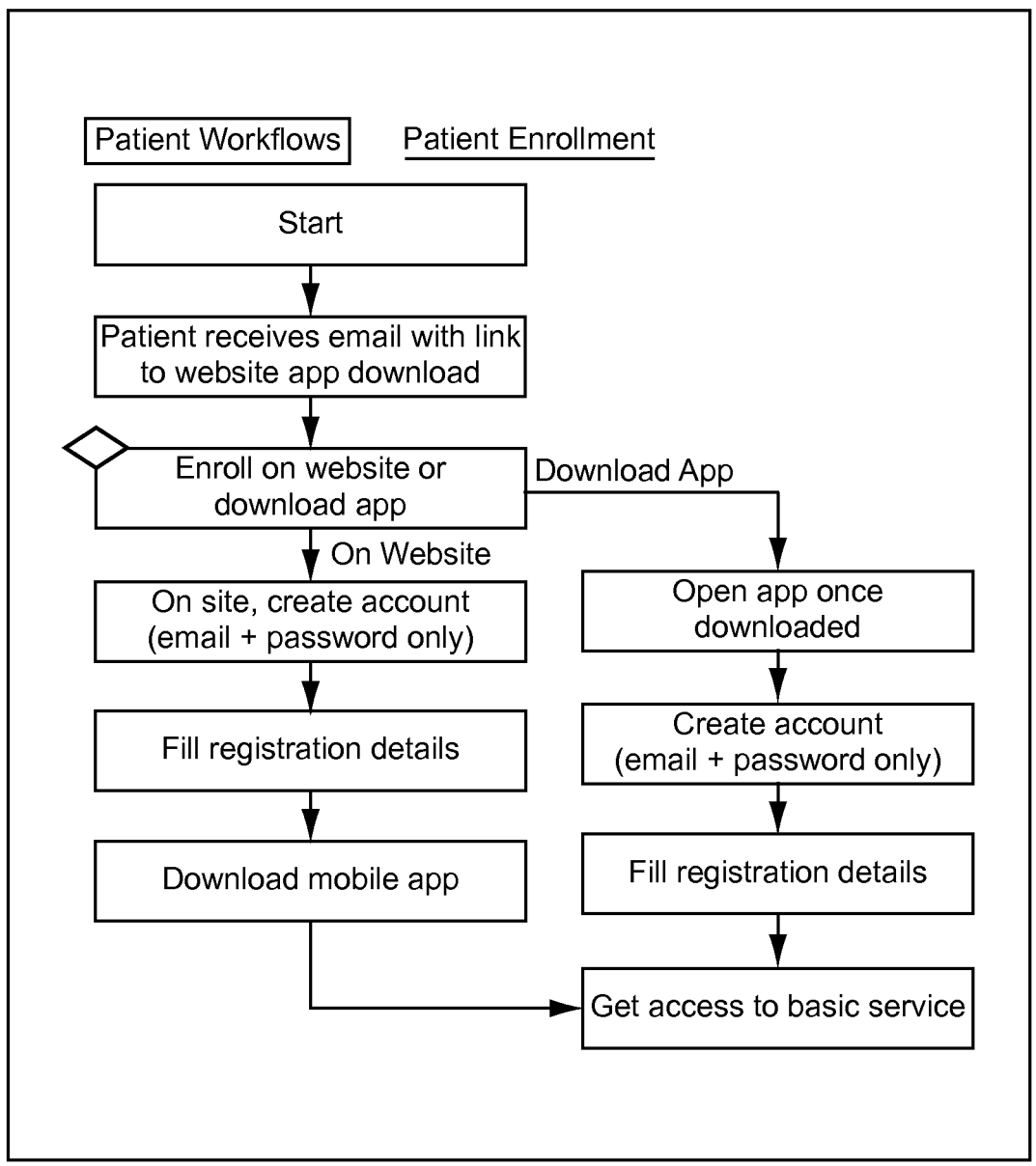
Figure 2C:
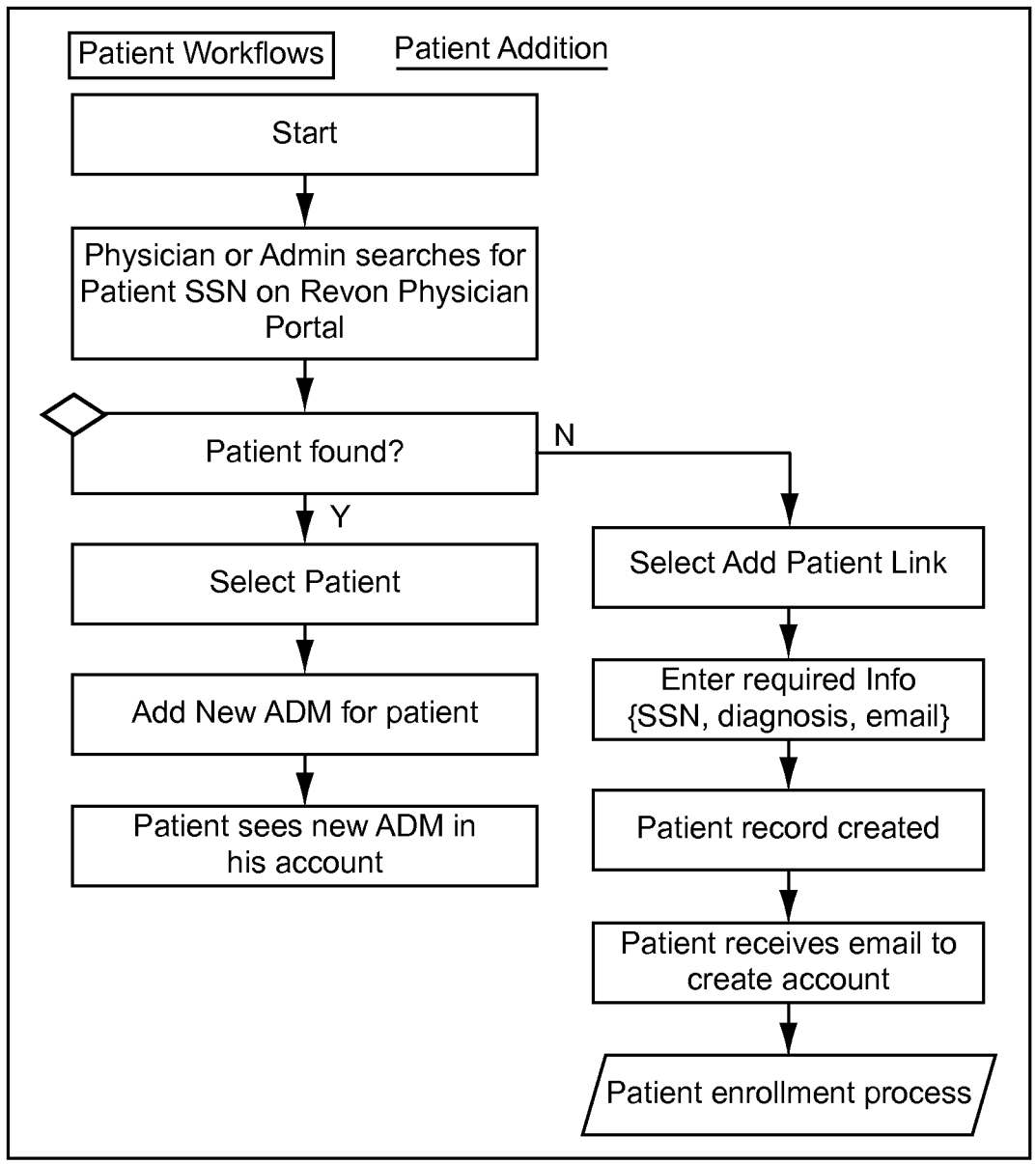
Figure 2D:
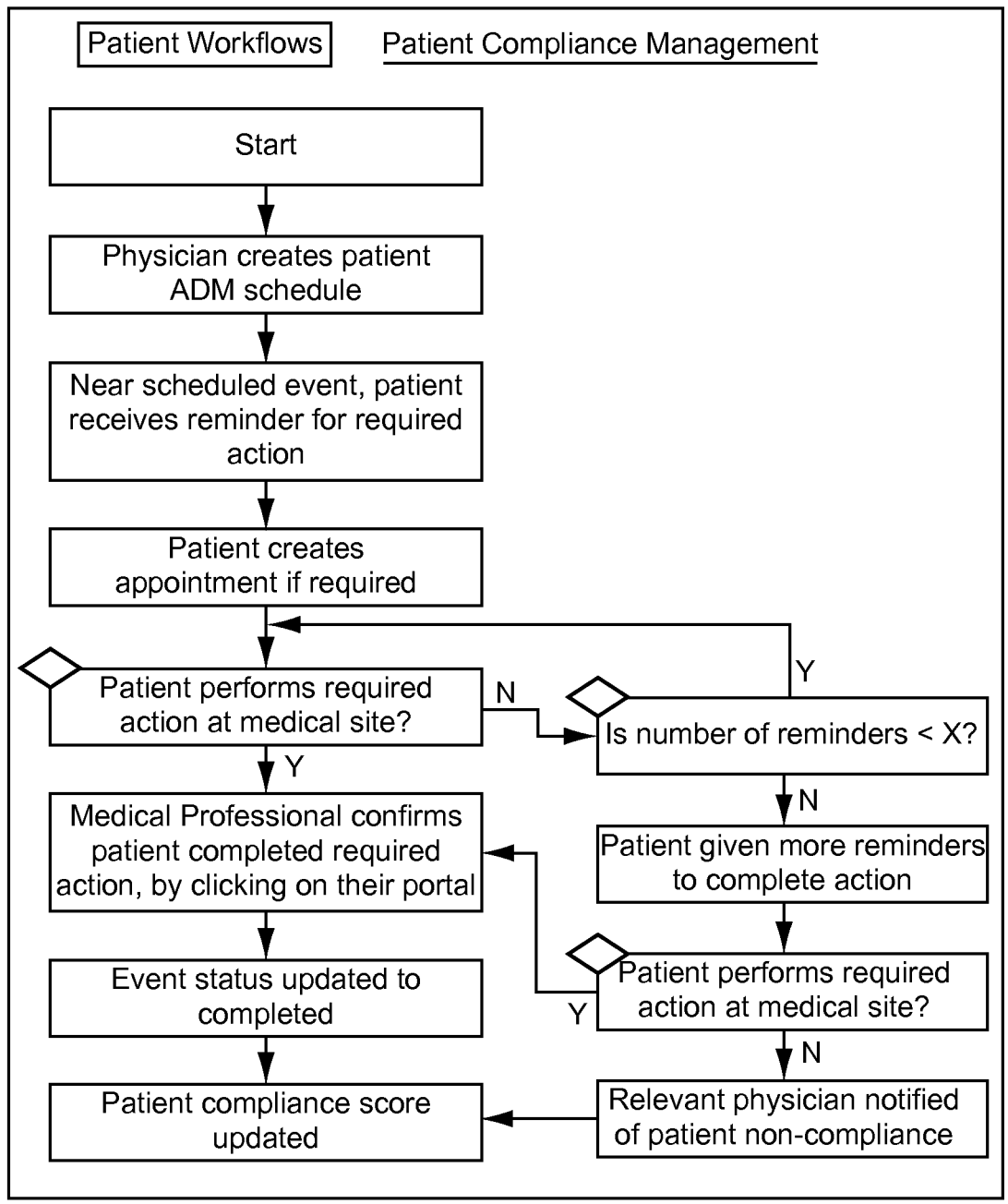

FIGS. 2A-3D show exemplary patient-related workflows in accordance with certain embodiments. FIG. 2A shows a standard patient workflow. FIG. 2B shows a patient enrollment workflow. FIG. 2C shows a patient addition workflow. FIG. 2D shows a patient compliance management workflow.

Figure 3A:
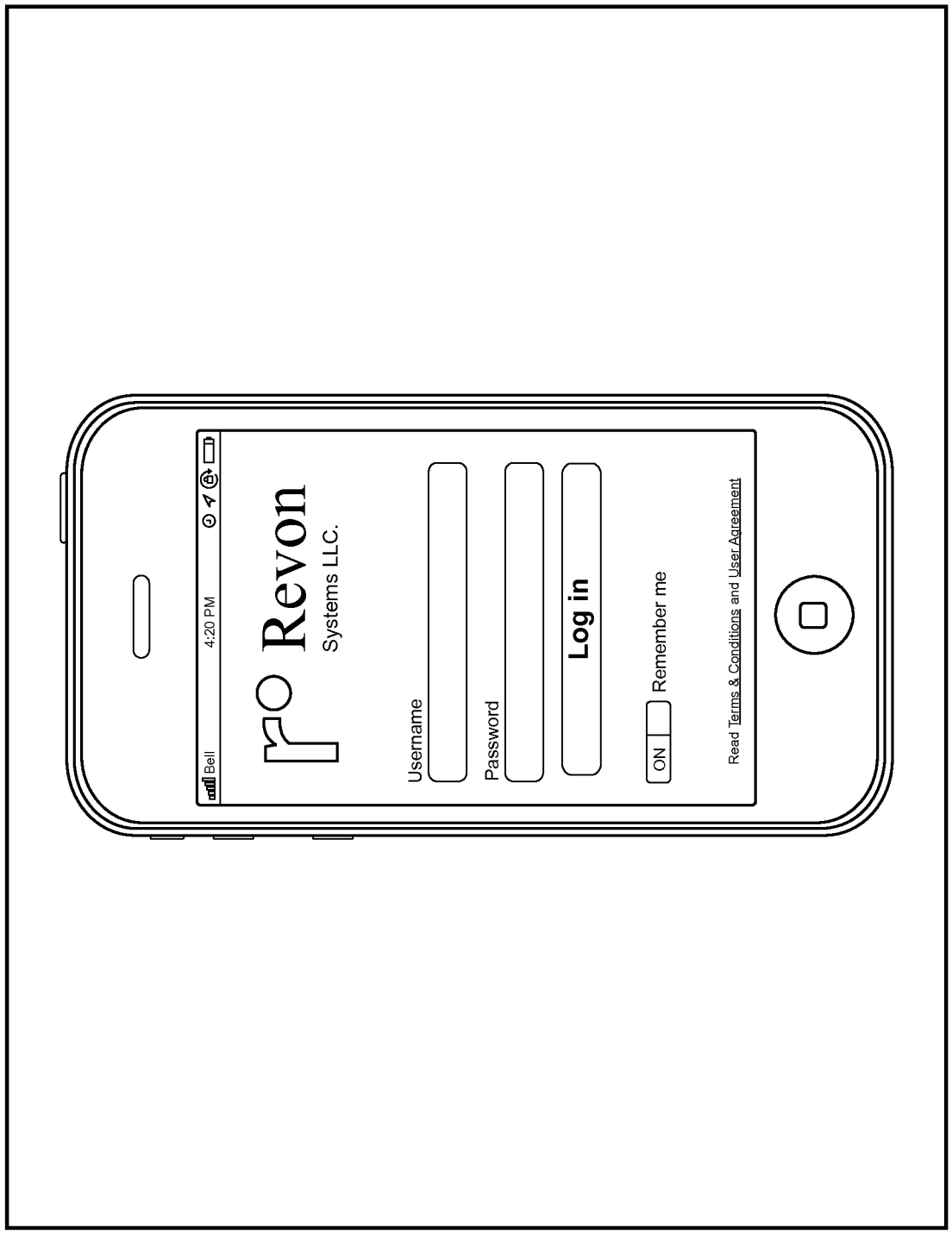
FIGS. 3A-3P show various screens of a smartphone equipped with a patient application (app) according to certain embodiments.
Figure 3B:
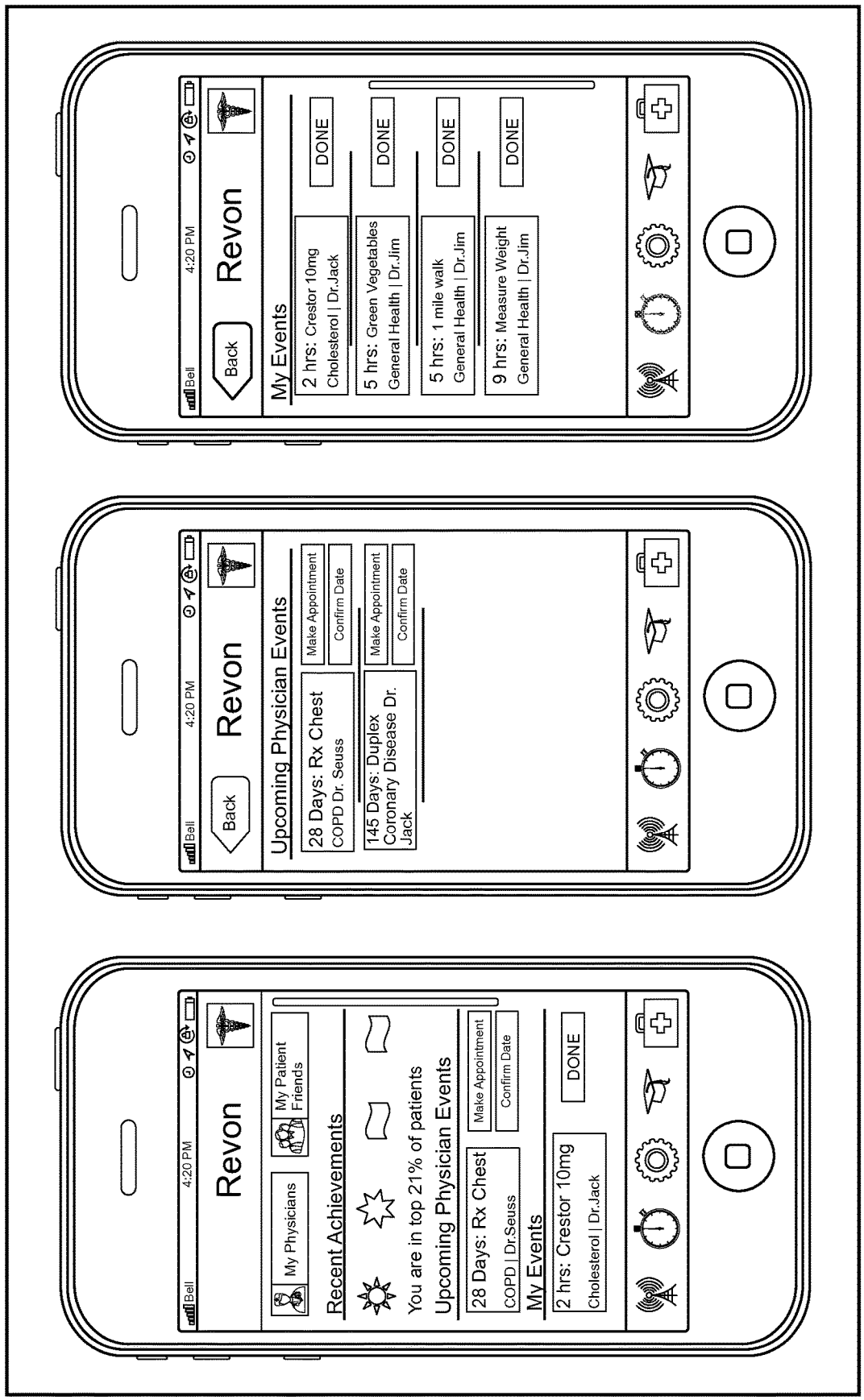
Figure 3C:
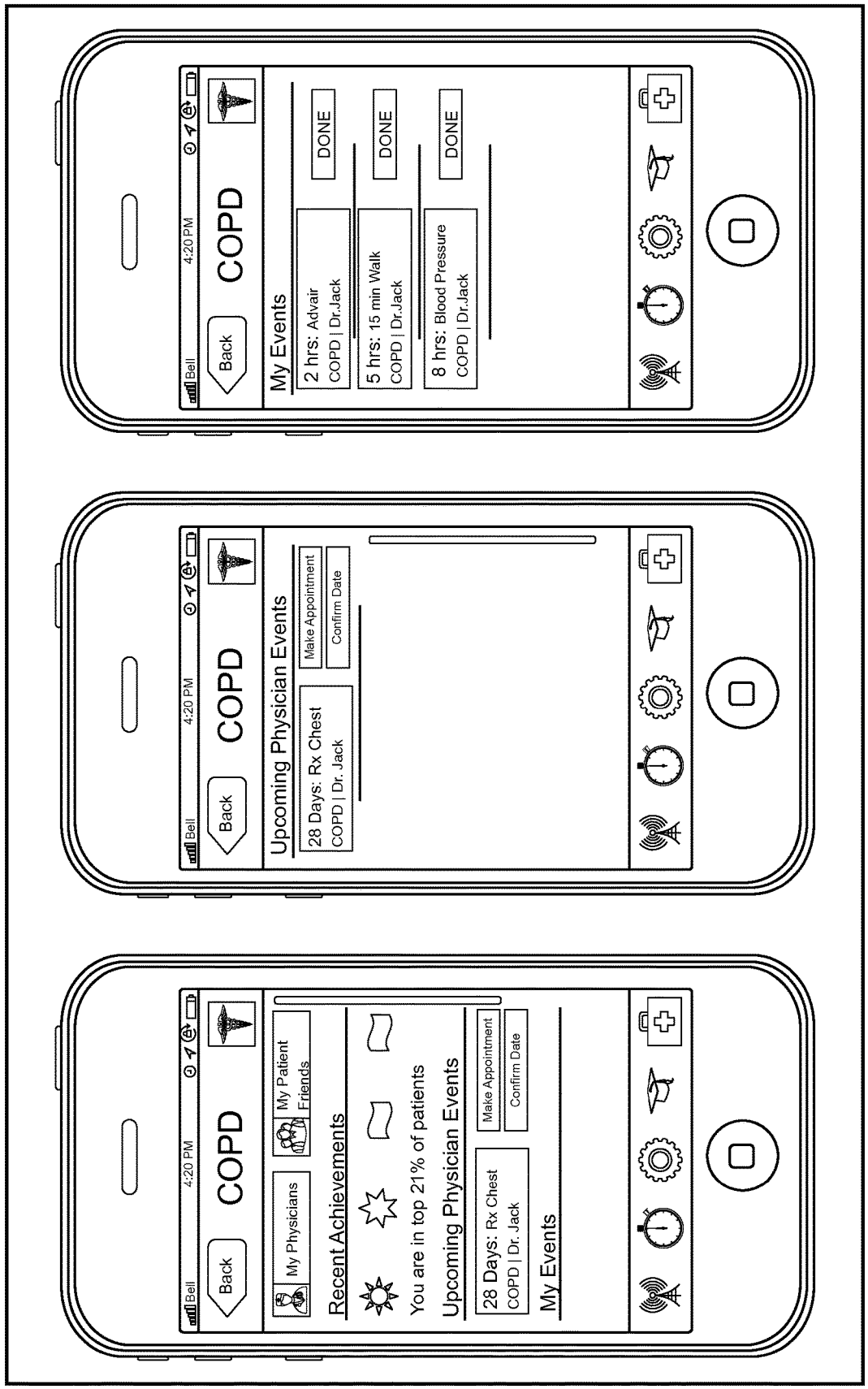
Figure 3E:
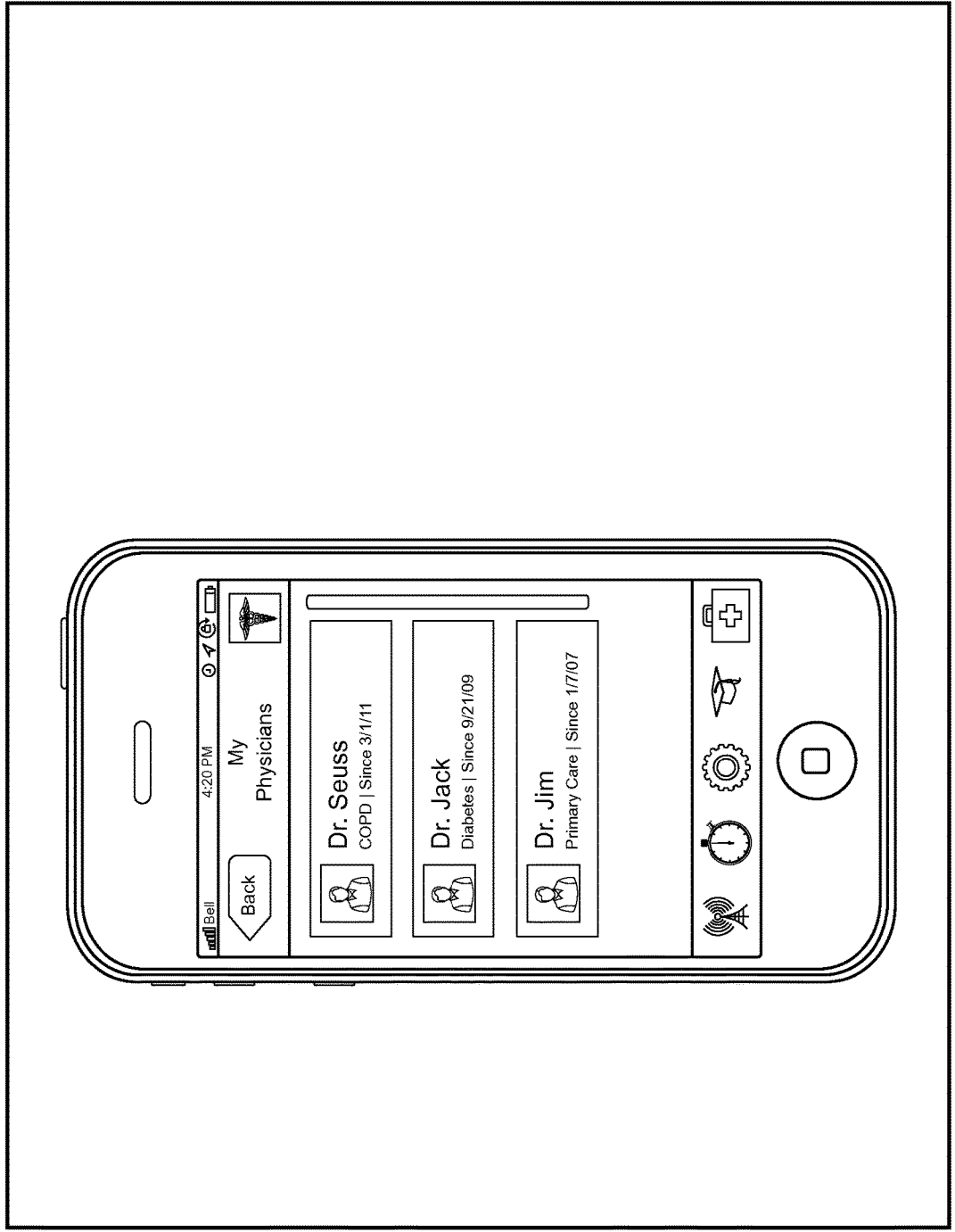
Figure 3F:
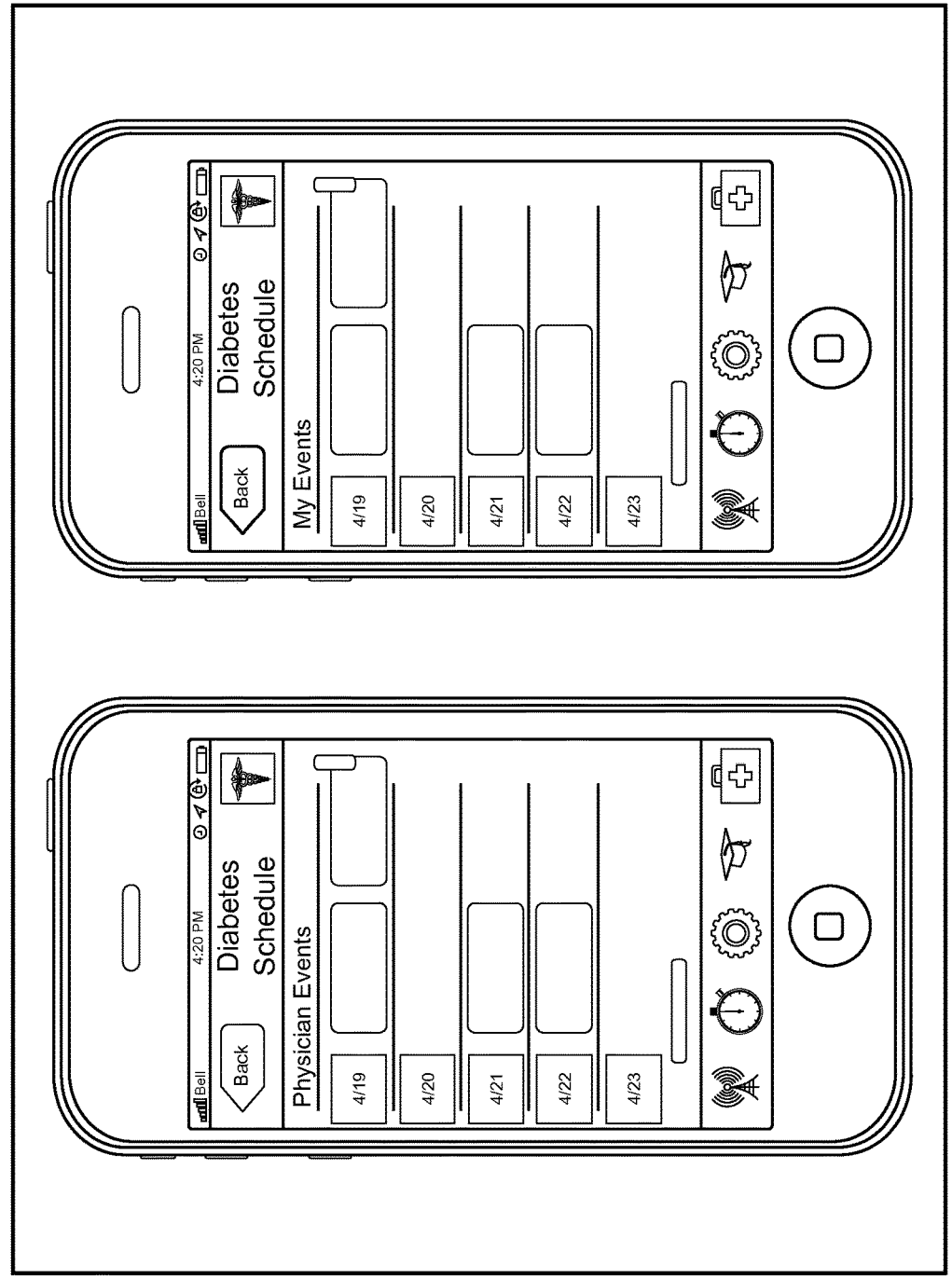
Figure 3G:
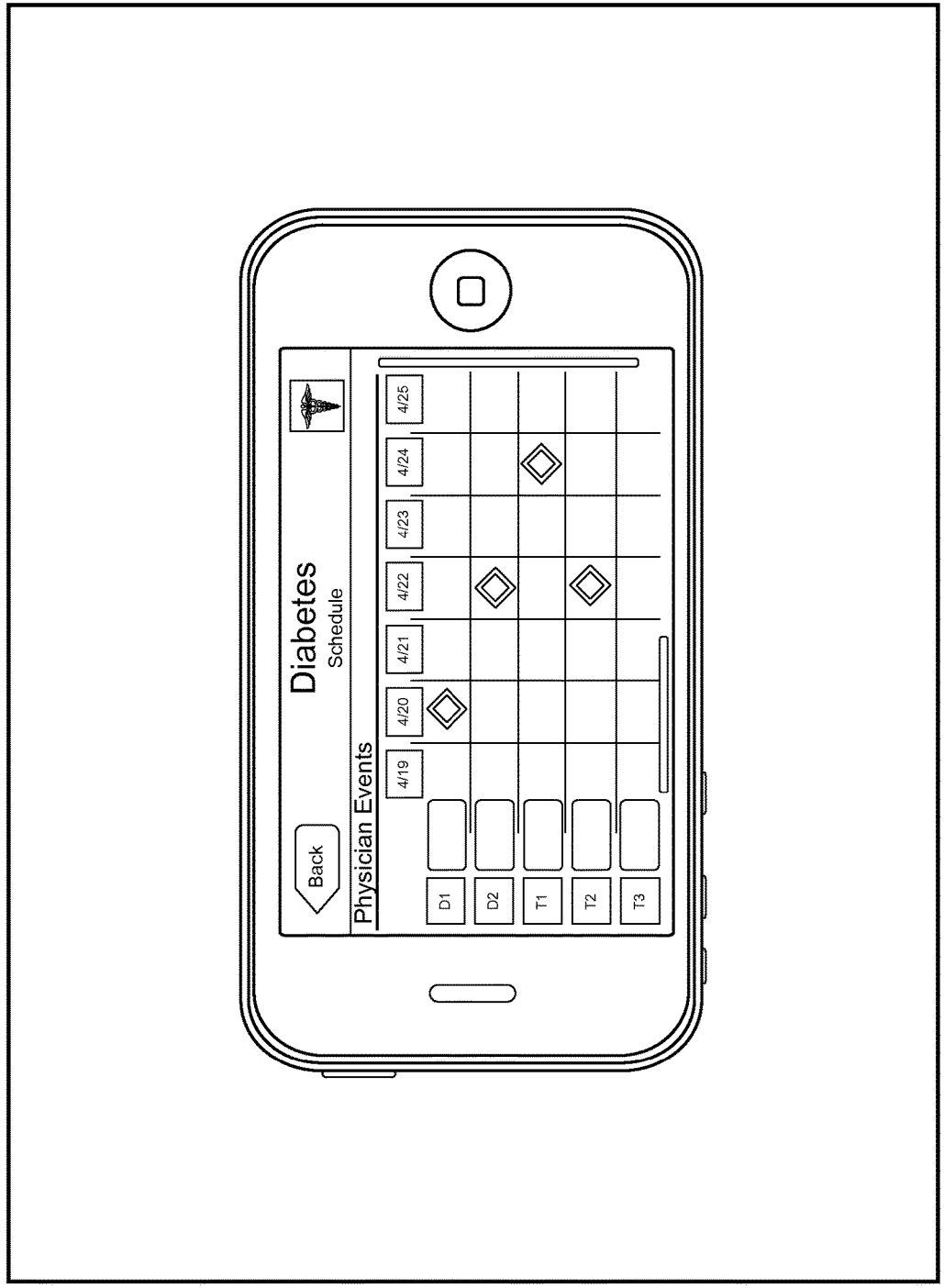
Figure 31:
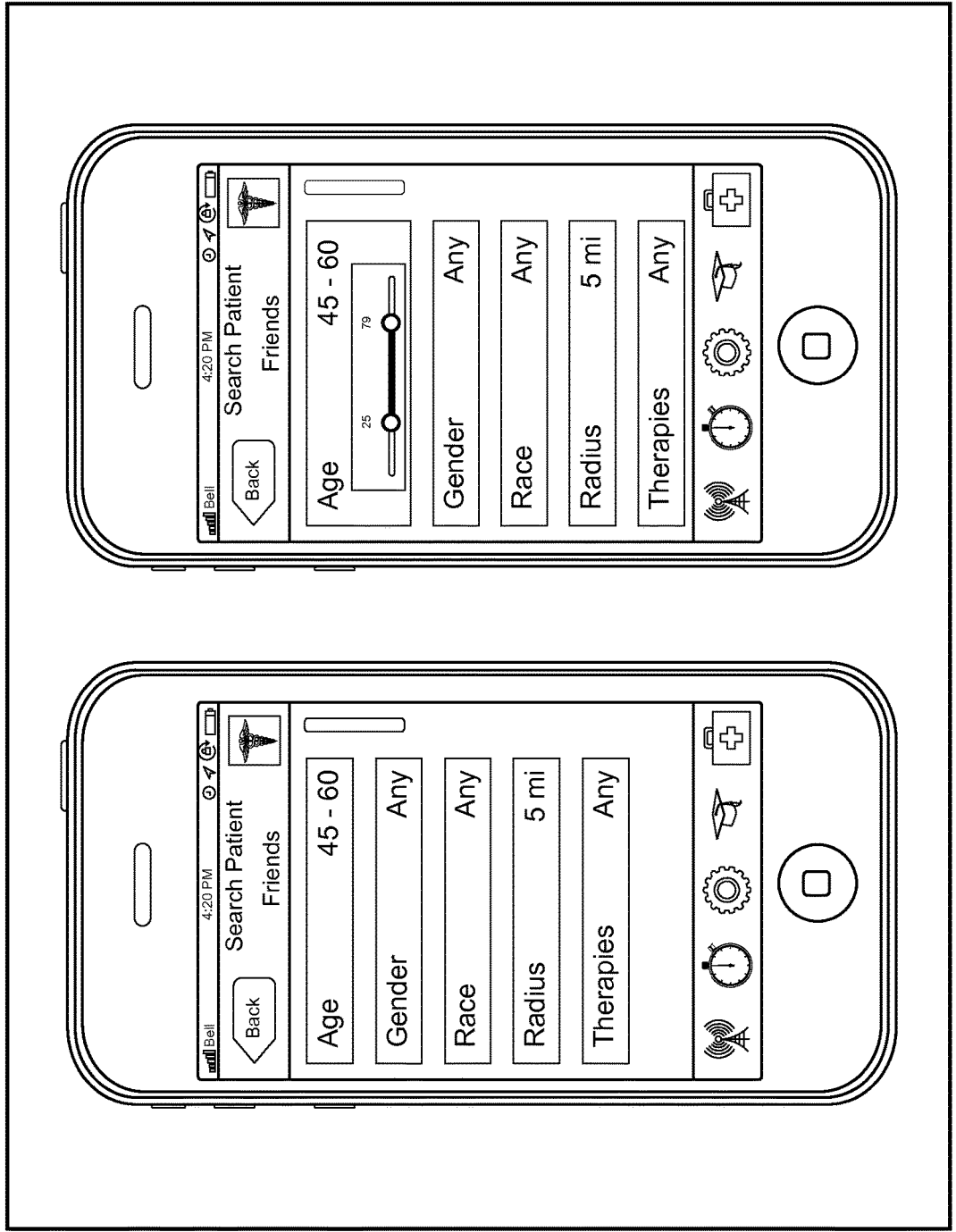
Figure 3J:
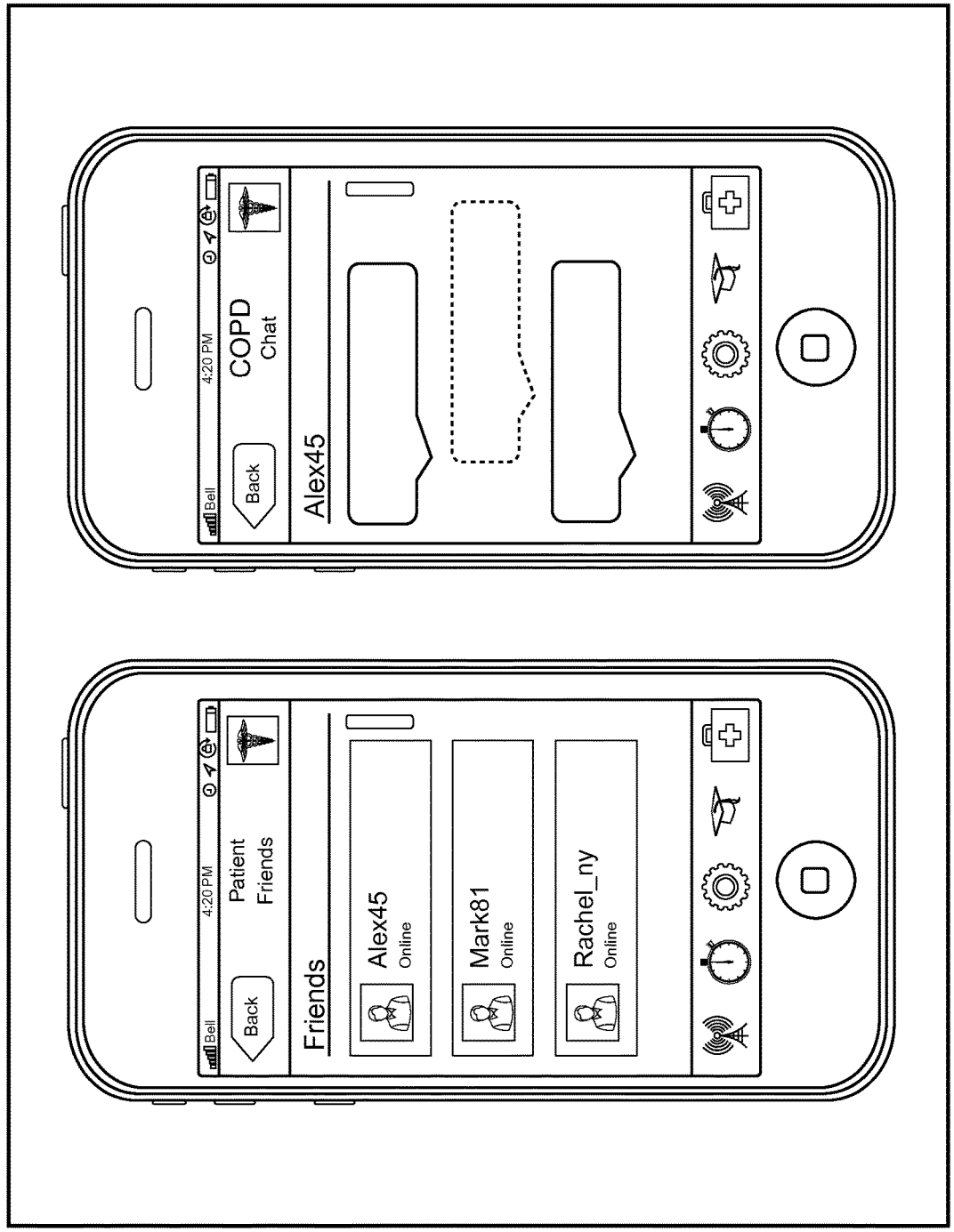
Figure 3K:
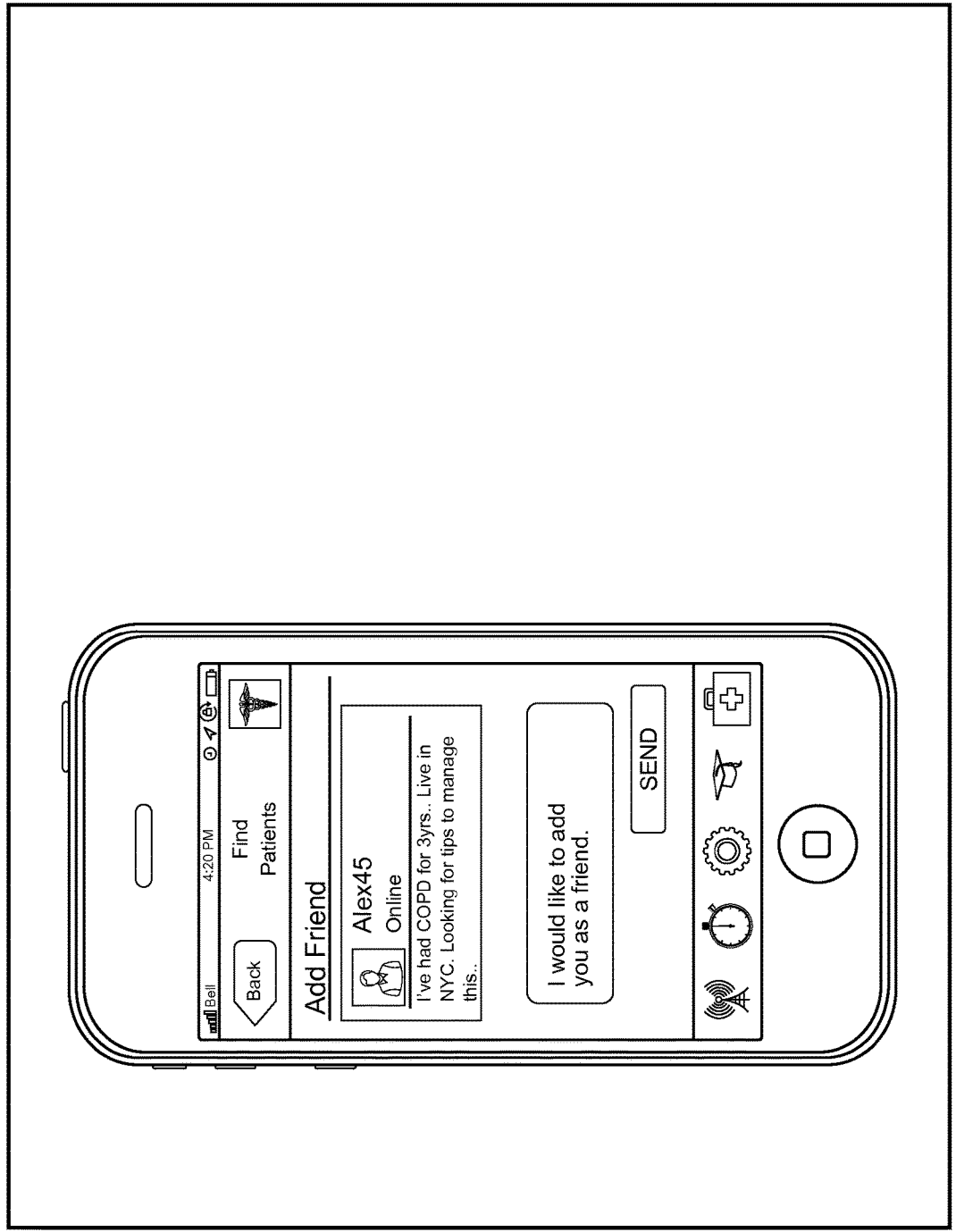
Figure 3L:
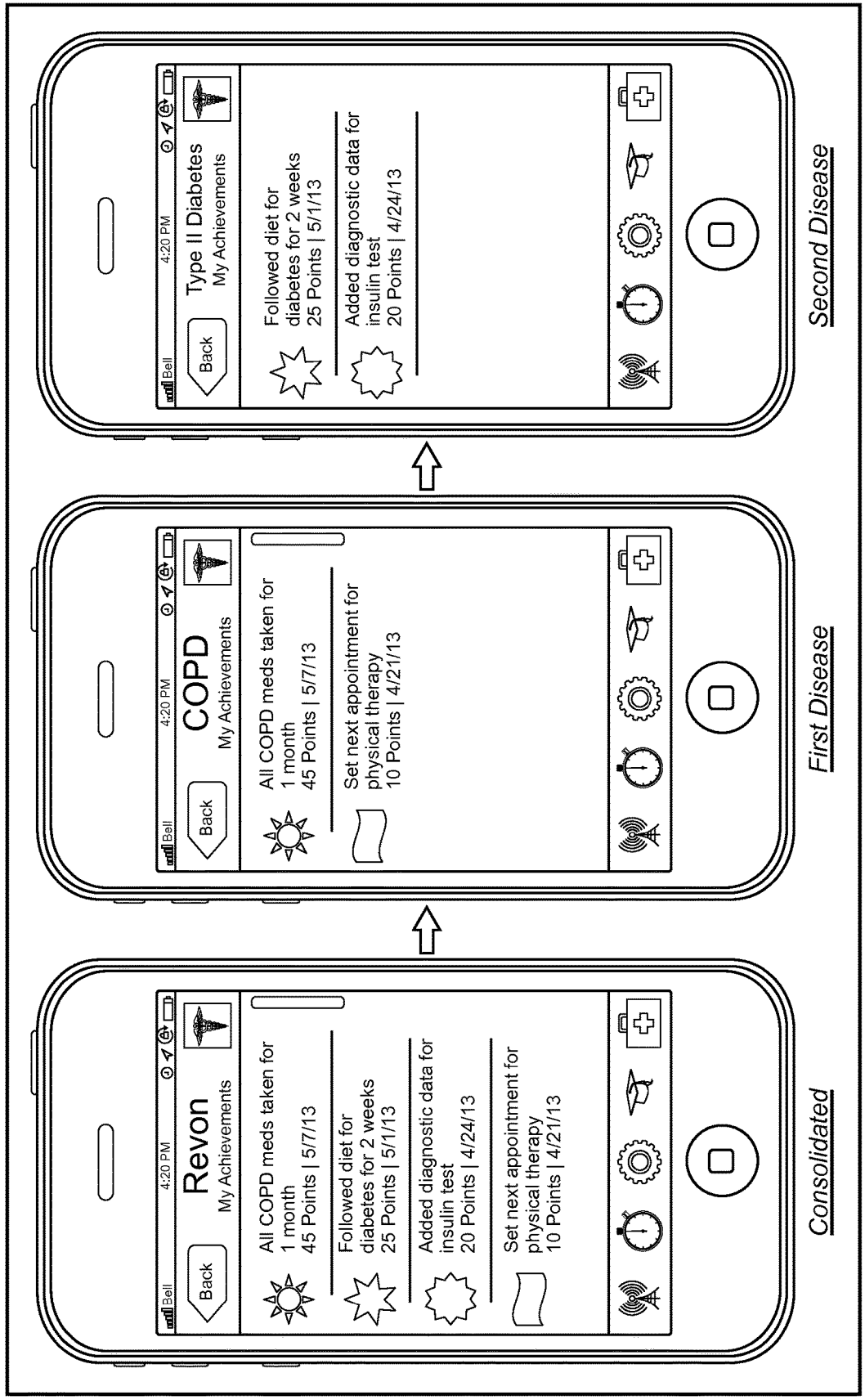
Figure 3N:
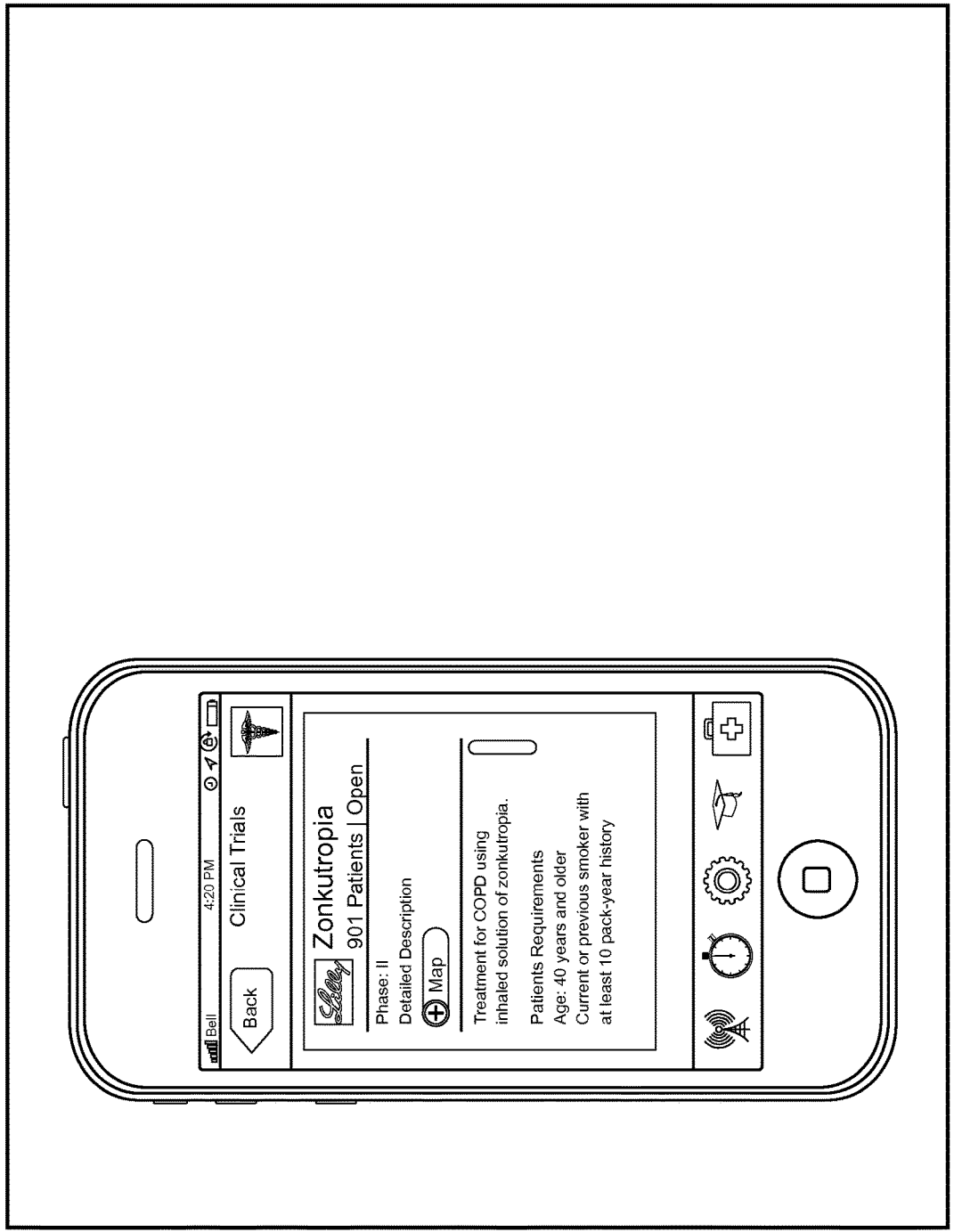
Figure 30:
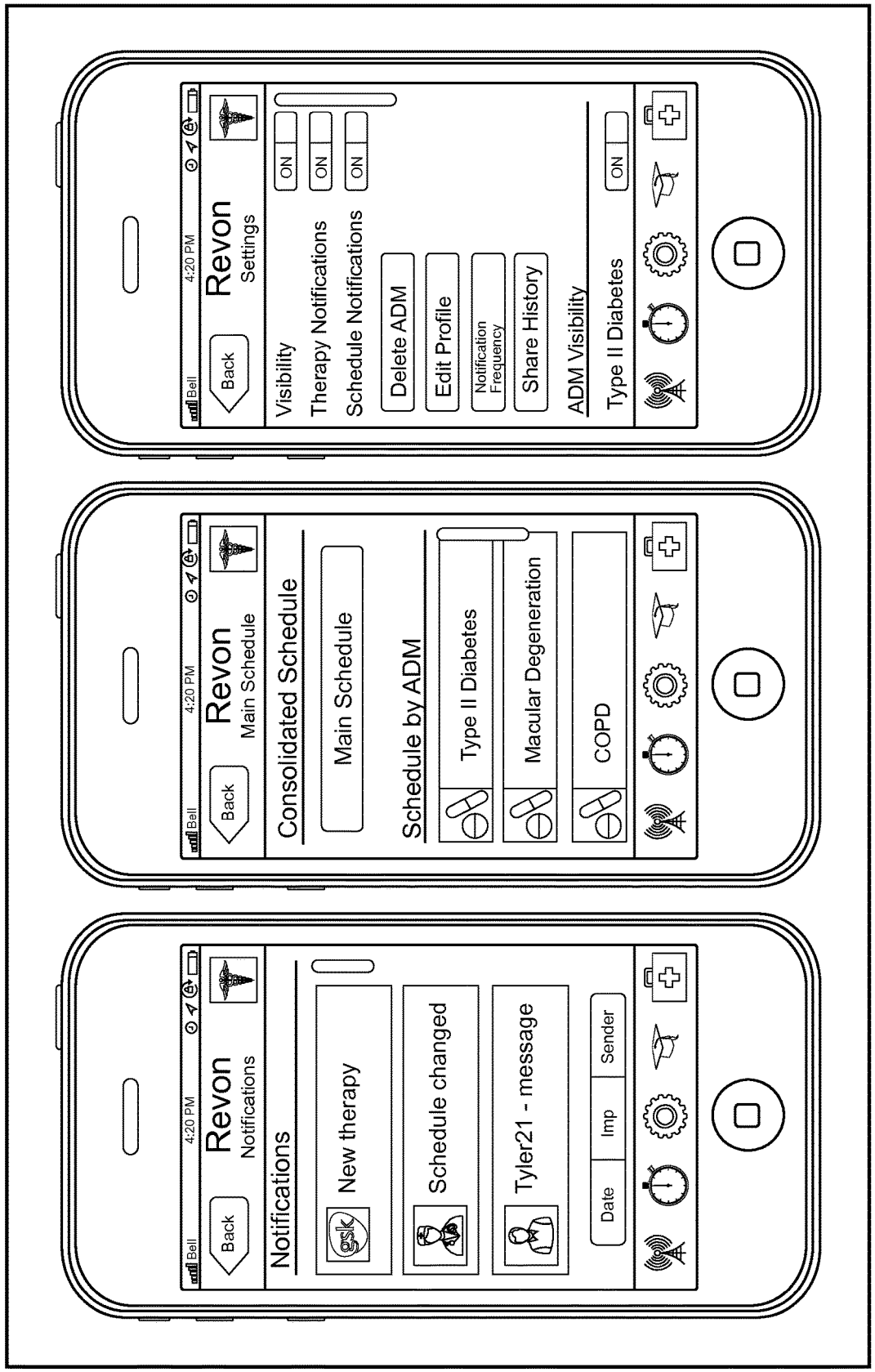
Figure 3P:
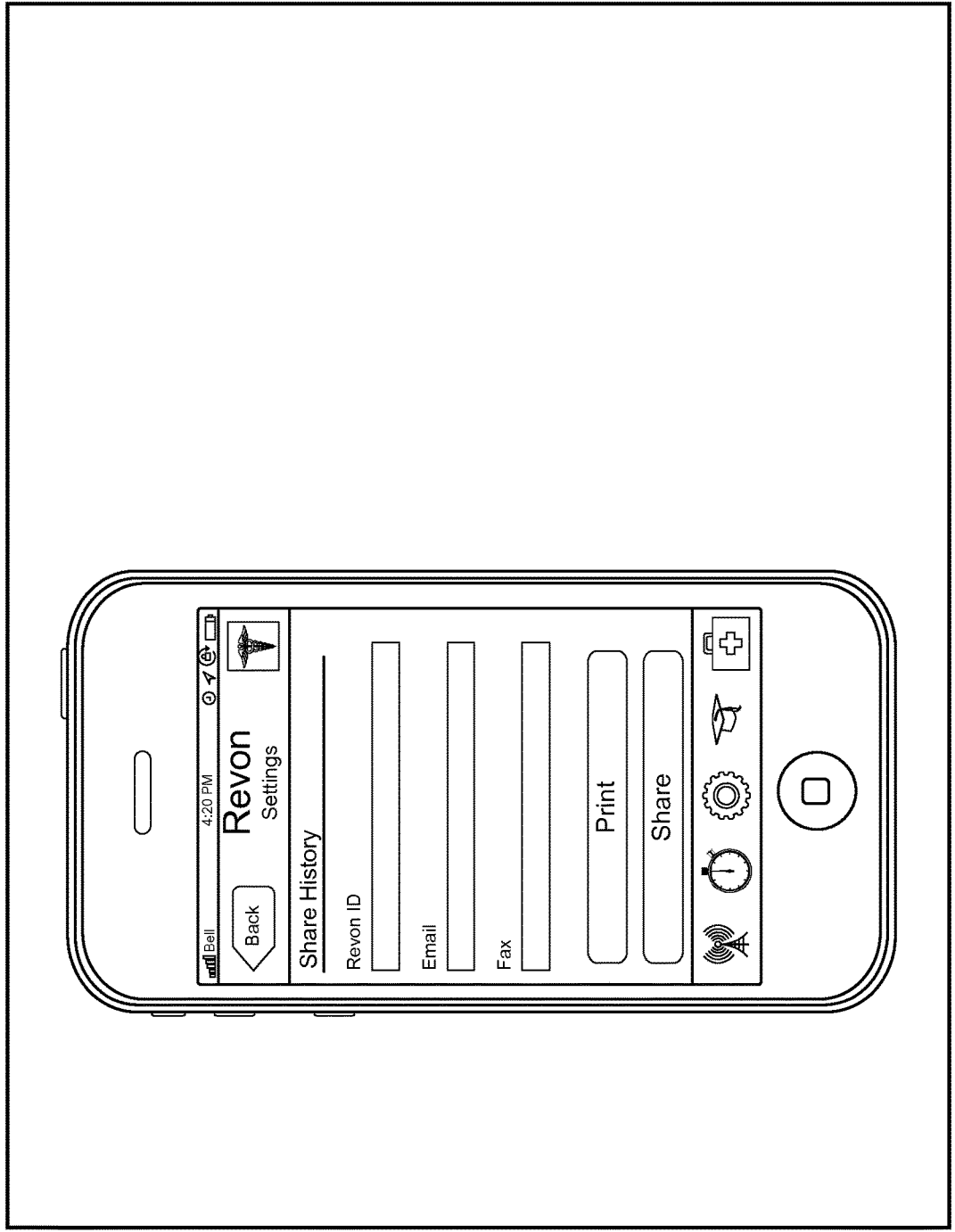

FIGS. 3A-3N show exemplary screens of a patient application. FIG. 3A is a log-in/authentication screen. FIG. 3B (left panel) is a home screen. The home screen presents functions and information consolidated across all of a patient's diseases that have an individual active diagnosis module (ADM). The home screen has a Header Bar which shows the application name (Revon) in the middle. At the bottom is the Navigation Bar which allows direct navigation to some important modules/menus/functions within the app. The first symbol from left lets the user navigate to the Notifications module, the second symbol from the left lets the user navigate to the Consolidated Scheduler, the third symbol from the left lets the user navigate to the Settings Module, the fourth symbol from the left lets the user navigate to the Help Menu; the rightmost module lets the user navigate to the Clinical Trials module. The right two panels of FIG. 3B show screens that appear when a user taps or scrolls down on Upcoming Physician Events or My Events on the left panel. Once the user selects an ADM by swiping across the screen, the user is presented with a disease-specific main screen. In FIG. 3C, it is assumed that user selected the COPD ADM module. The inner hierarchy and structure and the functions and layout for each disease-specific module and main screen are identical or nearly identical to those for the consolidated diseases and home screen. Tapping on the icon in the upper right brings the user back to the home screen. The Back button on any screen takes the user to the previously viewed screen. A button may be provided to allow the user to exit the application.

In some embodiments the home screen may provide one, two, three, four or all of the following five functions (1) My Physicians; (2) My Patient Friends; (3) My Achievements; (4) Physician Events; (5) Patient Events. In some embodiments the home screen may also or alternately provide one, two, three, four, or all of the following five functions: (1) Notifications; (2) Schedule; (3); Settings; (4) Help; (5) Clinical Trials. In some embodiments access to at least some of the functions, e.g., at least some of the functions in the second group may be provided in a navigation panel/bar in the bottom portion of the screen (shown on screens depicted in FIGS. 3B-3P, with symbols for the afore-mentioned 5 functions depicted in that order from left to right). Access to the other functions may be provided in the main portion of the screen as shown in FIG. 3B, left panel. Right two panels in FIG. 3B show detail screens that a patient would view by selecting Upcoming Physician Events or "My Events" respectively on the home screen. Functions accessible via the navigation panel are typically accessible from any screen within the application, but at least some of these functions, when accessed from a disease-specific screen, provide disease-specific content. The functions that are accessible from the home screen provide consolidated information pertaining to all of the patient's diseases in each category, i.e., information of the relevant category is combined for all diseases. For example, a consolidated Schedule is a schedule of events for all of the patient's diseases combined into a single schedule; a consolidated My Physicians function provides a list/map showing all of the patient's physicians; a consolidated My Patient Friends function provides a list/map showing all of the patient's Patient Friends; a consolidated My Achievements function provides a list of all of a patient's Achievements. In some embodiments, when a user swipes across the device screen horizontally (e.g., from right to left) or vertically (e.g., top to bottom) from the home screen, he or she is presented with individual disease-specific screens for each disease for which the patient is registered on the system. A "disease-specific screen" for a disease refers to a screen from which content pertaining to that disease is accessible, e.g., via one or more functions. The name of the disease (or an abbreviation) is typically indicated on a disease-specific screen, e.g., in a prominent position such as centered near the top of the screen. For example, FIG. 3C show disease-specific main screens, in this case for COPD. By sliding a finger on the screen from right to left, the screen will go from disease to disease, e.g., from COPD to diabetes. If the patient is on a main screen for a particular disease, swiping will take the user to a main screen for a different disease. If the patient has selected a function on the home screen or on a disease specific screen, swiping on the screen will take the patient to a screen for a different disease but at the same function level (either top level (main) or a particular function). The inner hierarchy and structure of each disease-specific screen (either main screen or function-specific screen) will be generally identical to the corresponding consolidated screen. For example, FIG. 3D (left panel) depicts a screen after the patient has selected "My Physicians" on the main screen. The patient can see all his physicians on map or list. If the patient clicks on a physician the patient is taken to the right screen on FIG. 3D. If the patient clicks on ALL physicians then all Revon network physicians will show who are the treating physician of at least one confirmed patient who has a disease for which the patient has an ADM. If selected from the consolidated screen it will show all physicians for all diseases. For example, if a patient has COPD, diabetes, and macular degeneration, all physicians who are treating physicians for at least one confirmed patient with COPD, diabetes, or macular degeneration will show. If selected from a disease-specific screen (e.g., COPD screen) all Revon network physicians that have at least one confirmed patient with that disease will be shown. FIG. 3E shows that physicians may be displayed in list format. FIG. 3F shows schedules for physician events (left panel) and patient events (right panel) for a specific disease (diabetes). Schedules may be scrolled vertically, e.g., by swiping, to see past and future events outside the time window shown. The schedule expands to a landscape view format when device is placed in landscape view. FIG. 3G shows a schedule for physician events for diabetes in landscape format. FIG. 3H shows a screen displayed when a user clicks on My Patient Friends on main screen. The patient can choose whether to make himself or herself visible (findable by other patients searching with the application). The system may store a profile of at least those users who choose to make themselves visible, for purposes of permitting others to find them based on patient characteristics. The patient can see friends on map, search for them and get list view. If selected from the home screen, all patient friends are seen, if from a disease-specific screen, only those patient friends who have the disease. A patient can search for existing friends or find new ones through the application. Search screens allow user to set up criteria to look for other patients on network (FIG. 3I). On left screen on FIG. 3J, the patient can see the list of existing patient friends. The list can be filtered by disease. The patient can engage in a chat conversation with a friend also as shown on the right screen on FIG. 3J. Patient can also add new patient friends by sending the requests as shown on FIG. 3K. FIG. 3L shows a patient's Achievements. The left screen is reached from the home screen by clicking the My Achievements function. Screens showing disease-specific achievements (middle and right screens on FIG. 3L) are reached either by swiping from the main Achievements screen (left) or from the main disease-specific screen for a particular disease by selecting My Achievements. FIG. 3M (left panel) shows screen viewable when patient clicks on 'Clinical Trials' button on main screen. Patient sees sites where trials are happening. When a particular site is clicked, a second screen (right panel) is presented with a list of trials happening at that site FIG. 3N is reached when the patient clicks a particular trial from previous screen. It lists certain trial details. The patient may click on trial name to view further details (e.g., link to trial on ClinicalTrials.gov or trial website) and/or contact information for site or investigator. FIG. 3O shows screens a user sees from the navigation bar at the bottom. These screens can be accessed from anywhere in the application. When the user clicks the leftmost icon on the navigation bar, he will see the left screen of FIG. 3O, which shows all notifications in a chronological order. When user clicks the second icon from left, he sees the middle screen, which allows him to see his consolidated schedules as well as any schedule by disease. When the patient selects the Schedule icon from the navigation pane (either from home screen or any disease-specific screen) they see a combined schedule including physician events and patient events. If Schedule icon is selected from home screen, schedule displays physician events and patient events for all the patient's diseases. If Schedule icon is selected from a patient-specific screen, schedule displays physician events and patient events for that disease. When user clicks the third icon from left, he can see the screen at the right, which allows the user to change his app settings. A user can share his medical history (Patient Medical History) using the screen shown on FIG. 3P. The user gets to this screen by clicking Share History button on Settings screen.

Figure 4A:
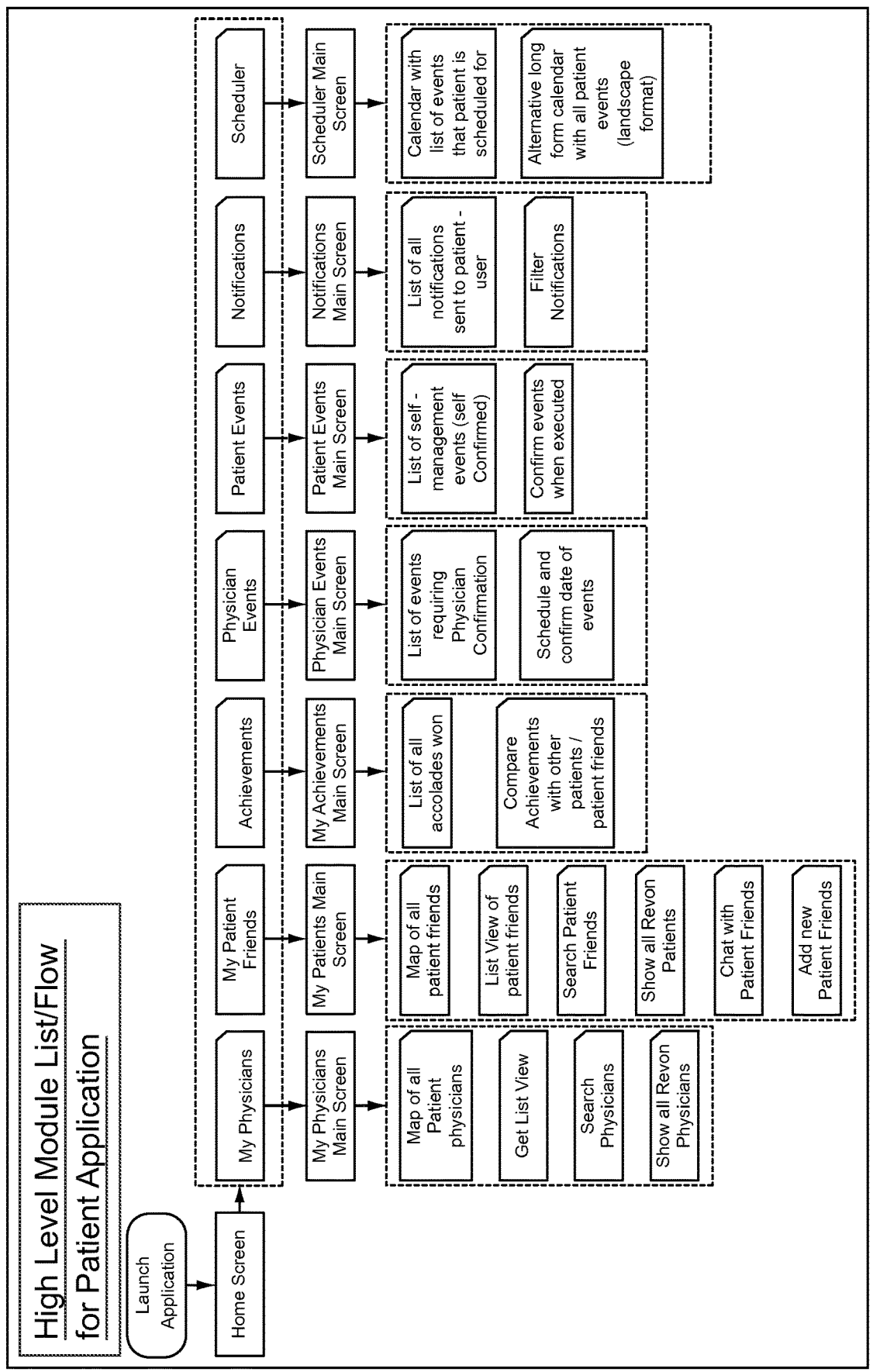
FIGS. 4A and 4B show patient screen modules and screen flow according to certain embodiments.
Figure 4B:
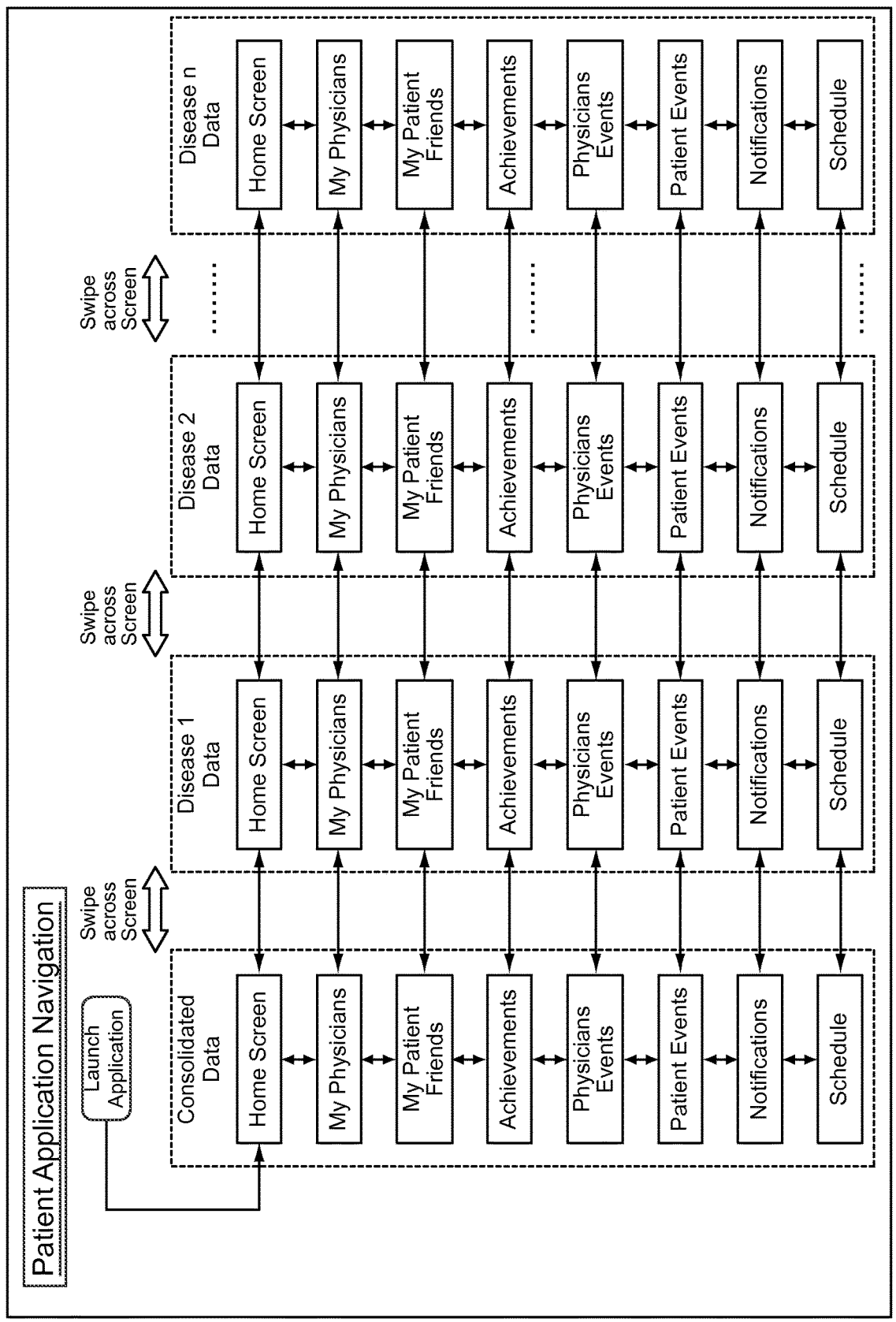

FIG. 4A shows a high level module list/flow for a patient application with the various functions described above (with the exception of Settings, Help, and Clinical Trials). FIG. 4B shows navigation through a patient application. Disease-specific screens in each of the functional categories shown on the vertical dimension may be reached by swiping on the horizontal dimension. Within a disease, each function can be reached from the main (top level) screen for that disease by tapping the appropriate button. The layout depicted in FIG. 4B can be adapted for use in any of a variety of contexts, e.g., for display of and access to health information in any of a variety of categories on a consolidated (across diseases) and disease-specific basis for any of a variety of purposes including, but not limited to, for purposes described herein.

The content and tools (e.g., search tools, display tools) available via the various functions of a patient application may vary in various embodiments. For example, a list of "My Physicians" may be, e.g., all physicians who have contributed to any of a patient's ADMs (e.g., at any time or within a predetermined past time window such as the previous 2 years) or may be limited to a patient's current treating physicians, optionally including additional physicians that a patient decides to add to the list. In some embodiments a My Physicians function provides contact information, e.g., one or more phone numbers, email addresses, street addresses, and or links to websites may be listed for one or more of the physicians and/or for one or more practices, clinics, medical centers, or other health care organizations where such physicians practice, e.g., where the patient would typically go for an appointment with the physician. In some embodiments a patient may be able to phone or send a text message or email to the physician directly from the screen on which the physician's name appears, e.g., by selecting the number or selecting a "phone", "message", or "email" icon. In some embodiments a patient may be able to make an appointment with a physician via the screen on which the physician's name appears. In some embodiments an appointment may be made by making a phone call to the physician's practice or using a web-based appointment scheduling program that allows the patient to select among available appointment slots. In some embodiments, when a patient selects a physician's name, the patient may be asked whether he or she wishes to phone or send a text message or email to the physician or make an appointment with the physician. In some embodiments, one or more HCPs who are not physicians may be included in "My Physicians". Such HCPs may be, e.g., nurse practitioners or physical therapists who provide health care to the patient for that disease, possibly under direction or upon recommendation of the treating physician. In some embodiments a My Physicians function provides a tool that allows a patient to display a list or map view of all physicians who are members of the Revon network. In some embodiments a "My Patient Friends" function for a disease provides a list of individuals who are members of the disease network for that disease that have accepted a request by the patient to be added as friends.

As noted above, in some embodiments a patient application provides an "Achievements" function. This function informs the patient about certain of his or her achievements (which term is used interchangeably with "accomplishments") in terms of performing one or more patient events specified by the application (according to physician's treatment program for one or more diseases as set forth in the patient schedule). The app may inform the patient of his or her achievements by providing symbols (e.g., accomplishment badges, medals), descriptive text, and/or points. Achievements attained in different categories of tasks may have different symbols associated with them. Descriptive text may, for example, describe the achievement, provide praise or compliments, rank the patient's performance as compared with that of other patients with the same disease (e.g., on a percentile basis), or inform the patient how his or her performance compares to their own previous performance or ranking. Achievements may include, for example, taking at least a certain percentage of medications as specified by the schedule, scheduling medical appointments as specified by the schedule, keeping scheduled medical appointments, adhering to a diet as specified by the schedule, adhering to an exercise program as specified by schedule, or performing body monitoring as specified by the schedule. In some embodiments performance of a recurring patient event may be assessed over a selected time period, e.g., between 7 days and 30 days (or 1 month). As with other functions in certain embodiments, achievements may be presented or accessed on a consolidated basis (across all diseases for which the patient has ADMs) or on a disease-specific basis. In some embodiments the home screen may show one or up to several recent achievements. In some embodiments, accessing the "Achievements" function from the home screen will show all achievements for all diseases consolidated on one screen. The achievements shown may be ones that occurred within a recent timeframe, e.g., up to 30-60 days prior to the date on which the function is accessed. When a user swipes across, he or she will see accomplishments for specific diseases. In some embodiments, when a user swipes vertically on the consolidated achievements screen, he or she will see previous achievements. For example, some or all achievements attained from the day that the user started to use the app may be accessible in chronological order. If the user swipes vertically on a disease-specific achievements screen, he or she will see previous achievements for that disease In some embodiments content pertaining to at least some ADMs related to the same underlying disease may be consolidated for purposes of presentation to a patient via a patient application. For example, in some embodiments two or more or all ADMs related to a particular underlying disease may be presented as part of a unified ADM rather than as individual ADMs. In some embodiments two or more or all ADMs related to a particular underlying disease and that have the same treating physician may be presented as part of a combined ADM rather than as individual ADMs. In some embodiments a user may select to combine multiple ADMs or separate a combined ADM. In some embodiments all ADMs related to a particular underlying disease are presented consecutively when a patient moves through disease-specific screens of an application.

In some aspects, the Revon system provides means for a patient to have a viewable, editable, version of his or her medical history (Patient Medical History), which the patient may print and/or share with others, e.g., physicians whom the patient may visit in the future. In some embodiments a Patient Medical History may be portable, automatically updated. A Patient Medical History may contain health information at the level of detail of a typical general patient intake or medical history form that a patient is often asked to complete when visiting a physician for the first time. In some embodiments the information that comprises a Patient Medical History is stored on a central server and may be accessed by a patient via the Internet from any device and location from which an Internet connection is available (subject to appropriate authorization such as entry of the patient's userID and password). In some embodiments a copy of the Patient Medical History is stored on an electronic device, e.g., a portable electronic device such as a smartphone, that is owned, leased, or otherwise under control of the patient. The copy stored on the device may be synchronized with the central server on a regular basis and/or whenever the Patient Medical History is accessed from the device.

In some embodiments a Patient Medical History comprises health information that is entered, e.g., by a patient, during a patient registration process described herein. In some embodiments Patient Medical History may be made available to the patient from within a patient application. For example, in some embodiments a patient application provides a Patient Medical History button, which may be among the Settings functions that are accessible from the home screen. In some embodiments the Patient Medical History can be viewed and edited by the patient. In some embodiments the Patient Medical History may be displayed in an editable format, e.g., the patient can tab, scroll, or swipe through the displayed information and edit the information as desired. In some embodiments the Patient Medical History can be edited by first selecting an Edit function, which converts the displayed information to editable format or otherwise provides editing capability. In some embodiments the Patient Medical History is searchable. For example, when at least a portion of the Patient Medical History is displayed, a Search function may be displayed that, when selected, allows the patient to enter one or more terms on which to search. In some embodiments the Patient Medical History can be printed and/or shared by the patient. For example, when the Patient Medical History function or at least a portion of the Patient Medical History information is displayed, the screen may allow the patient to select a Print function and/or to send a copy of the Patient Medical History via email, text message, or other forms of communication.

In some embodiments a Patient Medical History may be updated automatically based on information entered into an ADM of that patient. For example, as additional diagnoses are confirmed for the patient or the patient's medications are changed (e.g., new medications added, doses changed, medications stopped), new ADMs are added and/or the patient's existing ADMs are updated accordingly, the new or additional information may be used by the system to appropriately update the Patient Medical History. In some embodiments a Patient Medical History may be updated by the patient. For example, diagnoses or events that pertain to diseases for which the patient does not have an ADM may be added by the patient. Family history or other components of a Patient Medical History that may not be captured by a patient's ADMs may be added or updated by the patient. In some embodiments the system may periodically remind the patient of the most recent patient-initiated update to the Patient Medical History or ask the patient to confirm that the information in the Patient Medical History is current. The Patient Medical History and/or a printout or electronic copy of the Patient Medical History may be annotated with the date that the information or any particular data element was most recently updated by the system and/or by the patient.

The Revon system may comprise or access a database comprising at least one ADM schedule template (ST) for each of a plurality of diseases. Such a collection of ADM STs may be referred to as the Revon ST library. The number of diseases represented by ADM STs in the Revon ST library may be anywhere from one to hundreds, thousands, tens of thousands, up to the number of diseases that are recognized in the medical profession, e.g., those to which a code is assigned in ICD-10-CM, although this is not to be considered limiting. In some embodiments the number of diseases represented may be between 5 and 100, between 100 and 1,000; between 1,000 and 5,000; between 5,000 and 10,000; between 10,000 and 30,000, or more. The Revon system may supply a default ADM schedule template (ST) for one or more diseases, which may be selected from the Revon ST library. When an ADM is initially created for a patient and a diagnosis entered, the ADM may initially comprise the default ADM ST and may continue to do so until modified by the treating physician or replaced with a different ADM ST by the treating physician. A default ADM ST may have a predetermined set of Type I and Type II physician events and associated timings and a predetermined set of patient events and timings. Certain events such as hospitalizations or visits to an emergency room may typically be of interest to all HCPs managing a patient for any disease and may in some embodiments be included on every default ADM template. In some embodiments the Revon ST library comprises multiple different schedule templates for one or more diseases, wherein the schedule templates may differ with regard to the set of procedures included and/or may have different timings for performing one or more of the procedures. For example, STs may exist for newly or recently diagnosed patients, stable patients, patients who have recently experienced a disease exacerbation, patients who have a mild, moderate, or severe form of the disease, patients who have an early, intermediate, or advanced stage of the disease, etc. The procedures and/or timings for different STs may be selected to be appropriate for managing a patient in a particular category. For example, it may be appropriate for a newly diagnosed patient to have frequent appointments with his or her physician during the first few months after diagnosis to permit evaluation of the patient's response to therapy. In some embodiments the Revon system may analyze results of one or more diagnostic tests performed on a patient and may select a particular ST as an ST for a patient instead of the default ST and/or may suggest a ST or suggest changing an ST for that patient based at least in part on the results. In some embodiments a schedule template for a patient may be changed at any time either by selection among the Revon system ST library or by the HCP within his or her discretion. For example, if a patient's HCP determines that recently diagnosed patient has responded well to initial therapy, the HCP may change the patient's ST from "recently diagnosed" to "stable". If a stable patient experiences a disease exacerbation, the patient's HCP may change the patient's ST from "stable" to "post-exacerbation" and may change it back to "stable" once the patient's condition is stable again. A HCP may have his or her own library of ADM STs on the Revon system. For example, a HCP who has created an ADM ST or modified an ADM ST in the Revon ST library may save that ST to his or her own personal ST library. A HCP may also or alternately save any of the STs from the Revon ST library to his or her own personal ST library. In some embodiments a HCP may contribute a ST that he or she has created or modified to the Revon ST library. In some embodiments the Revon system may require that a patient is assigned a diagnosis from a predetermined list by their HCP. In some embodiments the Revon system may permit HCPs to define their own disease entities. A treating physician for a particular disease may be able to view ADM STs for diseases for which he or she is not the patient's treating physician. The physician may recognize that certain physician events and/or patient events that would be part of his or her treatment plan for the patient are already scheduled in a patient's existing ADM STs. The physician may refrain from including those events in an ADM ST under his or her control or modify the schedule for his or her treatment plan to coincide with the timing of the event in the schedule for the different disease, thereby potentially reducing the number of procedures that may be performed on the patient. In some embodiments the Revon system may detect potential redundant or duplicative procedures and notify the physician who added such procedure(s) and/or the patient. In some embodiments, if a physician tries to add a new event that may potentially conflict with an existing event or tries to modify an existing event in a way that may potentially conflict with a different existing event, the physician may be informed accordingly. A potentially conflicting event may for example, be a medication or procedure that may be medically contraindicated for a particular patient based on information available in the ADM and/or in other ADMs for that patient or that may warrant a change in dosage of an existing medication, change in monitoring frequency, or other modification of an existing treatment plan. In some embodiments the Revon system may inform the physician of a potential conflict between an existing event and a new event or modification to an existing event that the physician tries to add or make. In some embodiments the physician who added an existing event may be informed by the system (e.g., by a notification in the ADM from which the existing event was added) of an attempt to add a potentially conflicting event or to modify an existing event in a manner that may create a potential conflict. In some aspects, the Revon system provides means to rationalize multiple different treatment plans to provide a more efficient overall treatment plan for a patient.

In some embodiments an ADM schedule template may be created by a user by selecting a diagnosis, selecting one or more procedures, and selecting a timing for performing each procedure. The diagnosis, procedures, and timing may be selected from menus, scroll-down lists, by entering text, or in any of a variety of other ways. A timing for a procedure may specify a frequency for performing the procedure, a time interval at which the procedure is to be performed, or one or more specific time periods (e.g., 3 months, 6 months) in the case of a procedure that may not recur or may be performed a limited number of times or at irregular intervals. A time interval may range from as little as one day to as long as 5 to 10 years, depending, e.g., on the procedure, the disease, and the particular characteristics of the patient. A frequency for a physician event may be, for example, every month, every 2, 3, 4, 5, 6, 9, 12, or 24 months, to name a few. An appropriate frequency may vary over time. For example, a drug may be administered in multiple cycles, each including multiple doses of the drug, with the cycles being separated by time periods in which the drug is not administered. A schedule may specify administration of a drug in accordance with a dosing schedule set forth in the approved label for such drug or accepted in the art. In the case of a drug that has been approved for treating the disease or studied in a clinical trial, a schedule may specify administration in accordance with a dosing schedule used in a clinical trial that demonstrated efficacy of the drug in treating the disease. In some embodiments a schedule template may be created by a user (e.g., an administrator of the Revon system or an HCP) who is authorized to add the schedule template to the Revon schedule template library. In some embodiments the ST is thereby made available to at least some other users, e.g., HCPs who are registered users of the system for, e.g., viewing and/or selection for managing a patient In some aspects, a system, application, or module (e.g., any system, application, or module described herein) interfaces with or is capable of interfacing with any of a variety of external or internal systems or modules. Such systems or modules may include, e.g., EMR/EHR/EDC systems of various providers, external authentication tools, web services APIs such as Google maps, device APIs for device data such as geolocation, to name a few.

In certain embodiments a patient application can be accessed across any of a variety of different electronic devices. For example, while smartphones have been emphasized as an example, other electroninc devices such as tablets, notebook or laptop computers, desktop computers, may be used. In some embodiments a patient application may synchronize across multiple devices. In certain embodiments a patient can access the same functions and information as are available in the patient application, organized in the same general way, by visiting a website (Revon system website) and entering his userID and password. In certain embodiments, access throught the website might require a second layer of security beyond a userID and password. The various screens are displayed in a browser, and the patient can view screens, navigate using similar navigation tools, enter data (e.g., confirm patient events), and perform activities such as making appointments, visiting websites, etc. It will be understood that the particular functions available when an account is accessed using a browser or certain electronic devices may be limited based, e.g., on the capabilities of the device being used and/or the limitations of the browser. Functions that require use of capabilities or apps that are not available on the device being used may not be available. For example, a desktop computer may not have geolocation or phone call capabilities. Alternate means of communication or navigation may be provided. For example, ADMs may be presented on the home screen in a list format if the device does not have touchscreen capability that would permit swiping. In some embodiments, if the device has voice recognition capability, the user may provide instructions to the app at least in part orally instead of or in addition to by input via the screen. As used herein, "swipe" or "tap" encompasses actions in which the user's finger or other body part is in physical contact with the screen or other input device during at least part of the action. In the case of devices equipped with appropriate gesture recognition software, a gesture equivalent to a swipe or tap may be performed without physical contact with the screen. For example, a gesture such as waving a hand or finger in the air above a screen or eye movement may be used In some aspects, a system of the present invention comprises a database comprising health information organized on a patient-specific and disease-specific basis, wherein the information is organized and searchable for patients having any of a variety of patient characteristics, diseases, and/or disease characteristics in a manner that maintains patient anonymity. In some embodiments at least some health information for a patient is physician-confirmed. For example, in some embodiments health information for a patient comprises at least one physician-confirmed diagnosis. In some embodiments all or substantially all diagnoses in the database are physician-confirmed and/or diagnoses that are not physician-confirmed are distinguishable from diagnoses that are physician-confirmed, so that a search based at least in part on diagnosis can be limited to patients that have physician-confirmed diagnoses or health information that is associated with a physician-confirmed diagnosis. In some embodiments health information in the database may be searched to identify potential clinical trial subjects based on disease diagnosis and, in some embodiments, based at least in part on one or more patient characteristics and/or disease characteristics. In some embodiments the system provides functions by which an entity or individual may identify patients based on search criteria (but without receiving patient identifying information) and may contact patients so identified. In some embodiments the contacting occurs via notifications provided to the patient through a patient application described herein. In some embodiments, the contacting occurs through email in a way that doesn't require the patient's email address to be disclosed to the third party, e.g., the Revon system may send the email without disclosing the email address to the third party. The notifications may thereby be provided in the context of activities that a patient may ordinarily perform using the patient application, such as schedule checking, appointment making, or confirming a patient event (as described herein). In some embodiments the Revon system may provide function(s) that allow a patient to opt in to receive notifications, opt out of receiving notifications, and/or respond to notifications, while maintaining patient anonymity in that the entity or individual from which a notification originates (e.g., a pharmaceutical company, regulatory authority, medical researcher, etc.) does not receive patient identifying information. Notifications may include announcements of the availability of newly approved therapies, new clinical trials or other experimental therapies, health-related warnings, or other health-related information. In some embodiments a patient may selectively opt in to receive certain types of notifications or from certain individuals, entities, or types of entities.

Figure 8:
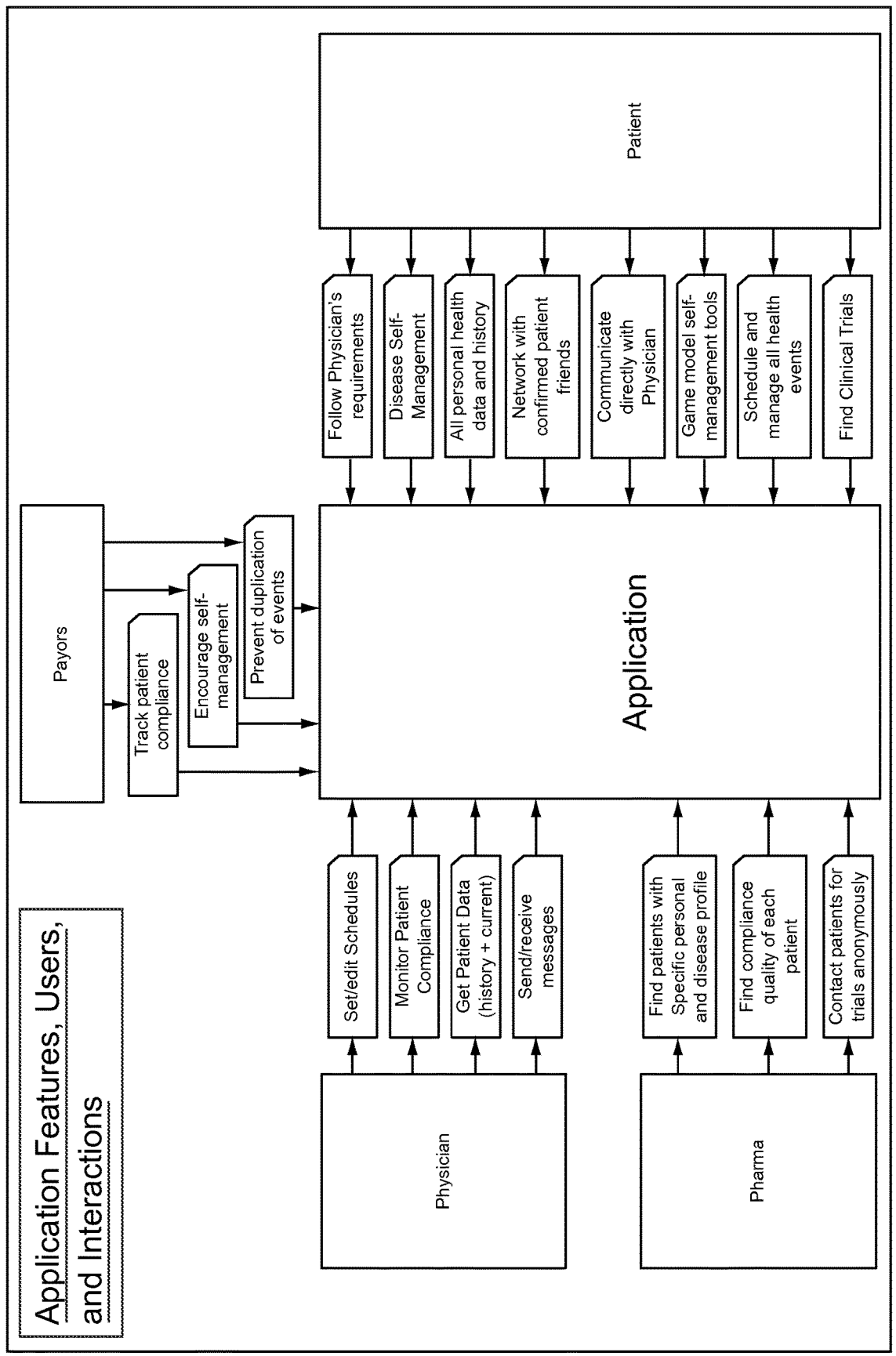
FIG. 8 is a schematic diagram of various application features, users, communication flows and capabilities, illustrating individuals and entities that interact with or via an application according to certain embodiments.

It will be understood that the Revon system may include a variety of components that carry out various tasks described herein. For example, the Revon system may comprise components that (1) provide for creation, modification, management of schedule templates and ST libraries and associated databases; (2) manage user enrollment and accounts; (3) process input from HCPs and patients, (4) analyze procedure codes and determine the physician event to which they correspond; (5) update physician and patient schedules; (6) provide for the patient social networking functions, among others. The Revon system may comprise or access one or more databases that store, e.g., disease identifiers (diagnoses), disease definitions and/or diagnostic criteria, procedure identifiers, HCP identifiers, patient identifiers, HCP data, patient health information, etc. The Revon system may comprise interfaces between various components, databases, and/or external systems, as appropriate. For example, the Revon system may provide for interactions between entities such as physicians, patients and payors as illustrated in FIG. 8, which is a schematic diagram of various application features, users, communication flows and capabilities, illustrating individuals and entities that interact with or via an application according to certain embodiments. It will be understood that the Revon system or any component, database, or interface thereof may be embodied as one or more computer program products, which may comprise computer-executable instructions for performing any of the processes and executing any of the functions described herein.

Example Use

Without limiting the invention in any way, a use case illustrating certain aspects and features of the invention may be as follows: Mr. John James, a 75 year old man with a history of type II diabetes, macular degeneration, and COPD, has recently moved to Louisville, Ky., and needs to find a primary care physician. A neighbor who is a Revon Patient recommends Dr. Randall Resnick, a Revon Physician. Mr. James comes to Dr. Resnick's office for an initial appointment. While waiting for his appointment, Mr. James fills out a standard medical history form. Dr. Resnick confirms that Mr. James has type II diabetes and conveys this diagnosis to an administrator working in his practice. Dr. Resnick also refers Mr. James to a retinal specialist, Dr. Melissa Jones, to check for complications of diabetes that can affect the eye and for management of his macular degeneration, and to a pulmonologist, Dr. Frances Drake, for management of his COPD. Both Dr. Jones and Dr. Drake are also Revon physicians. The administrator meets with Mr. James after the appointment, enrolls him in the Revon system, and explains features of the Revon patient registration process and the Revon patient application. Later that day, Mr. James receives an email with a download for the Revon smart phone application. The first time he logs on, he completes the patient registration process and enters his medical history information as requested. He receives a type II diabetes ADM Schedule that includes the various events that are part of Dr. Resnick's preferred treatment plan for type II diabetes, including medication, monitoring blood glucose level, diet, exercise, and follow-up appointments. Dr. Resnick has meanwhile customized his standard type II diabetes ADM Schedule for Mr. James's needs by adjusting the medication dose. The type II diabetes ADM Schedule indicates that Mr. James should return for an initial follow-up appointment with Dr. Resnick in 6 weeks and then every 6 months. It also indicates that he should have an annual eye exam. From now on, Mr. James can display the schedule and checks it every day. He receives reminders of events in the schedule, is able to confirm having performed various actions such as taking medications, monitoring blood glucose level, exercising, and keeping to the diet recommended by Dr. Resnick. In addition, he receives feedback informing him of his achievements in terms of adhering to Dr. Resnick's treatment program and is able to communicate with other patients who have type II diabetes through the patient application.

The following week, Mr. James has his first appointments with Dr. Melissa Jones, the retinal specialist, and Dr. Frances Drake, the pulmonologist, to whom he was referred by Dr. Resnick. Since Dr. Jones and Dr. Drake are Revon physicians, they are able to view Mr. James' medical history information before the appointments through the Revon physician application, so he does not need to complete a paper medical history form. They can also see that Mr. James is already being treated for diabetes. After the appointments, Mr. James receives, in the patient application on his smartphone, a macular degeneration ADM Schedule that includes the events that are part of Dr. Jones's treatment plan for macular degeneration and a COPD ADM schedule that includes the events that are part of Dr. Drake's treatment plan for COPD. Both of these ADM Schedules may have been customized by the relevant physician according to Mr. James' particular needs. From then on, the patient application displays disease-specific schedules so that Mr. James can see the events for each disease and an integrated schedule that displays events for the three diseases in a consolidated manner. In addition, he is now part of the macular degeneration disease network and the COPD disease network and is able to communicate with other patients with these diseases.

On the day of Mr. James's next appointment with Dr. Resnick, Dr. Resnick uses the Revon physician application before the appointment to review Mr. James's self-reported adherence to his recommendations pertaining to medications, monitoring blood glucose level, diet, and exercise. During the appointment, they discuss how he could improve his self-management of his disease. Through the Revon physician application, Dr. Resnick notes that Mr. Jones now has a macular degeneration ADM Schedule and a COPD ADM Schedule, so he is assured that Mr. Jones is receiving treatment for macular degeneration and COPD. Also, on the physician ADM schedule for type II diabetes, the eye exam that Mr. James had during his appointment with Dr. Jones shows up as a confirmed physician event. Thus, Dr. Resnick is assured that this aspect of Mr. James's diabetes care is addressed.

Later that year, while visiting his son in Denver, Colo., Mr. James suddenly starts to feel short of breath. His son drives him to the emergency room. The emergency room physician is a Revon physician and is able to access Mr. James's Patient Medical History in the Revon system. He sees that Mr. James has a history of COPD and which medications he is taking. In the emergency room, a chest X-ray is taken and Mr. James is given oxygen. Nothing alarming is found on the chest X-ray, and Mr. James soon begins to feel better. He leaves the emergency room several hours later. During his next appointment with Dr. Drake, Dr. Drake can see that Mr. James visited the emergency room and that a chest X-ray was taken. He asks Mr. James about the event in order to determine whether he has had further episodes that may require adjustment of the treatment plan.

Meanwhile, a database containing data modules with data from Mr. James's three ADM schedules, in a de-identified form, has been made available through subscription to pharmaceutical companies engaged in developing new medications. One of these companies is looking for subjects for a clinical trial of an experimental therapy for macular degeneration, identifies Mr. James's de-identified ADM, and concludes that he may be eligible for the trial. Shortly thereafter, Mr. James opens his Revon application and finds a notification that a clinical trial of the new therapy will be starting soon. The notification provides contact information for a clinical site where the trial is to be conducted. Mr. James contacts the site and makes an appointment to be screened. He enrolls in the trial, and his ADM schedule for macular degeneration is updated or replaced by one that includes the various events required by the clinical trial protocol. During the trial, the principal investigator on the trial becomes the treating physician for the macular degeneration AMD, and the ADM schedule containing the clinical trial events is used instead of the macular degeneration ADM schedule from Dr. Jones. The clinical trial ADM schedule, among other things, reminds Mr. James of his medical appointments related to his participation in the clinical trial and is used to collect patient-reported outcomes of treatment. The pharmaceutical company that sponsored the clinical trial uses the data in its application to the Food and Drug Administration for approval of the new therapy. At the end of the trial, Mr. James returns to being treated by Dr. Jones, and she becomes the treating physician for the macular degeneration ADM once again.

Implementation

This section includes discussion of certain aspects relating to implementation of the present invention. It should be understood that aspects pertaining to implementation are also discussed elsewhere herein. In general, the present invention may be implemented with any suitable combination of hardware and software in various embodiments. For example, the present invention may be implemented in combination with any or all of the technology described in PCT/US2012/64125 entitled "Systems and Methods for Assembling Electronic Medical Records" filed on Nov. 8, 2012, U.S. application Ser. No. 14/272,714, having the same title and filed on May 8, 2014, PCT/US2013/77227, entitled "Systems and Methods for Using Electronic Medical Records in Conjunction with Patient Apps" and filed on Dec. 20, 2013, the disclosures of each of which are hereby incorporated by reference in their entireties. If implemented as a computer-implemented apparatus, the present invention can be implemented using means for performing those steps and functions described herein that have been selected for the particular embodiment of the invention being implemented.

The present invention may be included in an article of manufacture (e.g., one or more computer program products) comprising, for instance, computer useable media. The media has embodied therein, for instance, computer readable program code means for providing and facilitating the mechanisms of the present invention. The article of manufacture may be included as part of a computer system or sold separately.

In general, the EMR database, may be implemented using any suitable database management system (DBMS). In some embodiments a relational database management system (RDBMS) is used. Various RDBMS software packages are available, e.g., from Microsoft (e.g., Microsoft SQL Server), Oracle (e.g., MySQL), Informix, and IBM (e.g., DB2). Non-SQL based DBMSs, e.g., object database management systems, may be used in various embodiments of the invention. It should be understood that the data may be stored in multiple distinct databases, which may be stored in different locations. Data may be stored and retrieved using standard approaches. It will be understood that data may be stored in the EMR database in any suitable manner. The EMR database may contain references, e.g., pointers, to the data itself, which data may be stored within the EMR system or externally. For example, a EMR for a particular patient may contain a reference to a medical image, which medical image may be stored in a medical image database. In some embodiments the content of the EMR database is digitally watermarked.

It will be understood that the invention may be implemented using one or more computer systems, which may each comprise one or more computers. A computer system of use in the present invention may be a general-purpose computer system that is programmable using a high-level computer programming language. A computer system may be implemented at least in part using specially programmed, special purpose hardware. In general, a computer system includes a processor, which may be a commercially available processor in various embodiments. Such a processor usually executes an operating system which may be, for example, a Windows operating system (Microsoft), MAC OS (Apple), Linux available from various sources, UNIX available from various sources, etc. Many other operating systems may be used. It will be understood that portable electronic devices may use different operating systems from those running on larger devices, e.g., iOS (Apple), Android (Open Handset Alliance), etc. A processor and operating system together provide a computer platform for which application programs in high-level programming languages are written. It should be understood that the invention is not limited to a particular computer system platform, processor, operating system, or network. It would be apparent to those skilled in the art that the present invention could be implemented using any of a wide variety of programming languages or computer systems. It should be appreciated that the invention is not limited to any particular architecture, network, or communication protocol. Various embodiments of the invention may be implemented as programmed or non-programmed elements, or any combination thereof. Various embodiments of the present invention may be programmed using an object-oriented programming language, such as Java or C++. Other object-oriented programming languages may also be used. Functional, scripting, and/or logical programming languages may be used. One or more elements of the invention or aspects thereof may include one or more application programming interfaces (APIs). Such APIs may, for example, facilitate communication between existing electronic medical record systems and a system of the present invention. One or more elements of the invention or aspects thereof may be implemented as or using a "Web service" (which term refers to a software system designed to support interoperable machine-to-machine interaction over a network). One or more elements of the invention or aspects thereof may be implemented using a document description language or environment (e.g., a markup language such as XML or HTML). One of ordinary skill in the art will understand that numerous domain-specific markup languages exist. In some aspects the invention may modify or develop a domain-specific markup language for carrying out at least some functions of the invention. For example, such language may incorporate tags for items of medical data such as images (e.g., X-rays, CT scans, MRI scans, PET scans, etc.), EKGs, EEGs, or other types of health information.

It will be understood that a computer system may include various standard components such as one or more peripheral devices, e.g., one or more input devices (e.g., keyboard, mouse, etc.), one or more output devices (e.g., a display), data storage/memory component(s) (e.g., random access memory, read only memory), communications circuitry, etc. It will be understood that different users may employ computer systems having any of a wide variety of different components or configurations. For example, HCPs or patients may often interact with the EMR system using standard personal computers in their place of work or home.

One or more components of an inventive system may be distributed across one or more computer systems, one or more of which may be coupled to a communications network. For example, various embodiments of the invention or components thereof may be distributed among one or more computer systems configured to provide a service (e.g., servers) to one or more client computers, or to perform a task as part of a distributed system. For example, various embodiments of the invention or components thereof may be performed on a client-server system that includes components distributed among one or more server systems that perform various functions according to various embodiments of the invention. These components may communicate over one or more communication networks using a communication protocol. It would be appreciated that the business entity may or may not own the computer system or components thereof. In some embodiments at least some functions of the system may be outsourced. In some embodiments cloud computing and/or cloud storage may be used at least in part. In some embodiments, EMRs are at least in part stored at a site where medical information is generated or entered ("local storage"), e.g., at a health care organization. In some embodiments, multiple copies of EMRs are stored. For example, at least one copy may be stored by the business entity (e.g., on computer-readable medium owned or controlled by the business entity) and at least one copy may be stored locally and accessible by the business entity. Synchronization may be provided so that all copies remain the same or equivalent at most or essentially all times. References to a "network" or "communication network", unless otherwise indicated or specified, may include one or more intranets or the Internet.

Referring now to FIG. 1, a block diagram of an exemplary cloud computing environment 1000 in which various embodiments may be implemented is shown and described. The cloud computing environment 1000 may include one or more resource providers 1050a, 1050b, 1050c (collectively, 1050). Each resource provider 1050 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1050 may be connected to any other resource provider 1050 in the cloud computing environment 1000. In some implementations, the resource providers 1050 may be connected over a computer network 1100. Each resource provider 1050 may be connected to one or more computing device 1150a, 1150b, 1150c (collectively, 1150), over a computer network 1100.

The cloud computing environment 1000 may include a resource manager 1200. The resource manager 1200 may be connected to the resource providers 1050 and the computing devices 1150 over the computer network 1100. In some implementations, the resource manager 1200 may facilitate the provision of computing resources by one or more resource providers 1050 to one or more computing devices 1150. The resource manager 1200 may receive a request for a computing resource from a computing device 1150. The resource manager 1200 may identify one or more resource providers 1050 capable of providing the computing resource requested by the computing device 1150. The resource manager 1200 may select a resource provider 1050 to provide the computing resource. The resource manager 1200 may facilitate a connection between the resource provider 1050 and the computing device 1150. In some implementations, the resource manager 1200 may establish a connection between a resource provider 1050 and a computing device 1150. In some implementations, the resource manager 1200 may redirect a computing device 1150 to a resource provider 1050 with the requested computing resource.

In some embodiments, all or substantially all health information in an EMR and/or in the EMR database may be stored on computer-readable media within the jurisdiction and/or within the geographical borders (optionally including ocean territory) of a selected country or union. In some embodiments, at least all or substantially all personally identifiable health information in an EMR and/or in the EMR database may be stored on computer-readable media within the jurisdiction and/or within the geographical borders (optionally including ocean territory) of a selected country or union. In some embodiments, all or substantially all health information received and stored (e.g., pertaining to a patient) may be stored on computer-readable media within the jurisdiction and/or within the geographical borders (optionally including ocean territory) of a selected country or union. In some embodiments, at least all or substantially all health information regarding a patient, or at least all or substantially all personally identifiable health information regarding a patient, may be stored in a country or union in which the patient resides or in which the patient seeks health care. In some embodiments, at least all or substantially all personally identifiable health information regarding a patient may be transmitted only within a selected country or union, e.g., a country or union in which the patient resides or in which the patient seeks health care.

In some embodiments of any aspect herein, a country may be the U.S. In some embodiments of any aspect herein, a country may be a country other than the U.S., which country may be any country in the world in various embodiments, e.g., Argentina, Australia, Belgium, Brazil, Canada, Chile, China, Egypt, France, India, Israel, Italy, Japan, Mexico, Netherlands, Norway, Pakistan, Poland, New Zealand, Philippines, Russia, South Africa, South Korea, Spain, Switzerland, Turkey, the United Kingdom. In some embodiments of any aspect herein, a union may be the European Union. In some embodiments of any aspect herein, a country or union may be a country or union in which the patient resides or seeks health care or in which a HCP practices or is registered to practice. In some embodiments of any aspect herein, a country or union may be a country or union in which the business entity is incorporated or its headquarters are physically located.

In some embodiments, an ADM template or other element of an EMR may be generated at least in part by crowdsourcing or using at least some crowdsourcing principles, which may comprise sourcing the generation of rules and/or code to a group of people or community (crowd) through an open call, e.g., a task may be broadcast (e.g., by posting on a web page) to an unknown group of solvers in the form of an open call for solutions. The open call may be completely open or may be restricted at least in part (e.g., a solver or team may need to comprise at least one physician or medical student, in some embodiments). The task(s) may include generating criteria, generating sets of predetermined options, generating any aspect of an ADM template, writing computer code for any aspect of an EMR system or ADM template, etc. Broadcasting a task may comprise at least providing a task description. Broadcasting a task may comprise providing a set of guidelines (e.g., for diagnosis and/or management of a disease) and, e.g., a sample or example ADM template, and/or code therefor. ADM template(s) or other task responses proposed by the crowd may be at least in part owned by the business entity, the proposer(s), or both. The crowd may vote on a proposed ADM template or set of rules, criteria, or options to be adopted. Voting may be limited to HCPs, e.g., physicians. Selection of a "winner" may be at the discretion of the business entity and/or may be approved by or with advice of a professional organization or board (e.g., in a relevant discipline). Prize(s) may be provided, which may, e.g., comprise a share in revenue generated through use of an adopted ADM template. In some embodiments, an ADM template or other element of an EMR may be generated at least in part by posting task(s) for bidding and awarding a contract for such task(s) to a selected bidder or bidders. In some embodiments, teams of physicians, programmers, and/or physician-programmers may be engaged or may participate. In some embodiments HCPs who utilize an ADM-equipped EMR system may contribute suggestions for inclusion of one or more data items in an ADM. For example, a HCP may suggest that a particular diagnostic test be included as a criterion for arriving at a definitive diagnosis or may suggest monitoring of a particular test result. HCPs using the system may be permitted to vote on whether such data item should be included in an ADM. In some embodiments voting may be restricted to HCPs who have created at least a specified number of ADMs and/or have at least a specified number of patients whose EMRs include an ADM for that disease. In some embodiments an ADM template or ADM component is made available in an open source manner, in which the source code is available to HCPs and/or to the general public for use and/or modification from its original design. In some embodiments it is required that any such use or modification is made available at no cost and for any purpose to an entity that at least in part owns, controls, makes, sells, or provides such ADM template or ADM component.

In some aspects, an ADM template may interface with or may be integrated with a standard EMR system. A EMR in some embodiments may comprise a standard EMR for the patient, one or more ADMs in accordance with the present disclosure and, e.g., a patient summary. In some embodiments, a HCP may select one or more ADM templates from the EMR system, which ADM template may be incorporated into or interface with a standard EMR. The ADM template may interface with components of the EMR system such as the EMR manager, EMR analysis components, etc. The EMR database may thus at least in part comprise ADMs that may reside on HCP's or HCO's computers but that may be accessed by other HCPs or subscribers via the EMR system. A EMR database record may thus have different formats or may be a virtual database record that comprises a standard EMR (which may be created by any of diverse EMR systems) and one or more ADMs. The EMR system may thus allow HCPs or HCOs that have, e.g., invested in standard EMR systems and integrated them with other legacy health information systems or operations such as scheduling or billing to continue using such standard EMR systems if desired while adding ADMs and other functions of the EMR system and, e.g., transitioning completely to the central EMR database format over time. In some embodiments, the EMR system may provide multiple different versions of an ADM template, the different versions being adapted for integration into or interfacing with different standard EMR systems. In some embodiments a patient summary may be generated by the EMR system from information in the standard EMR. In some embodiments, the patient's HCP may review and, if appropriate, may correct and/or supplement the automatically generated patient summary. In some embodiments, the patient's HCP may enter information into a patient summary template provided by the EMR system to generate a patient summary. In some embodiments the EMR system may provide tools to extract or analyze data contained in standard EMRs as well as in ADMs. In some aspects, the EMR system may provide tools that support at least partial sharing of health information stored among multiple different standard EMR systems. In some embodiments, the EMR system may provide a uniform user interface, which may enable users (e.g., HCPs) to store and/or retrieve data from multiple heterogeneous standard EMR systems in addition to using and analyzing ADMs. In some embodiments the EMR system may fulfill or substitute for the functions of a health information exchange (HIE), e.g., a regional health information organizations (RHIO) in addition to providing users with the functionality of ADMs and, in some embodiments, the ability to search and analyze them. In some embodiments ADMs may be implemented in conjunction with or as part of a HIE, e.g., a RHIO. In some embodiments a database comprising ADMs may be implemented in conjunction with or as part of a HIE, e.g., a RHIO. In some embodiments, as described herein, ADMs, ADM templates, and, in some embodiments, computer-executable instructions for creating and/or using ADMs may be stored or executed remotely from locations (e.g., HCOs) at which patient data are generated or entered. In some embodiments such ADMs, ADM templates, and/or computer-executable instructions may be at least in part cloud-based, wherein access to such ADMs, ADM templates, and/or computer-executable instructions, is provided (e.g., as a service) over a network, e.g., the Internet or, e.g., a virtual private network. A cloud may be a public cloud, wherein cloud services are provided by, e.g., public cloud service providers that make such services available to the general public, such Amazon AWS, Microsoft, or Google, or may be a cloud that is not generally or broadly available to the public.

In some embodiments an EMR system that is not an ADM-equipped EMR system may be equipped with functionality that makes possible the utilization of ADM templates and/or ADMs within or in connection with such EMR system. In some embodiments, for example, a standard EMR system may be equipped with functionality that makes possible the utilization of ADM templates and/or ADMs within or in connection with such standard EMR system. In some embodiments, systems and methods of equipping a non-ADM equipped EMR system, e.g., a standard EMR system, with functionality that allows such EMR system to create and/or use ADM templates and/or ADMs are described herein. In some embodiments such functionality is provided via a component, e.g., a software component, which component may be referred to as an "ADM component". In some aspects, a non-transitory computer-readable medium comprising an ADM component is disclosed herein. In some embodiments an ADM component may be provided to an HCP or to an HCO that has entered into an appropriate agreement with a business entity that at least in part owns, controls, makes, sells, or provides the ADM component. In some embodiments an ADM component may be provided to a member of an information technology (IT) department at a HCO, such as a system administrator. The HCO may provide access to the ADM component to a selected set of computers and/or HCPs.

An ADM component may be provided in any suitable way in various embodiments. For example, in some embodiments an individual visits a website and downloads from such website a plug-in, wherein the plug-in comprises or consists of an ADM component that provides such additional functionality. As will be appreciated, the term "plug-in" refers to a software component or set of software components that adds specific functionality (abilities) to another software application. In some embodiments an ADM component is a plug-in for a standard EMR system. In some aspects, a plug-in may extend the usability of a standard EMR system. The term "plug-in" is used interchangeably herein with "add-on" or "extension". In some embodiments an ADM component, e.g., a plug-in, is designed to function specifically with a particular EMR system, e.g., a particular standard EMR system. In some embodiments an ADM component, e.g., a plug-in, is designed to function with any of multiple standard EMR systems. In some embodiments an individual may be required to enter appropriate identifying information and is then offered the option of downloading an ADM component. Identifying information may be, e.g., a license number, DEA number or other prescriber number, or a code. A code may be provided by, e.g., (i) a company that at least in part owns, controls, makes, sells, or provides an EMR system into which such component is to be installed, e.g., a company that at least in part owns, controls, makes, sells, or provides a standard EMR system, (ii) a business entity that at least in part owns, controls, makes, sells, or provides, the ADM component, (iii) a sponsor of a trial (e.g., a pharmaceutical company), etc. In some embodiments the website is at least in part owned or controlled by a business entity that at least in part owns, controls, makes, sells, or provides an EMR system. In some embodiments the website is at least in part owned or controlled by a business entity that at least in part owns, controls, makes, sells, or provides the ADM component. In some embodiments an ADM component may be provided on a tangible computer-readable medium such as a CDROM. In some embodiments installation from a tangible computer-readable medium may require entry of identifying information or a code and/or may be limited to particular computers. In some embodiments an ADM component may be provided as part of an upgrade of a standard EMR system. In some embodiments an ADM component may be an option that may be furnished together with or after adoption of an EMR system lacking ADM functionality, e.g., standard EMR system, by a HCO or HCP. In some embodiments an ADM component may be provided for purposes of use in clinical trial enrollment and/or electronic data capture.

An EMR system that utilizes ADMs, e.g., an EMR system in which EMRs are organized at least in part around ADMs from the outset or a standard EMR system that comprises an ADM component, may be referred to as an "ADM-equipped EMR system". In some embodiments an ADM-equipped EMR system, e.g., an EMR system comprising an ADM component, differs from a standard EMR system in one or more ways. In some embodiments, following installation of an ADM component into a standard EMR system, one or more new link(s) are displayed within EMRs of at least some patients of an HCP who uses the system. Such link(s), when active, may allow a user to access functions that allow creation and/or use of an ADM. For purposes hereof, a situation in which a user of an EMR system has access to functionality for creation and/or use of ADMs may be referred to as being in an "ADM environment." Thus an ADM component may be a component that equips a standard EMR system with computer-executable instructions appropriate to establish an ADM environment and to manage and allow use of ADMs created using such an environment. In some embodiments, clicking on a link opens an ADM template or, after data has been entered into at least one ADM template, allows the user to select or open an existing ADM. The term "link" is used here in a general sense to refer to any element that allows navigation. In some embodiments a link may be in the form of, or contained within, an icon, tab, or other GUI element. In some embodiments clicking the link bring the user directly to an ADM template or existing ADM. In some embodiments clicking the link brings the user to an ADM template or ADM via one or more steps. For example, the user may be prompted to make a further selection after clicking the link. The ADM template or ADM may be used, in various embodiments, in any one or more ways or for any one or more purposes described herein.

Referring now to FIG. 1, a block diagram of an exemplary cloud computing environment 1000 is shown and described. The cloud computing environment 1000 may include one or more resource providers 1050a, 1050b, 1050c (collectively, 1050). Each resource provider 1050 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1050 may be connected to any other resource provider 1050 in the cloud computing environment 1000. In some implementations, the resource providers 1050 may be connected over a computer network 1100. Each resource provider 1050 may be connected to one or more computing device 1150a, 1150b, 1150c (collectively, 1150), over a computer network 1100.

The cloud computing environment 1000 may include a resource manager 1200. The resource manager 1200 may be connected to the resource providers 1050 and the computing devices 1150 over the computer network 1100. In some implementations, the resource manager 1200 may facilitate the provision of computing resources by one or more resource providers 1050 to one or more computing devices 1150. The resource manager 1200 may receive a request for a computing resource from a computing device 1150. The resource manager 1200 may identify one or more resource providers 1050 capable of providing the computing resource requested by the computing device 1150. The resource manager 1200 may select a resource provider 1050 to provide the computing resource. The resource manager 1200 may facilitate a connection between the resource provider 1050 and the computing device 1150. In some implementations, the resource manager 1200 may establish a connection between a resource provider 1050 and a computing device 1150. In some implementations, the resource manager 1200 may redirect a computing device 1150 to a resource provider 1050 with the requested computing resource.

It is expressly contemplated that each of the various aspects, embodiments, and features thereof described herein may be freely combined with any or all other aspects, embodiments, and features. The resulting aspects and embodiments (e.g., products and methods) are within the scope of the invention. It should be understood that headings herein are provided for purposes of convenience and do not imply any limitation on content included below such heading or the use of such content in combination with content included below other headings.

All articles, books, patent applications, patents, other publications, websites, and databases mentioned in this application are incorporated herein by reference. In the event of a conflict between the specification and any of the incorporated references the specification (including any amendments thereto) shall control. Unless otherwise indicated, art-accepted meanings of terms and abbreviations are used herein.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the claims articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim. For example, any claim that is dependent on another claim may be modified to include one or more elements, limitations, clauses, or descriptive terms, found in any other claim that is dependent on the same base claim. Furthermore, where the claims recite a product (e.g., an apparatus or device or computer-readable medium), it is to be understood that methods of using the product according to any of the methods disclosed herein, and methods of making the product, are included within the scope of the invention, unless otherwise indicated or unless it would be evident to one of ordinary skill in the art that a contradiction or inconsistency would arise. For example, methods comprising executing computer-readable instructions to perform one or more acts or steps relating to an ADM, EMR, or database, such as accessing, retrieving, or analyzing one or more data elements therein, are provided. Any method may comprise a step of receiving a transmission, which transmission may comprise a query. Any method may comprise a step of analyzing a transmission, which transmission may comprise a query. Any method may comprise a step of transmitting (e.g., following receipt of a query), which transmission may comprise a response to a query. An apparatus may comprise one or more computer-readable media (e.g., memory). A memory may comprise one or more non-transitory computer-readable media. In some embodiments a memory may comprise at least a first medium and a second medium, wherein the first medium comprises a database and the second medium comprises the instructions. A database, or instructions, or both, may be stored on or divided among any number of computer-readable media, in various embodiments. An apparatus may comprise one or more processors. An apparatus may comprise one or more computer-readable media and one or more processors. A system may comprise an apparatus, which may itself comprise one or more systems or apparatuses. A claim expressed at least in part in terms a system may be expressed at least in part in terms of an apparatus (or apparatuses), or vice versa. Where a contributor or an act performed by a contributor are described, such contributor may in at least some embodiments be a designee of the contributor, and/or such act may be performed by a designee of the contributor, e.g., under direction of the contributor. Where an incentive is provided to a contributor, such incentive may in at least some embodiments be provided to a contibutor's designee.

Where elements are presented as lists, it is to be understood that each subgroup of the elements is also disclosed, and any element(s) may be removed from the group. The invention provides all such embodiments.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). Where ranges are given, endpoints are included. Furthermore, it is to be understood that unless otherwise indicated or otherwise evident from the context and understanding of one of ordinary skill in the art, values that are expressed as ranges may assume any specific value or subrange within the stated ranges in different embodiments of the invention, to the tenth of the unit of the lower limit of the range, unless the context clearly dictates otherwise. Any one or more embodiment(s), element(s), feature(s), aspect(s), component(s) etc., of the present invention may be explicitly excluded from any one or more of the claims.

We claim:

1. A computer program product for creating, augmenting, or updating electronic medical records (EMRs) or electronic medical data modules, the computer program product comprising a non-transitory computer-readable medium encoded with computer-executable instructions for performing a method comprising:
   (a) maintaining, for each a plurality of diseases, association data identifying one or more events as disease relevant events for that disease;
   (b) receiving input comprising a disease identifier and a patient identifier;
   (c) generating a first schedule, wherein the first schedule is a schedule of events for managing the disease, wherein generating the first schedule comprises:
      (i) searching a database to identify whether there are any existing schedules for the patient associated with the patient identifier; and
      (ii) for each existing schedule identified for the patient associated with the patient identifier which is associated with a different disease:
         (A) identifying, using the association data, if any events from that existing schedule are disease relevant events for the disease for which the first schedule is being generated; and
         (B) automatically populating the first schedule of events with each event in that existing schedule identified as a disease relevant event for the disease for which the first schedule of events is being generated, wherein automatically populating the first schedule of events comprises adding the event in that existing schedule identified as a disease relevant event when that event is not already present in the first schedule of events;
   (d) receiving input indicating that an event comprised by the first schedule has occurred; and
   (e) in response to receiving the input indicating that the event comprised by the first schedule has occurred:
      (i) identifying, using the association data, the event comprised by the first schedule as a disease relevant event for a disease for which a second schedule had been generated for the patient, wherein the disease for which the second schedule had been generated is different from the disease for which the first schedule of events was generated; and
      (ii) populating the second schedule for the patient with information indicating that the event comprised by the first schedule has occurred.

2. The computer program product of claim 1, wherein:
   (a) one or more of the events are selected by a treating physician associated with the first schedule of events for managing the disease for that patient; and
   (b) the system is configured to:
      (i) identify any events in existing schedules in the database for the patient associated with the patient identifier which conflict with, or are redundant with, an event selected by the treating physician associated with the first schedule; and
      (ii) notify the treating physician associated with the first schedule of all such conflicting or redundant events.

3. The computer program product of claim 1, wherein the events comprise physician events and patient events.

4. The computer program product of claim 1, wherein the computer-executable instructions comprise instructions for providing an output comprising the first schedule to a treating physician and a patient.

5. The computer program product of claim 1, wherein the computer-executable instructions comprise instructions for modifying the first schedule in response to an input.

6. The computer program product of claim 1, wherein the computer-executable instructions comprise:
   (i) instructions for receiving an input indicating that an event occurred, wherein the input comprises one or more of:
      (A) a temporal item from a group consisting of (1) a date, and (2) an approximate date that the event occurred,
      (B) a result of the event, and
   (ii) instructions for updating the first schedule upon receipt of the input to indicate that the event occurred.

7. The computer program product of claim 1, wherein the computer-executable instructions comprise:
   (i) instructions for receiving a plurality of inputs over time indicating that a plurality of events occurred, wherein each input from the plurality of inputs comprises one or more of:
      (A) a temporal item from a group consisting of (1) a date, and (2) an approximate date that an event occurred,
      (B) a result of the event, and
   (ii) instructions for updating the first schedule upon receipt of an input from the plurality of inputs to indicate that an event occurred, and
   (iii) instructions for maintaining an ongoing record of events relevant to management of the disease over a time period of at least 3 months.

8. The computer program product of claim 1, wherein the computer-executable instructions comprise instructions for: updating a patient application as dates scheduled for events approach, issuing notifications to a patient application, enrolling a patient in a patient network, ranking a patient based on their adherence to the first schedule.

9. The computer program product of claim 2, wherein:
   (a) the database stores data comprising a plurality of schedules, each of which is associated with a disease, and patient, and a single treating physician;
   (b) the system is configured to, when:
      (i) an event in an existing schedule in the database for the patient associated with the patient identifier is identified as conflicting with an event selected by the treating physician associated with the schedule of events for managing the disease for that patient; and
      (ii) the treating physician associated with the schedule comprising the identified conflicting event is different from the treating physician associated with the schedule of events for managing the disease for that patient;
   notify the treating physician associated with the schedule comprising the identified conflicting event.

10. The computer program product of claim 1, wherein the system is configured to allow for anonymous patient invitation to clinical trials by performing acts comprising:

(a) presenting an interface operable by a clinical trial sponsor to:
   (i) specify disease diagnosis, patient characteristics and disease characteristics;
   (ii) indicate that one or more patients matching the specified disease diagnosis, patient characteristics and disease characteristics should be invited to participate in a clinical trial;
(b) upon receiving an indication from the clinical trial sponsor that one or more patients should be invited to participate in the clinical trial, contacting the one or more patients without providing patient identifying information to the clinical trial sponsor and notifying each of the one or more patients of the trial and enrollment information in the trial.

11. The computer program product of claim 1, wherein:
(a) the system comprising the database further comprises a plurality of template schedules, wherein each template schedule is associated with a disease but not with a patient;
(b) the system is configured to:
   (i) determine a default template schedule for a particular disease by performing acts comprising:
      (A) providing one or more task guidelines to one or more task participants, wherein the one or more task guidelines comprise identification of the particular disease;
      (B) receiving one or more responses from the one or more task participants; and
      (C) determining the default template schedule based on the one or more responses;
   (ii) when generating the first schedule, provide an interface operable by a treating physician to select the default template schedule for the particular disease when the particular disease is the same as the disease for which the first schedule is being generated.

12. The computer program product of claim 11, wherein:
(a) the one or more task guidelines comprise one or more proposed templates;
(b) each of the one or more responses comprises a vote from a task participant for one of the one or more proposed templates;
(c) determining the default template schedule based on the one or more responses comprises determining the proposed template for which the most votes were received; and
(d) each of the one or more task participants is a health care provider identified as a treating physician for at least a specified number of patients diagnosed with the particular disease based on existing schedules stored in the database.

13. The computer program product of claim 1, wherein:
(a) the database stores data comprising a plurality of schedules, each of which is associated with a disease, and patient, and a single treating physician;
(b) the treating physician associated with the first schedule is different from the treating physician associated with the second schedule; and
(c) the method comprises updating the second schedule with one or more events added to the first schedule by the treating physician associated with the first schedule.

14. A computer program product comprising computer-executable instructions encoded on a non-transitory computer readable medium for:
   (i) maintaining, for each a plurality of diseases, association data identifying one or more events as disease relevant events for that disease;
   (ii) generating a first schedule, wherein the first schedule is a schedule for a patient for performing physician events and patient events relevant to managing a disease, wherein generating the first schedule:
      (a) searching a database to identify whether there are any existing schedules for the patient; and
      (b) for each existing schedule identified for the patient which is associated with a different disease:
         (I) identifying, using the association data, if any events from that existing schedule are disease relevant events for the disease for which the first schedule is being generated; and
         (II) automatically populating the first schedule being generated with each event in that existing schedule identified as a disease relevant event for the disease for which the schedule is being generated, wherein automatically populating the first schedule comprises adding the event in that existing schedule identified as a disease relevant event when that event is not already present in the first schedule;
   (iii) storing the schedule in association with an identifier of the patient and the treating physician of the patient,
   (iv) causing the schedule to be displayed on a device controlled by the physician or a device controlled by the patient upon receiving a request from the physician device or patient device, respectively; and
   (v) in response to receiving an input indicating that an event comprised by the first schedule has occurred:
      (a) updating the first schedule to indicate that the event has occurred;
      (b) identifying using the association data, the event comprised by the first schedule as a disease relevant event for a disease for which a second schedule had been generated for the patient, wherein the disease for which the second schedule had been generated is different from the disease for which the first schedule had been generated; and
      (c) updating the second schedule for the patient with information indicating that the event comprised by the first schedule has occurred.

15. The computer program product of claim 14, wherein physician events include diagnostic procedures and therapeutic procedures and patient events include taking medications, performing body monitoring, diet, and exercise.

16. A method of managing a patient having a disease comprising steps of:
(a) maintaining, for each a plurality of diseases, association data identifying one or more events as disease relevant events for that disease;
(b) receiving, in a system, input comprising a patient identifier and a disease diagnosis;
(c) generating a first schedule, wherein the first schedule is a schedule comprising treating physician-selected events for managing the disease, wherein generating the first schedule comprises:
   (i) searching a database to identify whether there are any existing schedules for the patient associated with the patient identifier; and
   (ii) for each existing schedule identified for the patient associated with the patient identifier which is associated with a different disease:

(A) identifying, using the association data, if any events from that existing schedule are disease relevant events for the disease for which the first schedule is being generated; and (B) automatically populating the first schedule with each event in that existing schedule identified as a disease relevant event for the disease for which the first schedule is being generated, wherein automatically populating the first schedule of events comprises adding the event in that existing schedule identified as a disease relevant event when that event is not already present in the first schedule of events;

(d) providing the patient with an application that allows for display of the schedule, generates reminders of events, and enables a patient to communicate with other patients who have the same disease;

(e) receiving input confirming the occurrence of a plurality of events in an event comprised by the first schedule; and (f) response to receiving the input confirming occurrence of the event comprised by the first schedule:
  (i) updating the first schedule based on the input;
  (ii) identifying, using the association data, the event comprised by the first schedule as a disease relevant event for a disease for which a second schedule had been generated for the patient, wherein the disease for which the second schedule had been generated is different from the disease for which the first schedule of events was generated; and
  (iii) populating the second schedule for the patient with information indicating that the event comprised by the first schedule has occurred.

17. The method of claim 16, wherein:
(a) the application runs on a portable electronic device having a touch sensitive screen and being remote from the database; and
(b) the application is configured to display a plurality of disease specific interfaces, and to allow the patient to navigate between interfaces from the plurality of disease specific interfaces by:
  (i) moving horizontally across the touch sensitive screen of the portable electronic device; or
  (ii) moving vertically across the touch sensitive screen of the portable electronic device.

18. The method of claim 16, further comprising:
(a) ranking the patient's adherence to the first schedule as compared with other patients with the same disease, and
(b) providing feedback to the user based at least in part on the ranking.

19. A method of managing a patient having a disease comprising steps of:
(a) maintaining, for each a plurality of diseases, association data identifying one or more events as disease relevant events for that disease;
(b) receiving, in a system, an input comprising a patient identifier and a disease diagnosis;
(c) generating a first schedule, wherein the first schedule is a schedule comprising treating physician-selected events for managing the disease wherein generating the first schedule comprises:
  (i) searching a database to identify whether there are any existing schedules for the patient associated with the patient identifier; and
  (ii) for each existing schedule identified for the patient associated with the patient identifier which is associated with a different disease:
    (A) identifying, using the association data, if any events from that existing schedule are disease relevant events for the disease for which the first schedule is being generated; and
    (B) automatically populating the first schedule with each event in that existing schedule identified as a disease relevant event for the disease for which the first schedule is being generated, wherein automatically populating the first schedule of events comprises adding the event in that existing schedule identified as a disease relevant event when that event is not already present in the first schedule of events;
(d) providing the treating physician with access to the first schedule;
(e) providing the patient with an application that allows for display of the first schedule, generates reminders of events, and enables a patient to communicate with other patients who have the same disease;
(f) receiving input confirming the occurrence of an event comprised by the first schedule; and
(g) in response to receiving the input confirming occurrence of the event comprised by the first schedule:
  (i) updating the first schedule for both the treating physician and the patient based on the input;
  (ii) identifying, using the association data, the event comprised by the first schedule as a disease relevant event for a disease for which a second schedule had been generated for the patient, wherein the disease for which the second schedule had been generated is different from the disease for which the first schedule of events was generated; and
  (iii) populating the second schedule for the patient with information indicating that the event comprised by the first schedule has occurred.

20. The method of claim 19, wherein the application runs on a portable electronic device.

* * * * *